United States Patent
Friedl et al.

(10) Patent No.: US 10,022,379 B2
(45) Date of Patent: *Jul. 17, 2018

(54) DPP-IV INHIBITOR COMBINED WITH A FURTHER ANTIDIABETIC AGENT, TABLETS COMPRISING SUCH FORMULATIONS, THEIR USE AND PROCESS FOR THEIR PREPARATION

(71) Applicant: Boehringer Ingelheim International GmbH, Ingelheim am Rhein (DE)

(72) Inventors: Thomas Friedl, Ochsenhausen (DE); Michael Braun, Senden (DE); Kenji Egusa, Biberach an der Riss (DE); Hikaru Fujita, Osaka (JP); Megumi Maruyama, Hyogo (JP); Takaaki Nishioka, Kobe (JP)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/403,705

(22) Filed: Jan. 11, 2017

(65) Prior Publication Data

US 2017/0119773 A1 May 4, 2017

Related U.S. Application Data

(63) Continuation of application No. 15/203,906, filed on Jul. 7, 2016, now abandoned, which is a continuation of application No. 14/836,996, filed on Aug. 27, 2015, now Pat. No. 9,415,016, which is a continuation of application No. 12/935,634, filed as application No. PCT/EP2009/053978 on Apr. 2, 2009, now Pat. No. 9,155,705.

(60) Provisional application No. 61/087,343, filed on Aug. 8, 2008.

(30) Foreign Application Priority Data

Apr. 3, 2008 (EP) ..................................... 08154039

(51) Int. Cl.
*A61K 31/522* (2006.01)
*A61K 9/00* (2006.01)
*A61K 31/155* (2006.01)
*A61K 9/20* (2006.01)
*A61K 9/28* (2006.01)
*A61K 9/24* (2006.01)

(52) U.S. Cl.
CPC .......... *A61K 31/522* (2013.01); *A61K 9/0053* (2013.01); *A61K 9/2009* (2013.01); *A61K 9/209* (2013.01); *A61K 9/2013* (2013.01); *A61K 9/2027* (2013.01); *A61K 9/2059* (2013.01); *A61K 9/282* (2013.01); *A61K 9/2813* (2013.01); *A61K 9/2866* (2013.01); *A61K 31/155* (2013.01)

(58) Field of Classification Search
None
See application file for complete search history.

(56) References Cited

U.S. PATENT DOCUMENTS

| | | | |
|---|---|---|---|
| 2,056,046 A | 9/1936 | Fourneau | |
| 2,375,138 A | 5/1945 | Victors | |
| 2,629,736 A | 2/1953 | Krimmel | |
| 2,730,544 A | 1/1956 | Sahyun | |
| 2,750,387 A | 6/1956 | Krimmel | |
| 2,928,833 A | 3/1960 | Leake et al. | |
| 3,174,901 A | 3/1965 | Sterne | |
| 3,236,891 A | 2/1966 | Seemuller | |
| 3,454,635 A | 7/1969 | Muth | |
| 3,673,241 A | 6/1972 | Marxer | |
| 3,925,357 A | 12/1975 | Okada et al. | |
| 4,005,208 A | 1/1977 | Bender et al. | |
| 4,061,753 A | 12/1977 | Bodor et al. | |
| 4,382,091 A | 5/1983 | Benjamin et al. | |
| 4,599,338 A | 7/1986 | Regnier et al. | |
| 4,639,436 A | 1/1987 | Junge et al. | |
| 4,687,777 A | 8/1987 | Meguro et al. | |
| 4,741,898 A | 5/1988 | Mallik et al. | |
| 4,743,450 A | 5/1988 | Harris et al. | |
| 4,764,466 A | 8/1988 | Suyama et al. | |
| 4,816,455 A | 3/1989 | Schickaneder et al. | |
| 4,873,330 A | 10/1989 | Lindholm | |
| 4,968,672 A | 11/1990 | Jacobson et al. | |
| 5,034,225 A | 7/1991 | Bennett et al. | |
| 5,041,448 A | 8/1991 | Janssens et al. | |
| 5,051,509 A | 9/1991 | Nagano et al. | |

(Continued)

FOREIGN PATENT DOCUMENTS

| | | |
|---|---|---|
| AU | 2003280680 A1 | 6/2004 |
| AU | 2009224546 A1 | 9/2009 |

(Continued)

OTHER PUBLICATIONS

Mayo Clinic (http://www.mayoclinic.org/diseases-conditions/type-2-diabetes/home/ovc-20169860, last visit Mar. 29, 2017).*

(Continued)

*Primary Examiner* — Ernst V Arnold
*Assistant Examiner* — Kyung S Chang
(74) *Attorney, Agent, or Firm* — Marc Began; David L. Kershner

(57) ABSTRACT

The present invention relates to pharmaceutical compositions comprising fixed dose combinations of a DPP-4 inhibitor drug and a partner drug, processes for the preparation thereof, and their use to treat certain diseases.

20 Claims, No Drawings

(56) References Cited

U.S. PATENT DOCUMENTS

| | | |
|---|---|---|
| 5,051,517 A | 9/1991 | Findeisen et al. |
| 5,084,460 A | 1/1992 | Munson, Jr. et al. |
| 5,120,712 A | 6/1992 | Habener |
| 5,130,244 A | 7/1992 | Nishimaki et al. |
| 5,164,526 A | 11/1992 | Macher |
| 5,219,870 A | 6/1993 | Kim |
| 5,223,499 A | 6/1993 | Greenlee et al. |
| 5,234,897 A | 8/1993 | Findeisen et al. |
| 5,258,380 A | 11/1993 | Janssens et al. |
| 5,266,555 A | 11/1993 | Findeisen et al. |
| 5,273,995 A | 12/1993 | Roth |
| 5,284,967 A | 2/1994 | Macher |
| 5,300,298 A | 4/1994 | LaNoue |
| 5,329,025 A | 7/1994 | Wong et al. |
| 5,332,744 A | 7/1994 | Chakravarty et al. |
| 5,389,642 A | 2/1995 | Dorsch et al. |
| 5,399,578 A | 3/1995 | Buhlmayer et al. |
| 5,407,929 A | 4/1995 | Takahashi et al. |
| 5,461,066 A | 10/1995 | Gericke et al. |
| 5,470,579 A | 11/1995 | Bonte et al. |
| 5,591,762 A | 1/1997 | Hauel et al. |
| 5,594,003 A | 1/1997 | Hauel et al. |
| 5,602,127 A | 2/1997 | Hauel et al. |
| 5,614,519 A | 3/1997 | Hauel et al. |
| 5,719,279 A | 2/1998 | Kufner-Muhl et al. |
| 5,728,849 A | 3/1998 | Bouchard et al. |
| 5,753,635 A | 5/1998 | Buckman et al. |
| 5,830,908 A | 11/1998 | Grunenberg et al. |
| 5,879,708 A | 3/1999 | Makino et al. |
| 5,958,951 A | 9/1999 | Ahrndt et al. |
| 5,965,555 A | 10/1999 | Gebert et al. |
| 5,965,592 A | 10/1999 | Buhlmayer et al. |
| 6,011,049 A | 1/2000 | Whitcomb |
| 6,107,302 A | 8/2000 | Carter et al. |
| 6,166,063 A | 12/2000 | Villhauer |
| 6,200,958 B1 | 3/2001 | Odaka et al. |
| 6,248,758 B1 | 6/2001 | Klokkers et al. |
| 6,303,661 B1 | 10/2001 | Demuth et al. |
| 6,342,601 B1 | 1/2002 | Bantick et al. |
| 6,372,940 B1 | 4/2002 | Cavazza |
| 6,448,323 B1 | 9/2002 | Jordan et al. |
| 6,548,481 B1 | 4/2003 | Demuth et al. |
| 6,579,868 B1 | 6/2003 | Asano et al. |
| 6,689,353 B1 | 2/2004 | Wang et al. |
| 6,699,845 B2 | 3/2004 | Oobae et al. |
| 6,727,261 B2 | 4/2004 | Gobbi et al. |
| 6,784,195 B2 | 8/2004 | Hale et al. |
| 6,821,978 B2 | 11/2004 | Chackalamannil et al. |
| 6,869,947 B2 | 3/2005 | Kanstrup et al. |
| 6,890,898 B2 | 5/2005 | Bachovchin et al. |
| 6,995,183 B2 | 2/2006 | Hamann et al. |
| 7,034,039 B2 | 4/2006 | Oi et al. |
| 7,060,722 B2 | 6/2006 | Kitajima et al. |
| 7,074,794 B2 | 7/2006 | Kitajima et al. |
| 7,074,798 B2 | 7/2006 | Yoshikawa et al. |
| 7,074,923 B2 | 7/2006 | Dahanukar et al. |
| 7,109,192 B2 | 9/2006 | Hauel et al. |
| 7,179,809 B2 | 2/2007 | Eckhardt et al. |
| 7,183,280 B2 | 2/2007 | Himmelsbach et al. |
| 7,192,952 B2 | 3/2007 | Kanstrup et al. |
| 7,217,711 B2 | 5/2007 | Eckhardt et al. |
| 7,220,750 B2 | 5/2007 | Himmelsbach et al. |
| 7,235,538 B2 | 6/2007 | Kanstrup et al. |
| 7,247,478 B2 | 7/2007 | Eberhardt et al. |
| 7,282,219 B2 | 10/2007 | Nomura et al. |
| 7,291,642 B2 | 11/2007 | Kauffmann-Hefner et al. |
| 7,361,687 B2 | 4/2008 | Barth et al. |
| 7,393,847 B2 | 7/2008 | Eckhardt et al. |
| 7,407,955 B2 | 8/2008 | Himmelsbach et al. |
| 7,407,995 B2 | 8/2008 | Ok et al. |
| 7,432,262 B2 | 10/2008 | Eckhardt et al. |
| 7,439,370 B2 | 10/2008 | Eckhardt |
| 7,470,716 B2 | 12/2008 | Eckhardt et al. |
| 7,476,671 B2 | 1/2009 | Eckhardt et al. |
| 7,482,337 B2 | 1/2009 | Himmelsbach et al. |
| 7,495,002 B2 | 2/2009 | Langkopf et al. |
| 7,495,003 B2 | 2/2009 | Eckhardt et al. |
| 7,495,005 B2 | 2/2009 | Himmelsbach et al. |
| 7,501,426 B2 | 3/2009 | Himmelsbach et al. |
| 7,550,455 B2 | 6/2009 | Himmelsbach et al. |
| 7,560,450 B2 | 7/2009 | Eckhardt et al. |
| 7,566,707 B2 | 7/2009 | Eckhardt et al. |
| 7,569,574 B2 | 8/2009 | Maier et al. |
| 7,579,449 B2 | 8/2009 | Eckhardt et al. |
| 7,610,153 B2 | 10/2009 | Carter, Jr. et al. |
| 7,645,763 B2 | 1/2010 | Himmelsbach et al. |
| 7,718,666 B2 | 5/2010 | Boehringer et al. |
| 7,754,481 B2 | 7/2010 | Eberhardt et al. |
| 7,799,782 B2 | 9/2010 | Munson et al. |
| 7,820,815 B2 | 10/2010 | Boehringer et al. |
| 7,838,529 B2 | 11/2010 | Himmelsbach et al. |
| 8,039,477 B2 | 10/2011 | Hendrix et al. |
| 8,071,583 B2 | 12/2011 | Himmelsbach |
| 8,106,060 B2 | 1/2012 | Pfrengle et al. |
| 8,119,648 B2 | 2/2012 | Himmelsbach et al. |
| 8,158,633 B2 | 4/2012 | Hendrix et al. |
| 8,178,541 B2 | 5/2012 | Himmelsbach et al. |
| 8,232,281 B2 | 7/2012 | Dugi et al. |
| 8,338,450 B2 | 12/2012 | Arora et al. |
| 8,399,414 B2 | 3/2013 | Harada et al. |
| 8,455,435 B2 | 6/2013 | Franz et al. |
| 8,513,264 B2 | 8/2013 | Mark et al. |
| 8,541,450 B2 | 9/2013 | Pfrengle et al. |
| 8,637,530 B2 | 1/2014 | Pfrengle et al. |
| 8,664,232 B2 | 3/2014 | Himmelsbach et al. |
| 8,673,927 B2 | 3/2014 | Dugi et al. |
| 8,679,520 B2 | 3/2014 | Horres et al. |
| 8,697,868 B2 | 4/2014 | Himmelsbach et al. |
| 8,785,455 B2 | 7/2014 | Hotter et al. |
| 8,846,695 B2 | 9/2014 | Dugi |
| 8,853,156 B2 | 10/2014 | Dugi et al. |
| 8,865,729 B2 | 10/2014 | Sieger et al. |
| 8,883,800 B2 | 11/2014 | Pfrengle et al. |
| 8,883,805 B2 | 11/2014 | Pfrengle et al. |
| 8,962,636 B2 | 2/2015 | Pfrengle et al. |
| 9,034,883 B2 | 5/2015 | Klein et al. |
| 9,108,964 B2 | 8/2015 | Himmelsbach et al. |
| 9,149,478 B2 | 10/2015 | Klein et al. |
| 9,155,705 B2 | 10/2015 | Friedl et al. |
| 9,173,859 B2 | 11/2015 | Dugi et al. |
| 9,186,392 B2 | 11/2015 | Klein et al. |
| 9,199,998 B2 | 12/2015 | Pfrengle et al. |
| 9,212,183 B2 | 12/2015 | Sieger et al. |
| 9,266,888 B2 | 2/2016 | Sieger et al. |
| 9,321,791 B2 | 4/2016 | Himmelsbach et al. |
| 9,415,016 B2 | 8/2016 | Friedl et al. |
| 9,486,426 B2 | 8/2016 | Eller |
| 9,457,029 B2 | 10/2016 | Dugi et al. |
| 2001/0020006 A1 | 9/2001 | Demuth et al. |
| 2001/0051646 A1 | 12/2001 | Demuth et al. |
| 2002/0019411 A1 | 2/2002 | Robl et al. |
| 2002/0137903 A1 | 9/2002 | Ellsworth et al. |
| 2002/0160047 A1 | 10/2002 | Hussain et al. |
| 2002/0161001 A1 | 10/2002 | Kanstrup et al. |
| 2002/0169174 A1 | 11/2002 | Chackalamannil et al. |
| 2002/0198205 A1 | 12/2002 | Himmelsbach et al. |
| 2003/0040490 A1 | 2/2003 | Sugiyama et al. |
| 2003/0078269 A1 | 4/2003 | Pearson et al. |
| 2003/0100563 A1 | 5/2003 | Edmondson et al. |
| 2003/0104053 A1 | 6/2003 | Gusler et al. |
| 2003/0104983 A1 | 6/2003 | DeFelippis et al. |
| 2003/0105077 A1 | 6/2003 | Kanstrup et al. |
| 2003/0114390 A1 | 6/2003 | Washburn et al. |
| 2003/0130313 A1 | 7/2003 | Fujino et al. |
| 2003/0149071 A1 | 8/2003 | Gobbi et al. |
| 2003/0153509 A1 | 8/2003 | Bachovchin et al. |
| 2003/0166578 A1 | 9/2003 | Arch et al. |
| 2003/0199528 A1 | 10/2003 | Kanstrup et al. |
| 2003/0224043 A1 | 12/2003 | Appel et al. |
| 2003/0232987 A1 | 12/2003 | Dahanukar et al. |
| 2003/0236272 A1 | 12/2003 | Carr |
| 2004/0023981 A1 | 2/2004 | Ren et al. |
| 2004/0034014 A1 | 2/2004 | Kanstrup et al. |
| 2004/0037883 A1 | 2/2004 | Zhou et al. |

(56) References Cited

U.S. PATENT DOCUMENTS

| | | |
|---|---|---|
| 2004/0063725 A1 | 4/2004 | Barth et al. |
| 2004/0077645 A1 | 4/2004 | Himmelsbach et al. |
| 2004/0082570 A1 | 4/2004 | Yoshikawa et al. |
| 2004/0087587 A1 | 5/2004 | Himmelsbach et al. |
| 2004/0097510 A1 | 5/2004 | Himmelsbach et al. |
| 2004/0116328 A1 | 6/2004 | Yoshikawa et al. |
| 2004/0122048 A1 | 6/2004 | Benjamin et al. |
| 2004/0122228 A1 | 6/2004 | Maier et al. |
| 2004/0126358 A1 | 7/2004 | Warne et al. |
| 2004/0138214 A1 | 7/2004 | Himmelsbach et al. |
| 2004/0138215 A1 | 7/2004 | Eckhardt et al. |
| 2004/0152659 A1 | 8/2004 | Matsuoka et al. |
| 2004/0152720 A1 | 8/2004 | Hartig et al. |
| 2004/0166125 A1 | 8/2004 | Himmelsbach et al. |
| 2004/0171836 A1 | 9/2004 | Fujino et al. |
| 2004/0180925 A1 | 9/2004 | Matsuno et al. |
| 2004/0259903 A1 | 12/2004 | Boehringer et al. |
| 2004/0266806 A1 | 12/2004 | Sanghvi et al. |
| 2005/0020574 A1 | 1/2005 | Hauel et al. |
| 2005/0026921 A1 | 2/2005 | Eckhardt et al. |
| 2005/0027012 A1 | 2/2005 | Kohlrausch |
| 2005/0032804 A1 | 2/2005 | Cypes et al. |
| 2005/0065145 A1 | 3/2005 | Cao et al. |
| 2005/0070562 A1 | 3/2005 | Jones et al. |
| 2005/0070594 A1 | 3/2005 | Kauschke et al. |
| 2005/0097798 A1 | 5/2005 | Evans et al. |
| 2005/0130985 A1 | 6/2005 | Himmelsbach et al. |
| 2005/0143377 A1 | 6/2005 | Himmelsbach et al. |
| 2005/0171093 A1 | 8/2005 | Eckhardt et al. |
| 2005/0187227 A1 | 8/2005 | Himmelsbach et al. |
| 2005/0203095 A1 | 9/2005 | Eckhardt et al. |
| 2005/0234108 A1 | 10/2005 | Himmelsbach et al. |
| 2005/0234235 A1 | 10/2005 | Eckhardt et al. |
| 2005/0239778 A1 | 10/2005 | Konetzki et al. |
| 2005/0244502 A1 | 11/2005 | Mathias et al. |
| 2005/0256310 A1 | 11/2005 | Hulin et al. |
| 2005/0261271 A1 | 11/2005 | Feng et al. |
| 2005/0261352 A1 | 11/2005 | Eckhardt |
| 2005/0266080 A1 | 12/2005 | Desai et al. |
| 2005/0276794 A1 | 12/2005 | Papas et al. |
| 2006/0004074 A1 | 1/2006 | Eckhardt et al. |
| 2006/0034922 A1 | 2/2006 | Cheng et al. |
| 2006/0039968 A1 | 2/2006 | Manikandan et al. |
| 2006/0039974 A1 | 2/2006 | Akiyama et al. |
| 2006/0047125 A1 | 3/2006 | Leonardi et al. |
| 2006/0058323 A1 | 3/2006 | Eckhardt et al. |
| 2006/0063787 A1 | 3/2006 | Yoshikawa et al. |
| 2006/0074058 A1 | 4/2006 | Holmes et al. |
| 2006/0079541 A1 | 4/2006 | Langkopf et al. |
| 2006/0094722 A1 | 5/2006 | Yasuda et al. |
| 2006/0100199 A1 | 5/2006 | Yoshikawa et al. |
| 2006/0106035 A1 | 5/2006 | Hendrix et al. |
| 2006/0111372 A1 | 5/2006 | Hendrix et al. |
| 2006/0111379 A1 | 5/2006 | Guillemont et al. |
| 2006/0134206 A1 | 6/2006 | Iyer et al. |
| 2006/0142310 A1 | 6/2006 | Pfrengle et al. |
| 2006/0154866 A1 | 7/2006 | Chu et al. |
| 2006/0159746 A1 | 7/2006 | Troup et al. |
| 2006/0173056 A1 | 8/2006 | Kitajima et al. |
| 2006/0205711 A1 | 9/2006 | Himmelsbach et al. |
| 2006/0205943 A1 | 9/2006 | Dahanukar et al. |
| 2006/0247226 A1 | 11/2006 | Himmelsbach et al. |
| 2006/0270668 A1 | 11/2006 | Chew et al. |
| 2006/0270701 A1 | 11/2006 | Kroth et al. |
| 2007/0027168 A1 | 2/2007 | Pfrengle et al. |
| 2007/0059797 A1 | 3/2007 | Low et al. |
| 2007/0060530 A1 | 3/2007 | Christopher et al. |
| 2007/0072803 A1 | 3/2007 | Chu et al. |
| 2007/0072810 A1 | 3/2007 | Asakawa |
| 2007/0088038 A1 | 4/2007 | Eckhardt et al. |
| 2007/0093659 A1 | 4/2007 | Bonfanti et al. |
| 2007/0142383 A1 | 6/2007 | Eckhardt et al. |
| 2007/0173452 A1 | 7/2007 | DiMarchi et al. |
| 2007/0185091 A1 | 8/2007 | Himmelsbach et al. |
| 2007/0196472 A1 | 8/2007 | Kiel et al. |
| 2007/0197522 A1 | 8/2007 | Edwards et al. |
| 2007/0197552 A1 | 8/2007 | Carr |
| 2007/0219178 A1 | 9/2007 | Muramoto |
| 2007/0254944 A1 | 11/2007 | Hughes |
| 2007/0259900 A1 | 11/2007 | Sieger et al. |
| 2007/0259925 A1 | 11/2007 | Boehringer et al. |
| 2007/0259927 A1 | 11/2007 | Suzuki et al. |
| 2007/0265349 A1 | 11/2007 | Rapin et al. |
| 2007/0281940 A1 | 12/2007 | Dugi et al. |
| 2007/0299076 A1 | 12/2007 | Piotrowski et al. |
| 2008/0014270 A1 | 1/2008 | Harada |
| 2008/0039427 A1 | 2/2008 | Ray et al. |
| 2008/0107731 A1 | 5/2008 | Kohlrausch et al. |
| 2008/0108816 A1 | 5/2008 | Zutter |
| 2008/0234291 A1 | 9/2008 | Francois et al. |
| 2008/0249089 A1 | 10/2008 | Himmelsbach et al. |
| 2008/0255159 A1 | 10/2008 | Himmelsbach et al. |
| 2008/0312243 A1 | 12/2008 | Eckhardt et al. |
| 2008/0318922 A1 | 12/2008 | Nakahira et al. |
| 2009/0023920 A1 | 1/2009 | Eckhardt |
| 2009/0088408 A1 | 4/2009 | Meade et al. |
| 2009/0088569 A1 | 4/2009 | Eckhardt et al. |
| 2009/0093457 A1 | 4/2009 | Himmelsbach et al. |
| 2009/0131432 A1 | 5/2009 | Himmelsbach et al. |
| 2009/0136596 A1 | 5/2009 | Munson et al. |
| 2009/0137801 A1 | 5/2009 | Himmelsbach et al. |
| 2009/0149483 A1 | 6/2009 | Nakahira et al. |
| 2009/0186086 A1 | 7/2009 | Shankar et al. |
| 2009/0192314 A1 | 7/2009 | Pfrengle et al. |
| 2009/0297470 A1 | 12/2009 | Franz |
| 2009/0301105 A1 | 12/2009 | Loerting |
| 2009/0325926 A1 | 12/2009 | Himmelsbach |
| 2010/0074950 A1 | 3/2010 | Sesha |
| 2010/0092551 A1 | 4/2010 | Nakamura et al. |
| 2010/0173916 A1 | 7/2010 | Himmelsbach et al. |
| 2010/0179191 A1 | 7/2010 | Himmelsbach et al. |
| 2010/0183531 A1 | 7/2010 | Johncock et al. |
| 2010/0204250 A1 | 8/2010 | Himmelsbach et al. |
| 2010/0209506 A1 | 8/2010 | Eisenreich |
| 2010/0310664 A1 | 12/2010 | Watson et al. |
| 2010/0317575 A1 | 12/2010 | Pinnetti et al. |
| 2010/0330177 A1 | 12/2010 | Pourkavoos |
| 2011/0009391 A1 | 1/2011 | Braun et al. |
| 2011/0028391 A1 | 2/2011 | Holst et al. |
| 2011/0046076 A1 | 2/2011 | Eickelmann et al. |
| 2011/0065731 A1 | 3/2011 | Dugi et al. |
| 2011/0092510 A1 | 4/2011 | Klein et al. |
| 2011/0098240 A1 | 4/2011 | Dugi et al. |
| 2011/0112069 A1 | 5/2011 | Himmelsbach et al. |
| 2011/0144083 A1 | 6/2011 | Himmelsbach et al. |
| 2011/0144095 A1 | 6/2011 | Himmelsbach et al. |
| 2011/0190322 A1 | 8/2011 | Klein et al. |
| 2011/0195917 A1 | 8/2011 | Dugi et al. |
| 2011/0206766 A1 | 8/2011 | Friedl et al. |
| 2011/0212982 A1 | 9/2011 | Takeda |
| 2011/0263493 A1 | 10/2011 | Dugi et al. |
| 2011/0263617 A1 | 10/2011 | Mark et al. |
| 2011/0275561 A1 | 11/2011 | Graefe-Mody et al. |
| 2011/0301182 A1 | 12/2011 | Dugi |
| 2012/0003313 A1 | 1/2012 | Kohlrausch et al. |
| 2012/0035158 A1 | 2/2012 | Himmelsbach et al. |
| 2012/0040982 A1 | 2/2012 | Himmelsbach et al. |
| 2012/0053173 A1 | 3/2012 | Banno et al. |
| 2012/0094894 A1 | 4/2012 | Graefe-Mody et al. |
| 2012/0107398 A1 | 5/2012 | Schneider et al. |
| 2012/0121530 A1 | 5/2012 | Klein et al. |
| 2012/0122776 A1 | 5/2012 | Graefe-Mody et al. |
| 2012/0129874 A1 | 5/2012 | Sieger et al. |
| 2012/0142712 A1 | 6/2012 | Pfrengle et al. |
| 2012/0165251 A1 | 6/2012 | Klein et al. |
| 2012/0208831 A1 | 8/2012 | Himmelsbach et al. |
| 2012/0219622 A1 | 8/2012 | Kohlrausch et al. |
| 2012/0219623 A1 | 8/2012 | Meinicke |
| 2012/0232004 A1 | 9/2012 | Bachovchin et al. |
| 2012/0252782 A1 | 10/2012 | Himmelsbach et al. |
| 2012/0252783 A1 | 10/2012 | Himmelsbach et al. |
| 2012/0296091 A1 | 11/2012 | Sieger et al. |
| 2013/0064887 A1 | 3/2013 | Ito et al. |
| 2013/0086076 A1 | 4/2013 | Pandit et al. |

(56) References Cited

U.S. PATENT DOCUMENTS

| | | | |
|---|---|---|---|
| 2013/0122089 A1 | 5/2013 | Kohlrausch et al. |
| 2013/0172244 A1 | 7/2013 | Klein et al. |
| 2013/0184204 A1 | 7/2013 | Pfrengle et al. |
| 2013/0196898 A1 | 8/2013 | Dugi et al. |
| 2013/0236543 A1 | 9/2013 | Ito et al. |
| 2013/0303554 A1 | 11/2013 | Klein et al. |
| 2013/0310398 A1 | 11/2013 | Mark et al. |
| 2013/0315975 A1 | 11/2013 | Klein et al. |
| 2013/0317046 A1 | 11/2013 | Johansen |
| 2013/0324463 A1 | 12/2013 | Klein et al. |
| 2014/0100236 A1 | 4/2014 | Busl et al. |
| 2014/0274889 A1 | 9/2014 | Johansen et al. |
| 2014/0315832 A1 | 10/2014 | Broedl et al. |
| 2014/0343014 A1 | 11/2014 | Klein et al. |
| 2014/0371243 A1 | 12/2014 | Klein et al. |
| 2015/0196565 A1 | 7/2015 | Klein et al. |
| 2015/0246045 A1 | 9/2015 | Klein et al. |
| 2015/0265538 A1 | 9/2015 | Balthes et al. |
| 2016/0058769 A1 | 3/2016 | Graefe-Mody et al. |
| 2016/0082011 A1 | 3/2016 | Klein et al. |
| 2016/0106677 A1 | 4/2016 | Boeck et al. |
| 2016/0310435 A1 | 10/2016 | Friedl et al. |
| 2017/0020868 A1 | 1/2017 | Dugi et al. |

FOREIGN PATENT DOCUMENTS

| | | |
|---|---|---|
| CA | 1123437 A1 | 5/1982 |
| CA | 2136288 A1 | 5/1995 |
| CA | 2375779 | 5/2000 |
| CA | 2418656 A1 | 2/2002 |
| CA | 2435730 A1 | 9/2002 |
| CA | 2496249 A1 | 3/2004 |
| CA | 2496325 A1 | 3/2004 |
| CA | 2498423 A1 | 4/2004 |
| CA | 2505389 A1 | 5/2004 |
| CA | 2508233 A1 | 6/2004 |
| CA | 2529729 A1 | 12/2004 |
| CA | 2543074 A1 | 6/2005 |
| CA | 2555050 A1 | 9/2005 |
| CA | 2556064 A1 | 9/2005 |
| CA | 2558067 A1 | 10/2005 |
| CA | 2558446 A1 | 10/2005 |
| CA | 2561210 A1 | 10/2005 |
| CA | 2562859 A1 | 11/2005 |
| CA | 2576294 A1 | 3/2006 |
| CA | 2590912 A1 | 6/2006 |
| CA | 2599419 A1 | 11/2006 |
| CA | 2651019 A1 | 11/2007 |
| CA | 2651089 A1 | 11/2007 |
| CA | 2720450 A1 | 10/2009 |
| CN | 101234105 A | 8/2008 |
| DE | 2205815 A1 | 8/1973 |
| DE | 2758025 A1 | 7/1979 |
| DE | 19705233 A1 | 8/1998 |
| DE | 10109021 A1 | 9/2002 |
| DE | 10117803 A1 | 10/2002 |
| DE | 10238243 A1 | 3/2004 |
| DE | 102004019540 A1 | 11/2005 |
| DE | 102004024454 A1 | 12/2005 |
| DE | 102004044221 A1 | 3/2006 |
| DE | 102004054054 A1 | 5/2006 |
| EA | 201300121 | 10/2009 |
| EP | 0023032 A1 | 1/1981 |
| EP | 0149578 A2 | 7/1985 |
| EP | 0189941 A2 | 8/1986 |
| EP | 0223403 A2 | 5/1987 |
| EP | 0237608 A1 | 9/1987 |
| EP | 0248634 A2 | 12/1987 |
| EP | 0342675 A2 | 11/1989 |
| EP | 0389282 A2 | 9/1990 |
| EP | 0399285 A1 | 11/1990 |
| EP | 0400974 A2 | 12/1990 |
| EP | 409281 A1 | 1/1991 |
| EP | 0412358 A1 | 2/1991 |
| EP | 443983 A1 | 8/1991 |
| EP | 0475482 A1 | 3/1992 |
| EP | 0524482 A1 | 1/1993 |
| EP | 0638567 A1 | 2/1995 |
| EP | 0657454 A1 | 6/1995 |
| EP | 0775704 A1 | 5/1997 |
| EP | 0950658 A1 | 10/1999 |
| EP | 1054012 A1 | 11/2000 |
| EP | 1066265 A1 | 1/2001 |
| EP | 1310245 A1 | 5/2003 |
| EP | 1333033 | 8/2003 |
| EP | 1338595 A2 | 8/2003 |
| EP | 1406873 A2 | 4/2004 |
| EP | 1500403 A1 | 1/2005 |
| EP | 1514552 A1 | 3/2005 |
| EP | 1523994 A1 | 4/2005 |
| EP | 1535906 A1 | 6/2005 |
| EP | 1537880 A1 | 6/2005 |
| EP | 1557165 A1 | 7/2005 |
| EP | 1586571 A1 | 10/2005 |
| EP | 1743655 A1 | 1/2007 |
| EP | 1760076 | 3/2007 |
| EP | 1829877 A1 | 9/2007 |
| EP | 1852108 A1 | 11/2007 |
| EP | 1897892 A2 | 3/2008 |
| EP | 2143443 A1 | 1/2010 |
| EP | 2166007 A1 | 3/2010 |
| ES | 385302 A1 | 4/1973 |
| ES | 2256797 T3 | 7/2006 |
| ES | 2263057 T3 | 12/2006 |
| FR | 2707641 A1 | 1/1995 |
| GB | 2084580 A | 4/1982 |
| HU | 3003243 | 5/1990 |
| HU | 9902308 A2 | 7/2000 |
| JP | S374895 A | 6/1962 |
| JP | 61030567 | 2/1986 |
| JP | 770120 | 3/1995 |
| JP | 8333339 | 12/1996 |
| JP | 11193270 | 7/1999 |
| JP | 2000502684 A | 3/2000 |
| JP | 2001213770 A | 8/2001 |
| JP | 2001278812 A | 10/2001 |
| JP | 2001292388 A | 10/2001 |
| JP | 2002348279 A | 12/2002 |
| JP | 2003286287 A | 10/2003 |
| JP | 2003300977 A | 10/2003 |
| JP | 2004161749 A | 6/2004 |
| JP | 2004196824 A | 7/2004 |
| JP | 2004250336 A | 9/2004 |
| JP | 2005511636 A | 4/2005 |
| JP | 2005519059 A | 6/2005 |
| JP | 2006503013 A | 1/2006 |
| JP | 2006045156 A | 2/2006 |
| JP | 2006137678 A | 6/2006 |
| JP | 2007510059 A | 4/2007 |
| JP | 2007522251 A | 8/2007 |
| JP | 2007531780 A | 11/2007 |
| JP | 2008513390 A | 5/2008 |
| JP | 2008536881 A | 9/2008 |
| JP | 2010500326 A | 1/2010 |
| JP | 2010053576 A | 3/2010 |
| JP | 2010070576 A | 4/2010 |
| JP | 2010524580 A | 7/2010 |
| JP | 2010535850 A | 11/2010 |
| JP | 2010536734 A | 12/2010 |
| JP | 2011088838 A | 5/2011 |
| JP | 2011529945 A | 12/2011 |
| JP | 2012502081 A | 1/2012 |
| JP | 2012505859 A | 3/2012 |
| KR | 20070111099 A | 11/2007 |
| WO | 8706941 A1 | 11/1987 |
| WO | 199107945 A1 | 6/1991 |
| WO | 199205175 A1 | 4/1992 |
| WO | 199219227 A2 | 11/1992 |
| WO | 199402150 A1 | 2/1994 |
| WO | 199403456 A1 | 2/1994 |
| WO | 9532178 A1 | 11/1995 |
| WO | 199609045 A1 | 3/1996 |
| WO | 199611917 A1 | 4/1996 |
| WO | 199636638 A1 | 11/1996 |

(56) References Cited

FOREIGN PATENT DOCUMENTS

| | | |
|---|---|---|
| WO | 199718814 A1 | 5/1997 |
| WO | 199723447 A1 | 7/1997 |
| WO | 199723473 A1 | 7/1997 |
| WO | 199746526 A1 | 12/1997 |
| WO | 1998007725 | 2/1998 |
| WO | 199811893 | 3/1998 |
| WO | 9818770 A1 | 5/1998 |
| WO | 199822464 A1 | 5/1998 |
| WO | 199828007 A1 | 7/1998 |
| WO | 199840069 A2 | 9/1998 |
| WO | 1998046082 A1 | 10/1998 |
| WO | 199856406 A1 | 12/1998 |
| WO | 199929695 A1 | 6/1999 |
| WO | 1999038501 A2 | 8/1999 |
| WO | 199950248 A1 | 10/1999 |
| WO | 199956561 A1 | 11/1999 |
| WO | 199967279 A1 | 12/1999 |
| WO | 200012064 A1 | 3/2000 |
| WO | 200072873 | 5/2000 |
| WO | 200034241 A1 | 6/2000 |
| WO | 0069464 A1 | 11/2000 |
| WO | 0072799 A2 | 12/2000 |
| WO | 0078735 A1 | 12/2000 |
| WO | 200072973 A1 | 12/2000 |
| WO | 200073307 A2 | 12/2000 |
| WO | 200107441 A1 | 2/2001 |
| WO | 2001032158 A2 | 5/2001 |
| WO | 2001040180 A2 | 6/2001 |
| WO | 200152825 | 7/2001 |
| WO | 200152852 A1 | 7/2001 |
| WO | 2001047514 A1 | 7/2001 |
| WO | 2001051919 | 7/2001 |
| WO | 2001066548 A1 | 9/2001 |
| WO | 2001068603 | 9/2001 |
| WO | 2001068646 A1 | 9/2001 |
| WO | 200177110 A1 | 10/2001 |
| WO | 2001072290 A2 | 10/2001 |
| WO | 200196301 A1 | 12/2001 |
| WO | 200197808 A1 | 12/2001 |
| WO | 200202560 A2 | 1/2002 |
| WO | 200214271 A1 | 2/2002 |
| WO | 200224698 A1 | 3/2002 |
| WO | 2002053516 A2 | 7/2002 |
| WO | 2002068420 A1 | 9/2002 |
| WO | 2003000241 A2 | 1/2003 |
| WO | 2003000250 | 1/2003 |
| WO | 2003002531 A2 | 1/2003 |
| WO | 2003002553 A2 | 1/2003 |
| WO | 2003004496 A1 | 1/2003 |
| WO | 2003006425 A2 | 1/2003 |
| WO | 2003024965 A2 | 3/2003 |
| WO | 2003033686 A2 | 4/2003 |
| WO | 2003034944 A1 | 5/2003 |
| WO | 2003035177 A2 | 5/2003 |
| WO | 2003037327 A1 | 5/2003 |
| WO | 2003053929 A1 | 7/2003 |
| WO | 2003055881 A1 | 7/2003 |
| WO | 2003057200 A2 | 7/2003 |
| WO | 2003059327 | 7/2003 |
| WO | 2003064454 A1 | 8/2003 |
| WO | 2003074500 A2 | 9/2003 |
| WO | 2003088900 A2 | 10/2003 |
| WO | 2003094909 A2 | 11/2003 |
| WO | 2003099279 A1 | 12/2003 |
| WO | 2003099836 A1 | 12/2003 |
| WO | 2003104229 A1 | 12/2003 |
| WO | 2003106428 A1 | 12/2003 |
| WO | 2004002924 A1 | 1/2004 |
| WO | 2004011416 A1 | 2/2004 |
| WO | 2004016587 A1 | 2/2004 |
| WO | 2000003735 | 3/2004 |
| WO | 2004018467 A2 | 3/2004 |
| WO | 2004018468 A2 | 3/2004 |
| WO | 2004018469 A1 | 3/2004 |
| WO | 2004028524 A1 | 4/2004 |
| WO | 2004033455 A1 | 4/2004 |
| WO | 2004035575 A1 | 4/2004 |
| WO | 2004037169 A2 | 5/2004 |
| WO | 2004041820 A1 | 5/2004 |
| WO | 2004043940 | 5/2004 |
| WO | 2004046148 A1 | 6/2004 |
| WO | 2004048379 A1 | 6/2004 |
| WO | 2004050658 A1 | 6/2004 |
| WO | 2004052362 A1 | 6/2004 |
| WO | 2004058233 A1 | 7/2004 |
| WO | 2004062689 A1 | 7/2004 |
| WO | 2004065380 A1 | 8/2004 |
| WO | 2004074246 A2 | 9/2004 |
| WO | 2004081006 A1 | 9/2004 |
| WO | 2004082402 A1 | 9/2004 |
| WO | 2004096806 A1 | 11/2004 |
| WO | 2004096811 A1 | 11/2004 |
| WO | 2004106279 A2 | 12/2004 |
| WO | 2004108730 A1 | 12/2004 |
| WO | 2004111051 A1 | 12/2004 |
| WO | 2005000846 A1 | 1/2005 |
| WO | 2005000848 A1 | 1/2005 |
| WO | 2005007137 A2 | 1/2005 |
| WO | 2005007647 A1 | 1/2005 |
| WO | 2005007658 A2 | 1/2005 |
| WO | 2005012288 A1 | 2/2005 |
| WO | 2005016365 | 2/2005 |
| WO | 2005023179 A2 | 3/2005 |
| WO | 2005049022 A2 | 6/2005 |
| WO | 2005051950 A1 | 6/2005 |
| WO | 2005058901 A1 | 6/2005 |
| WO | 2005061489 A1 | 7/2005 |
| WO | 2005063750 A1 | 7/2005 |
| WO | 2005075410 A1 | 8/2005 |
| WO | 2005082906 A1 | 9/2005 |
| WO | 2005085246 A1 | 9/2005 |
| WO | 2005092870 A1 | 10/2005 |
| WO | 2005092877 A1 | 10/2005 |
| WO | 2005095343 A1 | 10/2005 |
| WO | 2005095381 A1 | 10/2005 |
| WO | 2005097798 A | 10/2005 |
| WO | 2005097798 A1 | 10/2005 |
| WO | 2005116000 A1 | 12/2005 |
| WO | 2005116014 A1 | 12/2005 |
| WO | 2005117861 A1 | 12/2005 |
| WO | 2005117948 A1 | 12/2005 |
| WO | 2006005613 A1 | 1/2006 |
| WO | 2006027204 A1 | 3/2006 |
| WO | 2006029577 A1 | 3/2006 |
| WO | 2006029769 A1 | 3/2006 |
| WO | 2006036664 A1 | 4/2006 |
| WO | 2006040625 A1 | 4/2006 |
| WO | 2006041976 A1 | 4/2006 |
| WO | 2006047248 A1 | 5/2006 |
| WO | 2006048209 A1 | 5/2006 |
| WO | 2006048427 A1 | 5/2006 |
| WO | 2006068163 A1 | 6/2006 |
| WO | 2006071078 A1 | 7/2006 |
| WO | 2006076231 A2 | 7/2006 |
| WO | 2006078593 A2 | 7/2006 |
| WO | 2006083491 A2 | 8/2006 |
| WO | 2006116157 | 11/2006 |
| WO | 2006135693 A2 | 12/2006 |
| WO | 2006137085 A1 | 12/2006 |
| WO | 2007007173 A2 | 1/2007 |
| WO | 2007014886 A1 | 2/2007 |
| WO | 2007014895 A2 | 2/2007 |
| WO | 2007017423 A1 | 2/2007 |
| WO | 2007033350 A1 | 3/2007 |
| WO | 2007035355 A2 | 3/2007 |
| WO | 2007035665 A1 | 3/2007 |
| WO | 2007038979 A1 | 4/2007 |
| WO | 2007041053 A2 | 4/2007 |
| WO | 2007050485 A2 | 5/2007 |
| WO | 2007071738 | 6/2007 |
| WO | 2007072083 A1 | 6/2007 |
| WO | 2007078726 A2 | 7/2007 |
| WO | 2007093610 A1 | 8/2007 |
| WO | 2007099345 A1 | 9/2007 |

(56) References Cited

FOREIGN PATENT DOCUMENTS

| | | |
|---|---|---|
| WO | 2007120702 A2 | 10/2007 |
| WO | 2007120936 A2 | 10/2007 |
| WO | 2007128721 A | 11/2007 |
| WO | 2007128724 A1 | 11/2007 |
| WO | 2007128761 A2 | 11/2007 |
| WO | 2007135196 A2 | 11/2007 |
| WO | 2007136151 A1 | 11/2007 |
| WO | 2007137107 A2 | 11/2007 |
| WO | 2007147185 A1 | 12/2007 |
| WO | 2007148185 A2 | 12/2007 |
| WO | 2007149797 A2 | 12/2007 |
| WO | 2003057245 | 1/2008 |
| WO | 2008005569 A2 | 1/2008 |
| WO | 2008005576 A1 | 1/2008 |
| WO | 2008017670 | 2/2008 |
| WO | 2008022267 A2 | 2/2008 |
| WO | 2008055870 A1 | 5/2008 |
| WO | 2008055940 A2 | 5/2008 |
| WO | 2008070692 A2 | 6/2008 |
| WO | 2008077639 A1 | 7/2008 |
| WO | 2008081205 A1 | 7/2008 |
| WO | 2008083238 A2 | 7/2008 |
| WO | 2008087198 A1 | 7/2008 |
| WO | 2008093878 A1 | 8/2008 |
| WO | 2008093882 A1 | 8/2008 |
| WO | 2008097180 A1 | 8/2008 |
| WO | 2008113000 A1 | 9/2008 |
| WO | 2008130998 A2 | 10/2008 |
| WO | 2008131149 A2 | 10/2008 |
| WO | 2008137435 A1 | 11/2008 |
| WO | 2009011451 A | 1/2009 |
| WO | 2009022007 | 2/2009 |
| WO | 2009022007 A1 | 2/2009 |
| WO | 2009022008 A1 | 2/2009 |
| WO | 2009022009 A1 | 2/2009 |
| WO | 2009022010 A1 | 2/2009 |
| WO | 2009024542 A2 | 2/2009 |
| WO | 2009063072 A2 | 5/2009 |
| WO | 2009091082 A1 | 7/2009 |
| WO | 2009099734 A1 | 8/2009 |
| WO | 2009111200 A1 | 9/2009 |
| WO | 2009112691 A2 | 9/2009 |
| WO | 2009121945 A2 | 10/2009 |
| WO | 2009123992 A1 | 10/2009 |
| WO | 2009147125 A1 | 12/2009 |
| WO | 201092124 | 2/2010 |
| WO | 2010015664 A1 | 2/2010 |
| WO | 2010018217 A2 | 2/2010 |
| WO | 2010029089 A2 | 3/2010 |
| WO | 2010043688 A1 | 4/2010 |
| WO | 2010045656 A2 | 4/2010 |
| WO | 2010072776 A1 | 7/2010 |
| WO | 2010079197 A1 | 7/2010 |
| WO | 2010086411 A1 | 8/2010 |
| WO | 2010092124 A1 | 8/2010 |
| WO | 2010092125 A1 | 8/2010 |
| WO | 2010092163 A2 | 8/2010 |
| WO | 2010096384 A2 | 8/2010 |
| WO | 2010106457 A2 | 9/2010 |
| WO | 2010140111 A1 | 12/2010 |
| WO | 2010147768 A1 | 12/2010 |
| WO | 2011011541 A1 | 1/2011 |
| WO | 2007033266 | 4/2011 |
| WO | 2011039337 A1 | 4/2011 |
| WO | 2011039367 A2 | 4/2011 |
| WO | 2011064352 A1 | 6/2011 |
| WO | 2011109333 | 9/2011 |
| WO | 2011113947 A1 | 9/2011 |
| WO | 2011138380 A1 | 11/2011 |
| WO | 2011138421 A1 | 11/2011 |
| WO | 2011154496 A1 | 12/2011 |
| WO | 2011161161 A1 | 12/2011 |
| WO | 2011163206 A2 | 12/2011 |
| WO | 2012031124 A2 | 3/2012 |
| WO | 2012065993 A1 | 5/2012 |
| WO | 2012088682 A1 | 7/2012 |
| WO | 2012089127 A1 | 7/2012 |
| WO | 2012106303 A1 | 8/2012 |
| WO | 2012120040 A1 | 9/2012 |
| WO | 2003061688 | 4/2013 |
| WO | 2013098372 A1 | 7/2013 |
| WO | 2013103629 A1 | 7/2013 |
| WO | 2013131967 A1 | 9/2013 |
| WO | 2013171167 A1 | 11/2013 |
| WO | 2013174768 A1 | 11/2013 |
| WO | 2013179307 A2 | 12/2013 |
| WO | 2014140284 A1 | 9/2014 |
| WO | 2014170383 A1 | 10/2014 |

OTHER PUBLICATIONS

Schillinger, M. et al., "Restenosis after percutaneous angioplasty: the role of vascular inflammation." Vascular Health and Risk Management, 2005, vol. 1, No. 1, pp. 73-78.

Schmidt, D. et al., "Fibromatosis of Infancy and Childhood Histology, Ultrastructure and Clinicopathologic Correlation." Zeitschrift für Kinderchirurgie, 1985, vol. 40, No. 1, pp. 40-46.

Schnapp, G. et al., "Analysis of Binding Kinetics and Thermodynamics of DPP-4 Inhibitors and their Relationship to Structure." 23rd PSDI, Protein Structure Determination in Industry, Tegernsee, Germany, Nov. 8-10, 2015.

Schnapp, G. et al., "Analysis of binding kinetics and thermodynamics of DPPIV Inhibitors and their relationship to structure." International Workshop: The aspect of time in drug design, Schloss Rauischholzhausen, Marburg, Germany, Mar. 24-27, 2014.

Schnapp, G. et al., "Comparative Enzyme Kinetic Analysis of the Launched DPP-4 Inhibitors." American Diabetes Association 74th Scientific Sessions, Poster 1048-P, 2014.

Schnapp, G. et al., "Comparative Enzyme Kinetic Analysis of the Launched DPP-4 Inhibitors." American Diabetes Association, Abstract 1048-P, 2014.

Schurmann, C. et al., "The Dipeptidyl Peptidase-4 Inhibitor Linagliptin Attenuates Inflammation and Accelerates Epithelialization in Wounds of Diabetic ob/ob Mice." The Journal of Pharmacology and Experimental Therapeutics, 2012, vol. 342, No. 1, pp. 71-80.

Schwartz, M. S. et al., "Type 2 Diabetes Mellitus in Childhood: Obesity and Insulin Resistance". JAOA Review Article, vol. 108, No. 9, Sep. 2008, p. 518.

Scientific Discussion, EMEA, Pramipexole, 2005, pp. 1-10.

Scientific Discussion: "Eucreas. Scientific discussion". Online Oct. 2007, p. 1-27, URL:http://www.emea.europa.eu/humandocs/PDFs/EPAR/eucreas/H-807-en6.pdf. see point 2. quality aspects pp. 2-4. (EMEA).

Sedo, A. et al; "Dipeptidyl peptidase IV activity and/or structure homologs: Contributing factors in the pathogenesis of rheumatoid arthritis?" Arthritis Research & Therapy 2005, vol. 7, pp. 253-269.

Shanks, N. et al., Are animal models predictive for humans?, PEHM, Philosophy, Ethics, and Humanaities in Medicine, 4(2), 2009, 1-20.

Sharkovska, Y., et al., "DPP-4 Inhibition with Linagliptin Delays the Progression of Diabetic Nephropathy in db/db Mice." 48th EASD Annual Meeting, Berlin, Abstract 35, Oct. 2012. <http://www.abstractsonline.com/Plan/ViewAbstract.aspx?sKey=0b0017b9-9e90-4695-b9af-b6870e96a921&cKey=8eff47ae-db49-4c36-a142-848ac068c405&mKey=2dbfcaf7-1539-42d5-8dda-0a94abb089e8>.

Sheperd, Todd M. et al., "Efective management of obesity." The Journal of Family Practice, 2003, vol. 52, No. 1, pp. 34-42.

Shintani, Maki, et al., "Insulin Resistance and Genes" Circulatory Sciences (1997) vol. 17, No. 12 pp. 1186-1188.

Shu, L. et al., "Decreased TCF7L2 protein levels in type 2 diabetes mellitus correlate with downregulation of GIP- and GLP-1 receptors and impaired beta-cell function." Human Molecular Genetics, 2009, vol. 18, No. 13, pp. 2388-2399.

Shu, L. et al., "Transcription Factor 7-Like 2 Regulates B-Cell Survival and Function in Human Pancreatic Islets." Diabetes, 2008, vol. 57, pp. 645-653.

(56) References Cited

OTHER PUBLICATIONS

Silverman, G. et al., "Handbook of Grignard Reagents." 1996, Retrieved online: <http://books.google.com/books?id=82CaxfY-uNkC&printsec=frontcover &dq=intitle:Handbook+intitle:of+intitle:Grignard+intitle:Reagents &hl=en&sa=X&ei=g06GU5SdOKngsATphYCgCg &ved=0CDYQ6AEwAA#v=onepage&q&f=false>.

Singhal, D. et al., "Drug polymorphism and dosage form design: a practical perspective." Advanced Drug Delivery Reviews, 2004, vol. 56, pp. 335-347.

Sortino, M.A. et al., "Linagliptin: a thorough characterization beyond its clinical efficacy." Frontiers in Endocrinology, 2013, vol. 4, Article 16, pp. 1-9.

St. John Providence Health Center, "Preventing Obesity in Children and Teens." Retrieved from internet on Aug. 22, 2013, http://www.stjohnprovidence.org/Health I nfoLib/swarticle.aspx?type=85&id=P07863.

Stahl, P.H., "Handbook of Pharmaceutical Salts" C.G. Wermuth, Wiley-VCH, 2002, pp. 1-374.

Standl, E. et al., "Diabetes and the Heart." Diabetes Guidelines (DDG), 2002, pp. 1-25.

Sulkin, T.V. et al., "Contraindications to Metformin Therapy in Patients With NIDDM." Diabetes Care, 1997, vol. 20, No. 6, pp. 925-928.

Sune Negre, J. M. "New Galenic Contributions to Administration Forms". Continued Training for Hospital Pharmacists 3.2., (Publication date unavailable), Retrieved from internet on Feb. 23, 2011, http://www.ub.es/legmh/capitols/sunyenegre.pdf.

Suzuki, Y. et al., "Carbon-Carbon Bond Cleavage of a-Hydroxybenzylheteroarenes Catalyzed by Cyanide Ion: Retro-Benzoin Condensation Affords Ketones and Heteroarenes and Benzyl Migration Affords Benzylheteroarenes and Arenecarbaldehydes." Chemical Pharmaceutical Bulletin, 1998, vol. 46(2), pp. 199-206.

Tadayyon, M. et al., "Insulin sensitisation in the treatment of Type 2 diabetes." Expert Opinion Investigative Drugs, 2003, vol. 12, No. 3, pp. 307-324.

Takai, S. et al., "Significance of Vascular Dipeptidyl Peptidase-4 Inhibition on Vascular Protection in Zucker Diabetic Fatty Rats." Journal of Pharmacological Sciences, 2014, vol. 125, pp. 386-393.

Takeda Press Release: "Voglibose (BASEN) for the prevention of type 2 diabetes mellitus: A Randomized, Double-blind Trial in Japanese Subjects with Impaired Glucose Tolerance." 2008, Retrieved online Jul. 6, 2015. https://www.takeda.com/news/2008/20080526_3621.html.

Tamm, E, et al., "Double-blind study comparing the immunogenicity of a licensed DTwPHib-CRM197 conjugate vaccine (Quattvaxem TM) with three investigational, liquid formulations using lower doses of Hib-CRM197 conjugate". Science Direct, Vaccine, Feb. 2005, vol. 23, No. 14, p. 1715-1719.

Tanaka, S.. et al; "Suppression of Arthritis by the Inhibitors of Dipeptidyl Peptidase IV," In. J. Immunopharmac., vol. 19, No. 1, pp. 15-24, 1997.

Targher, G. et al., "Prevalence of Nonalcoholic Fatty Liver Disease and Its Association With Cardiovascular Disease Among Type 2 Diabetic Patients." Diabetes Care, 2007, vol. 30, No. 5, pp. 1212-1218.

Taskinen, M.-R. et al., "Safety and efficacy of linagliptin as add-on therapy to metformin in patients with type 2 diabetes: a randomized, double-blind, placebo-controlled study." Diabetes, Obesity and Metabolism, 2011, vol. 13, pp. 65-74.

Third Party Observation for application No. EP20070728655, May 13, 2013.

Thomas, L. et al, "BI 1356, a novel and selective xanthine beased DPP-IV inhibitor, exhibits a superior profile when compared to sitagliptin and vildagliptin." Diabetologia, 2007, vol. 50, No. Suppl. 1, p. S363.

Thomas, L., "Chronic treatment with the Dipeptidyl Peptidase-4 Inhibitor BI 1356[9R)-8-(3-Amino-piperidin-1-yl)-7- but-2-ynyl-3-methyl-1(4-methyl-quinazolin-2-ylmethyl)-3,7-dihydro-purine-2,6-dione] Increases Basal Glucagon-Like Peptide-1 and Improves Glycemic Control in Diabetic Rodent Models" The Journal of Pharmacology and Experimental Therapeutics, Feb. 2009, vol. 328, No. 2, pp. 556-563.

Thomas, Leo et al: "(R)-8-(3-Amino-piperidin-1-yl)-7-but-2-ynyl-3-methyl-1-(4-methyl-quinazolin-2-ylmethyl)-3,7-dihydro-purine-2,6-dione (BI 1356), a Novel Xanthine-Based Dipeptidyl Peptidase 4 Inhibitor, Has a Superior Potency and Longer Duration of Action Compared with Other Dipeptidyl Peptidase-4 Inhibitors." Journal of Pharmacology and Experimental Therapeutics, 2008, vol. 325, No. 1, pp. 175-182.

Thornber, C.W., "Isosterism and Molecular Modification in Drug Design." Chemical Society Reviews, 1979, pp. 563-580.

Tounyoubyou, "Symposium-19: Future Perspectives on Incretion Therapy in Diabetes." 2008, vol. 51, Suppl. 1, p. S-71, S19-2.

Tradjenta, Highlights of Prescribing Information (revised Sep. 2012).

Tribulova, N. et al. "Chronic Disturbances in NO Production Results in Histochemical and Subcellular Alterations of the Rat Heart." Physiol. Res., 2000, vol. 49, No. 1, pp. 77-88.

Tsujihata, et al., "TAK-875, an orally available G protein-Coupled receptor 40/Free fatty acid receptor 1 Agonist, Enhances Glucose Dependent Insulin Secretion and improves both Postprandial and Fasting hyperglycemic in type 2 Diabetic rats", J. Pharm Exp. 2011, vol. 339, No. 1, p. 228-237.

Tsuprykov, O. et al., Linagliptin is as Efficacious as Telmisartan in Preventing Renal Disease Progression in Rats with 5/6 Nephrectomy, 73rd Annual Meeting Science Session, ADA, Chicago, Jun. 2013. <http://www.abstractsonline.com/Plan/ViewAbstract.aspx?sKey=e68ac573-fe45-4c2f-9485-6270854fc10b&cKey=3c387569-04de-4f8c-b025-b358df91ca64&mKey=%7b89918D6D-3018-4EA9-9D4F-711F98A7AE5D%7d>.

Turner, R.C. et al., "Glycemic Control With Diet, Sulfonylurea, Metformin, or Insulin in Patients With Type 2 Diabetes Mellitus Progressive Requirement for Multiple Therapies (UKPDS 49)" The Journal of the American Medical Association, 1999, vol. 281, No. 21, pp. 2005-2012.

U.S. Appl. No. 15/235,575, filed Aug. 12, 2016, Inventor: Klaus Dugi.

Uhlig-Laske, B. et al., "Linagliptin, a Potent and Selective DPP-4 Inhibitior, is Safe and Efficacious in Patients with Inadequately Controlled Type 2 Diabetes Despite Metformin Therapy". 535-P Clinical Therapeutics/New Technology—Pharmacologic Treatment of Diabetes or Its Complications, Posters, vol. 58, Jun. 5, 2009, pA143.

United Healthcare, "Diabetes." Retrieved from internet on Aug. 22, 2013, http://www.uhc.com/source4women/health_topics/diabetesirelatedinformation/dOf0417b073bf11OVgnVCM1000002f1Ob1Oa_.htm.

Van Heek, M. et al., "Ezetimibe, a Potent Cholesterol Absorption Inhibitor, Normalizes Combined Dyslipidemia in Obese Hyperinsulinemic Hamsters." Diabetes, 2001, vol. 50, pp. 1330-1335.

Vichayanrat, A. et al., "Efficacy and safety of voglibose in comparison with acarbose in type 2 diabetic patients." Diabetes Research and Clinical Practice, 2002, vol. 55, pp. 99-103.

Vickers, 71st Scientific Session of the American Diabetes Association, "The DPP-4 inhibitor linagliptin is weight neutral in the DIO rat but inhibits the weight gain of DIO animals withdrawn from exenatide", vol. 60, Jul. 2011.

Villhauer, E.B., "1-[[3-Hydroxy-1-adamantyl)amino]acetyl]-1-cyano-(S)-pyrrolidine: A Potent, Selective, and Orally Bioavailable Dipeptidyl Peptidase IV Inhibitor with Antihyperglycemic Properties" Journal Med. Chem, 2003, 46, p. 2774-2789.

Villhauer, E.B., et al., "1-{2-{5-Cyanopyridin-2-yl)amino}ethylamino}acetyl-1-1(S)-pyrrolidine-carbonitrile: A Potent, Selective, and Orally Bioavailable Dipeptidyl Peptidase IV Inhibitor with Antihyperglycemic Properties". Journal of Medical Chemistry, 2002, vol. 45, No. 12, p. 2362-2365.

Vincent, S.H. et al., "Metabolism and Excretion of the Dipeptidyl Peptidase 4 Inhibitor [14C]Sitagliptin in Humans." Drug Metabolism and Disposition, 2007, vol. 35, No. 4, pp. 533-538.

(56) References Cited

OTHER PUBLICATIONS

Wang, Y. et al., "BI-1356. Dipeptidyl-Peptidase IV Inhibitor, Antidiabetic Agent." Drugs of the Future, 2008, vol. 33, No. 6, pp. 473-477.
Weber, Ann E., "Dipeptidyl Peptidase IV Inhibitors for the Treatment of Diabetes." Journal of Medicinal Chemistry, 2004, vol. 47, pp. 4135-4141.
WebMD, Autoimmune Diseases: What Are They? Who Gets Them? "What Are Autoimmune Disorders?" 2015, pp. 1-3. Retrieved online Jul. 9, 2015. http://www.webmd.com/a-to-z-guides/autoimmune-diseases.
Wertheimer, et al., "Drug Delivery Systems improve pharmaceutical profile and facilitate medication adherence", Adv. Therapy 22: p. 559-577 (2005).
White, John R. Jr., "Dipeptidyl Peptidase-IV Inhibitors: Phamacological Profile and Clinical Use". Clinical Diabetes, Apr. 2008, vol. 26, No. 2, pp. 53-57.
Wikipedia, "Linagliptin" Sep. 12, 2015. <https://en.wikipedia.org/w/index.php?title=Linagliptin&oldid=333469979>.
Wikipedia, Annulation. Jun. 23, 2008, http://en.wikipedia.org/wiki/Annelation.
Williams-Herman, D. et al., "Efficacy and safety of initial combination therapy with sitagliptin and metformin in patients with type 2 diabetes: a 54-week study". Current Medical Research and Opinion, Informa Healthcare, GB, vol. 25, No. 3, Jan. 2009, p. 569-583.
Wirth, D. et al., "Maillard Reaction of Lactose and Fluoxetine Hydrochloride, a Secondary Amine." Journal of Pharmaceutical Sciences, 1998, vol. 87, No. 1, pp. 31-39.
Witteles, R. M. et al., "Dipeptidyl Peptidase 4 Inhibition Increases Myocardial Glucose Uptake in Nonischemic Cardiomyopathy." Journal of Cardiac Failure, 2012, vol. 18, No. 10, pp. 804-809.
Wolff, M.E.: "Burger's Medicinal Chemistry and Drug Discovery" Fifth Edition, vol. 1: Principles and Practice, pp. 975-977, 1994, John Wiley & Sons, Inc.
World Health Organization (WHO). "Addendum 1 to "The use of stems in the selection of International Nonproprietary names (INN) for pharmaceutical substances"" Online Jun. 19, 2007, pp. 1-3, retrieved from URL: http://www.who.int/medicindedocs/index/assoc/s1414e/s1414e.pdf.
X-Ray Diffraction. The United States Pharmacopeia, 2002, USP 25 NF20, p. 2088-2089.
Yale, Jean-Francois, "Oral Antihyperglycemic Agents and Renal Disease: New Agents, New Concepts." Journal of the American Society of Nephrology, 2005, vol. 16, Suppl. 1, pp. S7-S10.
Yamagishi, S. et al., "Pleiotropic Effects of Glucagon-like Peptide-1 (GLP-1)-Based Therapies on Vascular Complications in Diabetes." Current Pharmaceutical Design, 2012, vol. 17, pp. 4379-4385.
Yap, W.S. et al., "Review of management of type 2 diabetes mellitus." Journal of Clinical Pharmacy and Therapeutics, 1998, vol. 23, pp. 457-465.
Yasuda, et al. "E3024 3-but-2-ynyl-5-methyl-2-piperazin-1-y1-3,5-dihydro-4H-imidazol [ 4,5-d]pyridazin-4-one tosylate, is a move, selective and competitive dipeptidyl peptidase-IV inhibitor". European Journal of Pharmacology, vol. 548, No. 1-3, Oct. 24, 2006, p. 181-187. Abstract.
Yasuda, N. et al., "Metformin Causes Reduction of Food Intake and Body Weight Gain and Improvement of Glucose Intolerance in Combination with Dipeptidyl Peptidase IV Inhibitor in Zucker fa/fa Rats." The Journal of Pharmacology and Experimental Therapeutics, 2004, vol. 310, No. 2, pp. 614-619.
Yokoyama< "Prevalence of albumineria and renal insufficiency and associated clinical factors in type 2 diabetes: the Japan Diabetes clinical data Management study(JDDM15)" Nephrol Dial Transplant (2009) 24: 1212-1219 Advance Access Pub 2008.
Yoshikawa, Seiji et al.: Chemical Abstract of Japanese Patent No. WO 2003/104229 Preparation of purinone derivatives as dipeptidylpeptidase IV (DPP-IV) inhibitors, 2003.
Yoshioka, S. et al., "Stability of Drugs and Dosage Forms." Kluwer Academic Publishers, 2002, pp. 30-33.
Youssef, S. et al., "Purines XIV. Reactivity of 8-Promo-3,9-dimethylxanthine Towards Some Nucleophilic Reagents." Journal of Heterocyclic Chemistry, 1998, vol. 35, pp. 949-954.
Zander, M. et al., "Additive Glucose-Lowering Effects of Glucagon-Like Peptide-1 and Metformin in Type 2 Diabetes." Diabetes Care, 2001, vol. 24, No. 4, pp. 720-725.
Zeeuw, D. et al., "Albuminuria, a Therapeutic Target for Cardiovascular Protection in Type 2 Diabetic Patients With Nephropathy." Circulation, 2004, vol. 110, No. 8, pp. 921-927.
Zejc, Alfred, et al; "Badania Nad Piperazynowymi Pochodnymi Dwumetyloksantyn" Acta Polon Pharm, XXXV (1976) Nr. 4 pp. 417-421.
Zerilli, T. et al., "Sitagliptin Phosphate: A DPP-4 Inhibitor for the Treatment of Type 2 Diabetes Mellitus." Clinical Therapeutics, 2007, vol. 29, No. 12, pp. 2614-2634.
Zhimei, Xiao et al., "Study progression of oral drugs for treatment of type II diabetes." Drug Evaluation, 2004, vol. 1, No. 2, pp. 138-143.
Zhong, Qing et al; "Glucose-dependent insulinotropic peptide stimulates proliferation and TGF-? release from MG-63 cells," Peptides 24 (2003) 611-616.
Zhu, G. et al., "Stabilization of Proteins Encapsulated in Cylindrical Poly(lactide-co-glycolide) Implants: Mechanism of Stabilization by Basic Additives." Pharmaceutical Research, 2000, vol. 17, No. 3, pp. 351-357.
Zimdahl, H. et al., "Influence of TCF7L2 gene variants on the therapeutic response to the dipeptidylpeptidase-4 inhibitor linagliptin." Diabetologia, 2014, vol. 57, pp. 1869-1875.
Zimmer et al; Synthesis of 8-Substituted Xanthines and their Oxidative Skeleton Rearrangement to 1-Oxo-2,4,7,9-tetraazaspiro[4,5]dec-2-ene-6,8,10-triones; Euripean Journal Organic Chemistry (1999) vol. 9 pp. 2419-2428.
Fantus, George, "Metformin's contraindications: needed for now." Canadian Medical Association Journal, 2005, vol. 173, No. 5, pp. 505-507.
EU Clinical Trial Register, "A multicenter, international, rendomized, parallel group, double-blind, placebo-controlled, cardiovascular safety and renal microvascular outcome study with linagliptin, 5 mg once daily in patients with type 2 diabetes mellitus at high vascular risk." Aug. 19, 2015.
Jibiinkoka-Tenbo, Vision of Otorhinolaryngology, How to use anti-microbial drug in a patient with impairment of renal function, vol. 44, No. 3, 2001, p. 217-220.
Rinsho-Yakuri, Jpn. J. Clin. Pharmacol. Ther. Pharmacokinetics: excretion, 30(3) 1999.
Fiorucci et al. Trends in Molecular Medicine, Targeting farnesoid X receptor for liver and metabolic disorders, 13(7), 2007, p. 298-309.
Morhenn, "Keratinacyte proliferation n wound healing and skin diseases", Immunology Today, vol. 9, Issue 4, 1988, p. 104.
*Boehringer Ingelheim Pharmceuticals, Inc. v. HEC Pharm Co., Ltd.*, et al., No. 15-cv-5982, United States District Court for the District of New Jersey, Dec. 8, 2016.
Karaliede et al, Diabetes Care, Endothelial Factors and Diabetic Nephropathy, 2011, 34, Suppl 2, p. 291-296.
Bundgaard, H. "Design of prodrugs: Bioreversible derivatives for various functional groups and chemical entities". Royal Danish School of Pharmacy, 1985, p. 1-92.
Busso et al., "Circulating CD26 is Negatively Associated with Inflammation in Human and Experimental Arthritis," Am. J. Path., vol. 166, No. 2, Feb. 2005, pp. 433-442.
Byrn, Stephen R. "Solid-State Chemistry of Drugs." Academic Press, 1982, pp. 1-27.
Caira, M.R., "Crystalline polymorphism of organic compounds" Topics in Current Chemistry, Springer, Berlin, vol. 198, 1998, p. 163-208.
Campbell, R. Keith "Rationale for Dipeptidyl Peptidase 4 Inhibitors: A New Class of Oral Agents for the Treatment of Type 2 Diabetes Mellitus." The Annals of Pharmacotherapy, Jan. 2007, vol. 41, pp. 51-60.
Canadian Diabetes Association, "Pharmacologic Management of Type 2 Diabetes." Canadian Journal of Diabetes, 2003, vol. 27, Suppl. 2, pp. S37-S42.

(56) References Cited

OTHER PUBLICATIONS

Canadian Pharmacists Association, Compendium of Pharmaceuticals and Specialties, "Zestril" 2004, pp. 2289-2293.
Cao, C. et al., "The clinical application of linagliptin in Asians." Therapeutics and Clinical Risk Management, 2015, vol. 11, pp. 1409-1419.
Castello, R. et al., "Discoloration of Tablets Containing Amines and Lactose." Journal of Pharmaceutical Sciences, 1962, vol. 51, No. 2, pp. 106-108.
Chan, J.C. et al., "Safety and efficacy of sitagliptin in patients with type 2 diabetes and chronic renal insufficiency." 2008, Diabetes, Obesity and Metabolism, vol. 10, pp. 545-555.
Charbonnel, B. et al., "Efficacy and Safety of the Dipeptidyl Peptidase-4 Inhibitor Sitagliptin Added to Ongoing Metformin Therapy in Patients With Type 2 Diabetes Inadequately Controlled With Metformin Alone." Diabetes Care, 2006, vol. 29, No. 12, pp. 2638-2643.
Chaykovska, L. et al., "Effects of DPP-4 Inhibitors on the Heart in a Rat Model of Uremic Cardiomyopathy." www.plosone.org, 2011, vol. 6, No. 11, p. e27861.
ChemGaroo, "Leaving Group." 1999, Retrieved online: http://www.chemgapedia.de/vsengine/vlu/vsc/en/ch/12/oc/vluorganik/substitution/sn_2/sn 2. vlu/Page/vsc/en/ch/12/oc/substitution/sn_2/abgangsgrupen/abgangsgruppe.vscml.html.
Chemical Abstract. EP412358, 1991:185517, Findeisen.
Chemical Abstract: FR2707641, 1995:543545, Dodey.
Chemical Abstract: No. 211513-37-0—Dalcetrapib. "Propanethioic acid, 2-methyl-,S-(2-[[[1-(2-ethylbutyl)cyclohexyl}carbonyl}amino}pheyl}ester" . Formula: C23 H35 N O2 S. American Chemical Society. Sep. 20, 1998.
Chemical Abstract: No. 875446-37-0—Anacetrapib. "2-Oxazolidinone, 5-[3,5-bis(trifluoromethyl)phenyl]-3[[4'fluoro-2'-methoxy-5'-(1-methylethyl)-4-(trifluoromethyl)[1,1'-biphenyl]-2-yl]methyl]-4-methyl-,(4S,5R)-" Formula: C30 H25 F10 NO3. American Chemical Society, Feb. 28, 2006.
Chemical Abstracts Accession No. 106:95577 Romanenko et al., "Synthesis and Biological Activity of 3-Methyl, 7- or 8-alkyl-7,8dialkyl, heterocyclic, and cyclohexylaminoxanthines," Zaporozh. Med. Institute (1986).
Chemical Abstracts Accession No. 1987:95577: Abstract of Romanenko et al., "Synthesis and biological activity of 3-methyl, 7- or 8-alkyl, 7,8-dialkyl, heterocyclic, and cyclohexylaminoxanthines," Zapoeozh, USSR, Farmatsevtichnii Zhurnal, 1986, (Kiev), vol. 5, 1986, pp. 41-44.
Chemical Abstracts Service, Database Accession No. RN 668270-12-01, 2004, "1H-Purine-2,6-dione, 8-[(3R)-3-amino-1-piperidinyl]-7-(2-butyn-1-yl)-3,7-dihydro-3-methyl-1-[(4-methyl-2-quinazolinyl)methyl]".
Chemistry Review: Tradjenta, "NDA 201280, CMC Director Review Tradjenta (Linagliptin) Tablets." Center for Drug Evaluation and Research, Aug. 9, 2010, Retrieved from the internet on Nov. 1, 2013, http://www.accessdata.fda.gov/drugsatfda_docs/nda/2011/201280Orig1s000ChemR.pdf.
Cheon, et al., Biochemical Pharmacology, "Inhibition of dipeptidyl IV by novel inhibitors with pyrazolidine scaffold", 2005, vol. 70, p. 22-29.
Chiasson, J.-L. et al., "The Synergistic Effect of Miglitol Plus Metformin Combination Therapy in the Treatment of Type 2 Diabetes." Diabetes Care, 2001, vol. 24, No. 6, pp. 989-994.
Chisari, A. et al. "Sulphinyl, Sulphonyl, and Sulphonium Groups as Leaving Groups in Aromatic Nucleophilic Substitutions." Journal of the Chemical Society, Perkin Transactions II, 1982, pp. 957-959.
Chowhan, Z.T. et al., Drug-Excipient Interaction Resulting from Powder Mixing IV: Role of Lubricants and Their Effect on In Vitro Dissolution, Journal of Pharmaceutical Sciences, 1986, vol. 75, No. 6, pp. 542-545.
Clinical Trial NCT00622284 (published online at clinicaltrials.gov on Feb. 22, 2008).

Clinical Trial Protocol, "A Randomised, Double-blind, Placebo-controlled, Five Parallel Groups Study Investigating the Efficacy and Safety of BI 1356 BS." Boehringer Ingelheim Pharmaceuticals, last updated on Jun. 24, 2014.
Clinical Trial, NCT00622284, clinicaltrials.gov, updated Feb. 22, 2008.
Clinical Trials NCT00601250, clinicaltrials.gov, Jan. 25, 2008.
Clinical Trials, No. NCT00309608, "Efficacy and Safety of BI 1356 BS in Combination with Metformin in Patients With type2 Diabetes" 2009, pp. 1-3.
Clinical Trials, No. NCT00622284, "Efficacy and Safety of BI 1356 in combination with metformin in patients with type 2 diabetes" 2012, pp. 1-5.
Clinical Trials. "View of NCT00601250 on Jan. 25, 2008: Efficacy and Safety of BI 1356 vs Placebo added to Metformin Background Therapy in Patients with Type 2 Diabetes" Clinical Trials. Gov Archive, [Online] Jan. 25, 2008 URL:http://clinicaltrials.gov/archive/NCT00601250/2008_01_25 [retrieved on Feb. 27, 2009].
Clinical Trials. NCTO0622284. "Efficacy and safety of BI 1356 in combination with metformin in patients with type 2 diabetes" ClinicalTrials.gov (Online) No. NCT00622284, Feb. 13, 2008, p. 1-5, URL:http://clinicaltrial.gov/ct2/show/.
Clinical Trials. View of NCT00730275 updated on Aug. 7, 2008. "A study to assess the pharmacokinetics, safety and tolerability of Sitagliptin in adolescents". http://clinicaltrials.gov/archive/NCT00730275/2008_08_07.
Clinical Trials: NCT00954447, View on Jun. 14, 2010. "Efficacy and Safety of Linagliptin in Combination with Insulin in Patients with Type 2 Diabetes". <http://clinicaltrials.gov/archive/NCT00954447/2010_06_14>.
Clinical Trials: NCT00103857, "A Multicenter, Randomized, Double-Blind Factorial Study of the Co-Administration of MK0431 and Metformin in Patients With Type 2 Diabetes Mellitus Who Have Inadequate Glycemic Control" last updated on Apr. 27, 2015.
Clinical Trials: NCT00309608, "Efficacy and Safety of BI 1356 BS (Linagliptin) in Combination With Metformin in Patients With type2 Diabetes" Boehringer Ingelheim Pharmaceuticals, last updated on Jun. 24, 2014.
Clinical Trials: NCT00309608, "Efficacy and Safety of BI 1356 BS (Linagliptin) in Combination With Metformin in Patients With type2 Diabetes" Boehringer Ingelheim Pharmaceuticals, last updated: Dec. 11, 2013.
Clinical Trials: NCT00309608. Efficacy and safety of BI 1356 in combination with metformin in patients with type2 diabetes. Boehringer Ingelheim Pharmaceuticals, Jan. 27, 2009. Clinical Trials.gov . http://clinicaltrials.gov/archive/NCT00309608/2009_01_27.
Clinical Trials: NCT00602472. "BI 1356 in combination withe metformin and a sulphonylurea in Type 2 Diabetes". DrugLib.com, Nov. 3, 2008. http://www.druglib.com/trial/08/NCT00309608.html.
Clinical Trials: NCT00622284. Efficacy and Safety of BI 1356 in Combination with Metformin in Patients with Type 2 Diabetes. Boehringer Ingelheim Pharmaceuticals, Aug. 2008. http://clinicaltrials.gov/archive/NCT00622284/2010_01_13.
Clinical Trials: NCT00798161. "Safety and efficacy of Bi 1356 Plus Metformin in Type 2 Diabetes, Factorial Design". Clinical Trials.gov archive. A Service of the U.S> National Institutes of Health. Nov. 24, 2008, p. 1-3. http://clinicaltrials.gov/archive/NCT00798161/2008_11_24.
Colorcon, "Lactose Replacement with Starch 1500 in a Direct Compression Formula." 2005, pp. 1-4.
Colorcon, "Reducing Coated Tablet Defects from Laboratory through Production Scale: Performance of Hypromellose or Polyvinyl Alcohol-Based Aqueous Film Coating Systems." Opadry II, 2009, pp. 1-7.
Combs, D. W. et al., "Phosphoryl Chloride Induced Ring Contraction of 11,4-Benzodiazepinones to Chloromethylquinazolines". J. Heterocyclic Chemistry, BD. 23, 1986, p. 1263-1264.
Conarello, S.L. et al., "Mice lacking dipeptidyl peptidase IV are protected against obesity and insulin resistance". PNAS, May 27, 2003, vol. 100, No. 11, p. 6825-6830.
Conarello, S.L. et al; "Mice lacking dipeptidyl peptidase IV are protected against obesity and insulin resistance," PNAS 2003;

(56) References Cited

OTHER PUBLICATIONS

100:6825-6830; originally published online May 14, 2003; information current as of Dec. 2006. www.pnas.org/cgi/content/full/100/11/6825.

Cotton, M.L. et al., "L-649,923—The selection of an appropriate salt form and preparation of a stable oral formulation." International Journal of Pharmaceutics, 1994, vol. 109, Issue 3, pp. 237-249.

Craddy, P. et al., "Comparative Effectiveness of Dipeptidylpeptidase-4 Inhibitors in Type 2 Diabetes: A Systematic Review and Mixed Treatment Comparison." Diabetes Therapy, 2014, vol. 5, No. 1, pp. 1-41.

Crowe, E. et al., "Early identification and management of chronic kidney disease: summary of NICE guidance." British Medical Journal, 2008, vol. 337, pp. 812-815.

Cygankiewicz, Andrzej et al., Investigations into the Piperazine Derivatives of Dimethylxanthine:, Acta Polon. Pharm. [Papers of Polish Pharmacology], XXXOV, No. 5, pp. 607-612, 1977.

Dave, K.G. et al., "Reaction of Nitriles under Acidic Conditions, Part I. A General Method of Synthesis of Condensed Pyrimidines", J. Heterocyclic Chemistry, BD, 17, 1, ISSN 0022-152X, Nov. 1980, p. 1497-1500.

Dave, Rutesh H. "Overview of pharmaceutical excipients used in tablets and capsules." Drug Topics, Oct. 24, 2008.

Deacon, Carolyn F., et al., "Linagliptin, a xanthine based dipeptyl peptidase-4 inhibitor with an unusual profile for the treatment of type 2 diabetes" Expert Opinion Investig. Drugs 2010, 19 (1) p. 133-140.

Deacon, C.F. et al; "Dipeptidyl peptidase IV inhabitation as an approach to the treatment and prevention of type 2 diabetes: a historical perspective;" Biochemical and Biophysical Research Communications (BBRC) 294 (2002) 1-4.

Deacon, C.F., et al. Inhibitors of dipeptidyl peptidase IV: a novel approach for the prevention and treatment of Type 2 diabetes? Expert Opinion on Investigational Drugs, 2004, Sep., vol. 13, No. 9, p. 1091-1102.

Deacon, Carolyn F., "Dipeptidyl peptidase 4 inhibition with sitagliptin: a new therapy for Type 2 diabetes." Expert Opinion on Investigational Drugs, 2007, vol. 16, No. 4, pp. 533-545.

Definition of "prevent", e-dictionary, Aug. 15, 2013, http://dictionary.reference.com/browse/prevent.

DeMeester, I. et al.; "CD26, let it cut or cut it down", Review: Immunology Today; Aug. 1999, vol. 20, No. 8 pp. 367-375.

Demuth, H-U. et al., "Type 2 diabetes—Therapy with dipeptidyl peptidase IV inhibitors". Biochimica et Biophysica Acta, vol. 1751(1), 2005, p. 33-44.

Diabetes Frontier, 2007, vol. 18, No. 2, p. 145-148.

Diabetes Health Center, "Diabetic Retinopathy—Prevention." Retrieved online Mar. 22, 2011. www.diabetes.webmd.com/tc/diabetic-retinopathy-prevention <http://www.diabetes.webmd.com/tc/diabetic-retinopathy-prevention?print=true>.

Diabetesincontrol.com "EASD: Eucreas, a Combination of Galvus and Metformin, Recommended for Approval." Diabetes in Control. com, Sep. 25, 2007, Retrieved from internet on Nov. 30, 2012, http://www.diabetesincontrol.com/articles/53-diabetes-news/5145.

Diabetic Neuropathy, Retrieved online Mar. 6, 2012. www.mayoclinic.com/health/diabetic-neuropathy/DS01045/METHOD=print&DSE <http://www.mayoclinic.com/health/diabetic-neuropathy/DS01045/METHOD=print&DSE>.

Dittberner, S. et al., "Determination of the absolute bioavailability of BI 1356, a substance with non-linear pharmacokinetics, using a population pharmacokinetic modeling approach." Abstracts of the Annual Meeting of the Population Approach Group in Europe, 2007.

Drucker, Daniel J., "Dipeptidyl Peptidase-4 Inhibition and the Treatment of Type 2 Diabetes." Diabetes Care, 2007, vol. 30, No. 6, pp. 1335-1343.

Drucker, et al.., The incretin system:glucagon-like peptide-1 receptor agonists and dipeptidyl peptidase-4 inhibitors in type 2 diabetes. Lancet, 2006, 368: 1696-705.

Dugi, K. et al., "Safety, tolerability, pharmacokinetics, and pharmacodynamics of BI 1356, a novel DPP-IV inhibitor with a wide therapeutic window." Diabetic Medicine, 2006, vol. 23, Suppl. 4, p. 300.

Dugi, K.A. et al., "BI 1356, a novel xanthine-based DPP-IV inhibitor, exhibits high potency with a wide therapeutic window and significantly reduces postprandial glucose excursions after an oGTT". Diabetologia, vol. 50, No. Suppl 1, Sep. 2007, p. S367, and 43rd Annual Meeting of the European Association for the Study of Diabetes; Amsterdam, Netherlands, Sep. 18-21, 2007.

Dunitz, J. et al., "Disappearing Polymorphs." Acc. Chem. Res. 1995, vol. 28, No. 4, pp. 193-200.

Eckhardt Matthias et al: 8-(3-(R)-aminopiperidin-1-yl)-7-but-2-yny 1-3-methyl-1-(4-methyl-quina zolin-2-ylmethyl)-3,7-dihydropurine-2,6-dione (BI 1356), a highly potent, selective, long-acting, and orally bioavailable DPP-4 inhibitor for the treatment of type 2 diabetes: Journal of Medicinal Chemistry, American Chemical Society. Washington.; US, vol. 50, No. 26, Dec. 1, 2007, p. 6450-6451.

Eckhardt, M. et al., "3,5-dihydro-imidazo[4,5-d]pyridazin-4-ones: a class of potent DPP-4 inhibitors" Bioorganic & Medicinal Chemistry Letters, Pergamon, Elsevier Science, GB, vol. 18, No. 11, Jun. 1, 2008, pp. 3158-3162, XP022711188.

Edosada, C. Y. et al. "Selective Inhibition of Fibroblast Activation Protein Protease Based on Dipeptide Substrate Specificity." The Journal of Biological Chemistry, 2006, vol. 281, No. 11, pp. 7437-7444.

Elrishi M A et al: "The dipeptidyl-peptidase-4 (D::-4) inhibitors: A new class of oral therapy for patients with type 2 diabetes mellitus" Practical Diabetes International Chichester, vol. 24, No. 9, Nov. 1, 2007 pp. 474-482.

EMEA Guidelines on Eucreas®, 2007, pp. 1-27.

EMEA Guidelines on Galvus®, 2007, pp. 1-34.

EMEA: European Medicines Agency, "Galvus (vildagliptin)" Retrieved online on Jan. 21, 2016.

EMEA: European Medicines Agency, ICH Topic E4, "Dose Response Information to Support Drug Registration." 1994, pp. 1-10.

Eucreas Scientific Discussion, 2007, p. 1-27, www.emea.europa.eu/humandocs/PD/Fs/EPAR/eucreas/H-807-en6.pdf, Anonymous.

European Search Report for EP 08 15 9141 dated Apr. 6, 2009 (European counterpart of U.S. Appl. No. 12/143,128).

Eyjolfsson, Reynir "Lisinopril-Lactose Incompatibility." Drug Development and Industrial Pharmacy, 1998, vol. 24, No. 8, pp. 797-798.

Feng, J. et al., "Discovery of Alogliptin: A Potent, Selective, Bioavailable, and Efficacious Inhibitor of Dipeptidyl Peptidase IV." Journal of Medicinal Chemistry, 2007, vol. 50, No. 10, pp. 2297-2300.

Ferreira, L. et al., "Effects of Sitagliptin Treatment on Dysmetabolism, Inflammation, and Oxidative Stress in an Animal Model of Type 2 Diabetes (ZDF Rat)." Mediators of Inflammation, 2010, vol. 2010, pp. 1-11.

Ferry, Robert Jr., "Diabetes Causes." eMedicine Health, MedicineNet.com, 2013, Retrieved from internet on Aug. 22, 2013,<http://www.onhealth.com/diabetes_health/page3.htm#diabetes_causes>.

Flatt, P.R. et al. "Dipeptidyl peptidase IV (DPP IV) and related molecules in type 2 diabetes." Frontiers in Bioscience, 2008, vol. 13, pp. 3648-3660.

Florez, J. et al. "TCF7L2 Polymorphisms and Progression to Diabetes in the Diabetes Prevention Program." The New England Journal of Medicine, 2006, vol. 355, No. 3, pp. 241-250.

Forst, T. et al., "The Novel, Potent, and Selective DPP-4 Inhibitor BI 1356 Significantly Lowers HbA1c after only 4 weeks of Treatment in Patients with Type 2 Diabetes." Diabetes, Jun. 2007, Poster No. 0594P.

Forst, T. et al. "The oral DPP-4 inhibitor linagliptin significantly lowers HbA1c after 4 weeks of treatment in patients with type 2 diabetes mellitus." Diabetes, Obesity and Metabolism, 2011, vol. 13, pp. 542-550.

(56) References Cited

OTHER PUBLICATIONS

Fukushima et al., Drug for Treating Type II Diabetes (6), "action-mechanism of DPP-IV inhibitor and the availability thereof" Mebio, 2009, vol. 26, No. 8, p. 50-58.
Gall, "Prevalence of micro-and macroalbuminuria, arterial hypertension, retinopathy and large vessel disease in European type 2 (non-insulin dependent) diabetic patients", Diabetologia (1991) 655-661.
Gallwitz, B. "Sitagliptin with Metformin: Profile of a Combination for the Treatment of Type 2 Diabetes". Drugs of Today, Oct. 2007, 43(10), p. 681-689.
Gallwitz, B. et al., "2-year efficacy and safety of linagliptin compared with glimepiride in patients with type 2 diabetes inadequately controlled on metformin: a randomised, double-blind, non-inferiority trial." Lancet, 2012, vol. 380, pp. 475-483.
Gallwitz, B. et al., "Saxagliptin, a dipeptidyl peptidase IV inhibitor for the treatment of type 2 diabetes". IDRUGS, vol. 11, No. 12, Dec. 2008, p. 906-917.
Gallwitz, B. et al., DPP IV inhibitors for the Treatment of Type 2 Diabetes; Diabetes Frontier (2007) vol. 18, No. 6 pp. 636-642.
Gallwitz, B., "Safety and efficacy of linagliptin in type 2 diabetes patients with common renal and cardiovascular risk factors." Therapeutic Advances in Endocrinology and Metabolism, 2013, vol. 4, No. 3, pp. 95-105.
Galvus (Vildagliptin) Scientific Discussion, EMEA, 2007, pp. 1-34.
Garber, A. J. et al., "Effects of Vildagliptin on Glucose Control in Patients with Type 2 Diabetes Inadequately Controlled with a Sulphonylurea". Diabetes, Obesity and Metabolism (2008) vol. 10 pp. 1047-1055.
Garber, A.J. et al., "Simultaneous glyburide/metformin therapy is superior to component monotherapy as an initial pharmacological treatment for type 2 diabetes." Diabetes, Obesity and Metabolism, 2002, vol. 4, pp. 201-208.
Garber, A.J. et al., "Update: Vildaglitin for the treatment of Type 2 diabetes" Expert Opinion on Investigational Drugs, 200801GB, vol. 17, No. 1, Jan. 2008, p. 105-113.
Garcia-Soria, et al., "The dipeptidyl peptidase-4 inhibitor PHX1149 improves blood glucose control in patents with type 2 diabetes mellitus". Diabetes, Obesity and Metabolism, Apr. 2008, vol. 10, No. 4, p. 293-300.
Geka, 2001, vol. 67, No. 11, p. 1295-1299.
Gennaro, Alfonso R. Remington Farmacia, 2003, Spanish copy: p. 828, English copy: pp. 711-712, Preformulation, Chapter 38.
Gennaro, Alfonso R., Remington Farmacia, 19th Edition, Spanish copy, 1995, p. 2470.
Gennaro, Alfonso, R; Remington: The Science and Practice of Pharmacy: Oral Solid Dosage Forms; Mack Publishing Company, Philadelphia, PA (1995) vol. II, 19th Edition, Ch. 92 pp. 1615-1649.
Gennaro, Alfonso; Remington: The Science and Practice of Pharmacy, Twentieth Edition, 2000, Chapter 45, pp. 860-869.
Giron, D.; Thermal Analysis and Calorimetric Methods in the Characterisation of Polymorphs and Solvates; Thermochimica Acta (1995) vol. 248 pp. 1-59.
Glucophage® Prescribing Information, 2001.
Glucotrol XL (glipizide), package insert, Pfizer, Apr. 1, 2002.
Goldstein, L.A., et al., "Molecular cloning of seprase: a serine integral membrane protease from human melanoma." Biochimica et Biophysica Acta, vol. 1361, 1997, No. 1, pp. 11-19.
Gomez-Perez, et al, "Insulin Therapy:current alternatives", Arch. Med.Res. 36: p. 258-272 (2005).
Goodarzi, M.O. et al., "Metformin revisited: re-evaluation of its properties and role in the pharmacopoeia of modern antidiabetic agents." Diabetes, Obesity and Metabolism, 2005, vol. 7, pp. 654-665.
Graefe-Mody et al., "The novel DPP-4 inhibitor BI 1356 (proposed tradename ONDERO) and Metformin can be Safely Co-administered Without Dose Adjustment." Poster No. 553-P ADA Jun. 6-10, 2008, San Francisco http://professional.diabetes.org/content/posters/2008/p553-p.pdf.

Graefe-Mody, et al; Evaluation of the Potential for Steady-State Pharmacokinetic and Phamacodynamic Interactions Between the DPP-4 Inhibitor Linagliptin and Metformin in Healthy Subjects; Currents Medical Research and Opinion (2009) vol. 25, No. 8 pp. 1963-1972.
Graefe-Mody, U. et al., "Effect of Renal Impairment on the Pharmacokinetics of the Dipeptidyl Peptidase-4 Inhibitor Linagliptin." Diabetes, Obseity and Metabolism, 2011, pp. 939-946.
Greene, T.W, et al., "Protection for the Amino Group". Protective Groups in Organic Synthesis, 3rd edition, 1999, p. 494-653.
Greischel, et al., Drug Metabolism and Deposition, "The Dipeptidyl Peptidase-4 Inhibitor Linagliptin Exhibits Time- and Dpse-Dependent Localization in Kidney, Liver, and Intestine after Intravenous Dosing: Results from High Resolution Autoradiography in Rats", 2010, vol. 38, No. 9, p. 1443-1448.
Groop, P.-H. et al., "Effects of the DPP-4 Inhibitor Linagliptin on Albuminuria in Patients with Type 2 Diabetes and Diabetic Nephropathy." 48th EASD Annual Meeting, Berlin, Abstract 36, Oct. 2012. <http://www.abstractsonline.com/Plan/ViewAbstract.aspx?sKey=0b0017b9-9e90-4695-b9af-b6870e96a921&cKey=421edb9c-b940-40f0-b282-8e61245561d5&mKey=2dbfcat7-1539-42d5-8dda-0a94abb089e8>.
Guglielmi, C. et al., "Latent autoimmune diabetes in the adults (LADA) in Asia: from pathogenesis and epidemiology to therapy." Diabetes/Metabolism Research and Reviews, 2012, vol. 28, Supplement 2, pp. 40-46.
Gupta, V. et al., "Choosing a Gliptin." Indian Journal of Endocrinology and Metabolism, 2011, vol. 15, No. 4, pp. 298-308.
Gwaltney, S. "Medicinal Chemistry Approaches to the Inhibition of Dipeptidyl Peptidase IV", Current Topics in Medicinal Chemistry, 2008, 8, p. 1545-1552.
Gwaltney, S.L. II et al., "Inhibitors of Dipeptidyl Peptidase 4." Annual Reports in Medicinal Chemistry, 2005, vol. 40, pp. 149-165.
Hainer, Vojtech MD, PHD "Comparative Efficiency and Safety of Pharmacological Approaches to the Management of Obesity." Diabetes Care, 2011, vol. 34, Suppl. 2, pp. S349-S354.
Halimi, "Combination treatment in the management of type 2 diabetes: focus on vildagliptin and metformin as a single tablet", Vascular Health and Risk Management, 2008 481-92.
Halimi, S. et al., "Combination treatment in the management of type 2 diabetes: focus on vildagliptin and metformin as a single tablet." Vascular Health and Risk Management, 2008, vol. 4, No. 3, pp. 481-492.
Haluzik, M. et al., "Renal Effects of DPP-4 Inhibitors: A Focus on Microalbuminuria." International Journal of Endocrinology, 2013, vol. 35, No. 6, pp. 1-7.
Hammouda, Y. et al., "Lactose-induced Discoloration of Amino Drugs in Solid Dosage Form." Die Pharmazie, 1971, vol. 26, p. 181.
Hansen, H. et al., "Co-Administration of the DPP-4 Inhibitor Linagliptin and Native GLP-1 Induce Body Weight Loss and Appetite Suppression." 73rd Annual Meeting Science Session, ADA, Chicago, Jun. 21, 2013.
Hashida, Mitsuru, "Strategies for designing and developing oral administration formulations." Yakuji-Jiho, Inc., 1995, pp. 50-51.
Hayashi, Michio., "Recipe for Oral Hypoglycemic Agents to Pathological Condition" Pharmacy (2006) vol. 57, No. 9 pp. 2735-2739.
He, Y. L. et al., "Bioequivalence of Vildagliptin/Metformin Combination Tablets and Coadministration of Vildagliptin and Metformin as Free Combination in Healthy Subjects". J. Clinical Pharmacology, 2007, vol. 47, No. 9, Abstracts of the 36th Annual Meeting of the American College of Clinical Pharmacology, San Francisco, CA, Abstract 116, p. 1210.
He, Y.L. et al., "The influence of hepatic impairment on the pharmacokinetics f the dipeptidyl peptidase IV (DPP-4) inhibitor vildagliptin" European Journal of Clinical Pharmacology, vol. 63, No. 7, May 8, 2007, p. 677-686.
He, Y.L. et al., "The Influence of Renal Impairment on the Pharmacokinetics of Vildagliptin." Clinical Pharmacology & Therapeutics, 2007, vol. 81, Suppl. 1, Abstract No. PII-86.
Headland, K. et al., "The Effect of Combination Linagliptin and Voglibose on Glucose Control and Body Weight." 73rd Annual Meeting Science Session, ADA, Chicago, Jun. 21, 2013.

(56) References Cited

OTHER PUBLICATIONS

Heihachiro, A. et al., "Synthesis of Prolyl Endopeptidase Inhibitors and Evaluation of Their Structure-Activity Relationships: In Vitro Inhibition of Prolyl Endopeptidase from Canine Brain." 1993, Chemical and Pharmaceutical Bulletin, vol. 41, pp. 1583-1588.
Heise, et al., Diabetes, Obesity and Metabolism, "Pharmacokinetics, pharmacokinetics and tolerability of mutilple oral doses of linagliptin, a dipeptidyl peptidase-4 inhibitor in male type 2 diabetes patients", 2009, vol. 11, No. 8, p. 786-794.
Heise, T. et al., "Treatment with BI 1356, a Novel and Potent DPP-IV Inhibitor, Significantly Reduces Glucose Excursions after an oGTT in Patients with Type 2 Diabetes." A Journal of the American Diabetes Association, Jun. 2007, vol. 56, Supplement 1, Poster No. 0588P.
Herman G. A. et al., "Dipeptidyl Peptidase-4 Inhibitors for the Treatment of Type 2 Diabetes: Focus on Sitagliptin." Clinical Pharmacology and Therapeutics, 2007, vol. 81, No. 5, pp. 761-767.
Herman, Gary et al. "Co-Administration of MK-0431 and Metformin in Patients with Type 2 Diabetes Does Not Alter the Pharmacokinetics of MK-0431 or Metformin" (2005) Journal of American Diabetes Association vol. 54, Supplement 1, 3 pgs.
Hermann, Robert, et al; Lack of Association of PAX4 Gene with Type 1 Diabetes in the Hungarian Populations; Diabetes (2005) vol. 54 pp. 2816-2819.
Hermansen, K., "Efficacy and Safety of the Dipeptidyl Peptidase-4 Inhibitor, Sitagliptin, in Patients with Type 2 Diabetes Mellitus Inadequately Controlled on Glimepiride Alone or on Glimepiride and Metformin". Diabetes, Obesity and Metabolism (2007) vol. 9, No. 5 pp. 733-745.
Hilfiker, R. et al., "Relevance of Solid-state Properties for Pharmaceutical Products." Polymorphism in the Pharmaceutical Industry, 2006, Chapter 1, pp. 1-19.
Hinke, S.A. et al., "Metformin Effects on Dipeptidylpeptidase IV Degradation of Glucagon-like Peptide-1." Biochemical and Biophysical Research Communications, 2002, vol. 291, No. 5, pp. 1302-1308.
Hinke, S.A. et al., "On Combination Therapy of Diabetes With Metformin and Dipeptidyl Peptidase IV Inhibitors." Diabetes Care, 2002, vol. 25, No. 8, pp. 1490-1492.
Hinnen, D. et al., "Incretin Mimetics and DPP-IV Inhibitors: New Paradigms for the Treatment of Type 2 Diabetes." Journal of the American Board of Family Medicine, 2006, vol. 19, No. 6, pp. 612-620.
Hocher, B. et al., "Renal and Cardiac Effects of DPP-4 Inhibitors—from Preclinical Development to Clinical Research." Kidney & Blood Pressue Research, 2012, vol. 36, No. 1, pp. 65-84.
Hocher, B. et al., "The novel DPP-4 inhibitors linagliptin and BI 14361 reduce infarct size after myocardial ischemia/reperfusion in rats." International Journal of Cardiology, 2013, vol. 167, pp. 87-93.
Holman, et al., "Addition of biphasic, prandial, or basal insulin to oral therapy in type 2 diabetes", N. England Journal Medicine, p. 1716-1730, 2007.
Horsford, E. N. "On the source of free hydrochloric acid in the gastric juice." Proceedings of the Royal Society of London, Published in 1868-1869, vol. 17, pp. 391-395.
Hu, Y. et al., "Synthesis and Structure-activity Relationship of N-alkyl Gly-boro-Pro Inhibitors of DPP4, FAP, and DPP7." Bioorganic & Medicinal Chemistry Letters 15, 2005, pp. 4239-4242.
Huettner Silks et al: "BI 1356, a novel and selective xanthine based DPP-IV inhibitor, demonstrates good safety and tolerability with a wide therapeutic window" Diabetes< American Diabetes Association, US, vol. 56, No. Suppl 1, Jun. 1, 2007, p. A156.
Hull, R. et al., "Nephrotic syndrome in adults." British Medical Journal, 2008, vol. 336, pp. 1185-1190.
Hunziker, D. et al, "Inhibitors of DPP IV—recent advances and structural views", Current Topics in Medicinal Chemistry, 2005, vol. 5 issue 16, pp. 1623-1637.
Huttner, S. et al., "Safety, Tolerability, Pharmacokinetics, and Pharmacodynamics of Single Oral Doses of BI 1356, an Inhibitor of Dipeptidyl Peptidase 4, in Healthy Male Volunteers." Journal of Clinical Pharmacology, 2008, vol. 48, No. 10, pp. 1171-1178.
International Search Report—European Search Report for PCT/EP2003/09127 dated Mar. 1, 2011.
International Search Report and Written Opinion for PCT/EP2006/064657 dated Nov. 2, 2006.
International Search Report and Written Opinion for PCT/EP2007/054201 dated Aug. 29, 2007.
International Search Report and Written Opinion for PCT/EP2007/054270 dated Aug. 14, 2007.
International Search Report and Written Opinion for PCT/EP2008/060740 dated Mar. 30, 2009.
International Search Report and Written Opinion for PCT/EP2009/053978 dated Sep. 29, 2009.
International Search Report and Written Opinion for PCT/EP2009/056722 dated Aug. 13, 2009.
International Search Report and Written Opinion for PCT/EP2009/060521 dated Mar. 9, 2010.
International Search Report and Written Opinion for PCT/EP2009/063511 dated Feb. 26, 2010.
International Search Report and Written Opinion for PCT/EP2009/067772 dated Apr. 14, 2010.
International Search Report and Written Opinion for PCT/EP2010/050103 dated Mar. 22, 2010.
International Search Report and Written Opinion for PCT/EP2010/051093 dated Jul. 14, 2010.
International Search Report and Written Opinion for PCT/EP2010/051817 dated Jun. 8, 2010.
International Search Report and Written Opinion for PCT/EP2010/064691 dated Apr. 6, 2011.
International Search Report and Written Opinion for PCT/EP2010068349 dated Feb. 4, 2011.
International Search Report and Written Opinion for PCT/EP2011/054169 dated Aug. 4, 2011.
International Search Report and Written Opinion for PCT/EP2011/057163 dated Jun. 27, 2011.
International Search Report and Written Opinion for PCT/EP2011/057256 dated Jul. 22, 2011.
International Search Report and Written Opinion for PCT/EP2011/060449 dated Sep. 27, 2011.
International Search Report and Written Opinion for PCT/EP2011/070156 dated Jan. 17, 2012.
International Search Report and Written Opinion for PCT/EP2012/053910 dated May 14, 2012.
International Search Report and Written Opinion for PCT/EP2012/063852 dated Sep. 6, 2012.
International Search Report and Written Opinion for PCT/EP2012/077024 dated Feb. 19, 2013.
International Search Report and Written Opinion for PCT/EP2013/054524 dated Apr. 24, 2013.
International Search Report and Written Opinion for PCT/EP2013/059828 dated Aug. 6, 2013.
International Search Report and Written Opinion for PCT/EP2013/059831 dated Aug. 9, 2013.
International Search Report and Written Opinion for PCT/EP2013/060311 dated Aug. 9, 2013.
International Search Report and Written Opinion for PCT/EP2013/060312 dated Sep. 4, 2013.
International Search Report and Written Opinion for PCT/EP2013/070978 dated Oct. 31, 2013.
International Search Report and Written Opinion for PCT/EP2014/055113 dated May 16, 2014.
International Search Report and Written Opinion for PCT/EP2014/062398 dated Aug. 20, 2014.
International Search Report and Written Opinion for PCT/EP2015/054114 dated May 12, 2015.
International Search Report and Written Opinion for PCT/EP2015/074030 dated Feb. 4, 2016.
International Search Report and Written Opinon for PCT/EP2007/054204 dated Aug. 3, 2007.
International Search Report for PCT/EP03/12821 dated Mar. 30, 2004.

(56) References Cited

OTHER PUBLICATIONS

International Search Report for PCT/EP03/13648 dated Apr. 5, 2004.
International Search Report for PCT/EP2002/01820 dated May 7, 2002.
International Search Report for PCT/EP2003/12821 dated Mar. 30, 2004.
International Search Report for PCT/EP2003/13648 dated Apr. 5, 2004.
International Search Report for PCT/EP2005/001427 dated May 23, 2005.
International Search Report for PCT/EP2005/055711 dated Mar. 29, 2006.
International Search Report for PCT/EP2007/054204 dated Mar. 8, 2007.
International Search Report for PCT/EP2007/058181 dated Nov. 28, 2007.
International Search Report for PCT/EP2008/060738 dated Nov. 5, 2008.
International Search Report for PCT/EP2009/060170 dated Oct. 28, 2009.
International Search Report for PCT/EP2010/064691 dated Jan. 20, 2011.
International Search Report for PCT/EP2013/060309 dated Aug. 9, 2013.
"Betahistine diHCL CF 16 mg, tabletten," Dutch Medicines Evaluation Board, Dated Apr. 13, 1988, Retrieved online from: <http://db.cbg-meb.nl/ords/f?p=111:3:0:SEARCH:NO::P0_DOMAIN,P0_LANG,P3_RVG1:H,EN,57626>.
"Betahistine diHCL CF 8 mg, tabletten," Dutch Medicines Evaluation Board, Dated Apr. 13, 1988, Retrieved online from: <http://db.cbg-meb.nl/ords/f?p=111:3:0:SEARCH:NO::P0_DOMAIN,P0_LANG,P3_RVG1:H,EN,56227>.
"Sifrol 0,088 mg, tabletten," Dutch Medicines Evaluation Board, Dated Oct. 14, 1997, Retrieved online from: <http://db.cbg-meb.nl/ords/f?p=111:3:0:SEARCH:NO::P0_DOMAIN,P0_LANG,P3_RVG1:H,EN,70120>.
"Sifrol 0,18 mg, tabletten," Dutch Medicines Evaluation Board, Dated Oct. 14, 1997, Retrieved online from: <http://db.cbg-meb.nl/ords/f?p=111:3:0:SEARCH:NO::P0_DOMAIN,P0_LANG,P3_RVG1:H,EN,70121>.
"Sifrol 0,35 mg, tabletten," Dutch Medicines Evaluation Board, Dated Nov. 16, 1999, Retrieved online from: <http://db.cbg-meb.nl/ords/f?p=111:3:0:SEARCH:NO::P0_DOMAIN,P0_LANG,P3_RVG1:H,EN,70673>.
"Sifrol 0,70 mg, tabletten," Dutch Medicines Evaluation Board, Dated Oct. 14, 1997, Retrieved online from: <http://db.cbg-meb.nl/ords/f?p=111:3:0:SEARCH:NO::P0_DOMAIN,P0_LANG,P3_RVG1:H,EN,70122>.
"Sifrol 1,1 mg, tabletten," Dutch Medicines Evaluation Board, Dated Oct. 14, 1997, Retrieved online from: <http://db.cbg-meb.nl/ords/f?p=111:3:0:SEARCH:NO::P0_DOMAIN,P0_LANG,P3_RVG1:H,EN,70124>.
Abstract for AU 2003280680, Jun. 18, 2004.
Abstract for AU 2009224546, Sep. 17, 2009.
Abstract in English for DE10109021, 2002.
Abstract in English for DE19705233, Aug. 13, 1998.
Abstract in English for DE2205815, 1972.
Abstract in English for EP0023032, 1981.
Abstract in English for JP 2002/348279, Dec. 4, 2002.
Abstract in English for JP 2003/286287, Oct. 10, 2003.
Abstract in English for KR20070111099, Nov. 11, 2007.
ACTOS Prescribing Information, 1999, pp. 1-26.
Adebowale, K.O. et al., "Modification and properties of African yam bean (Sphenostylis stenocarpa Hochst. Ex A. Rich.) Harms starch I: Heat moisture treatments and annealing." Food Hydrocolloids, 2009, vol. 23, No. 7, pp. 1947-1957.
Ahren, B. et al., "Twelve- and 52-Week Efficacy of the Dipeptidyl Peptidase IV Inhibitor LAF237 in Metformin-Treated Patients With Type 2 Diabetes." Diabetes Care, 2004, vol. 27, No. 12, pp. 2874-2880.
Ahren, Bo "Novel combination treatment of type 2 diabetes DPP-4 inhibition + metformin." Vascular Health and Risk Management 2008, vol. 4, No. 2, pp. 383-394.
Ahren, Bo et al; Improved Meal-Related b-Cell Function and Insulin Sensitivity by the Dipeptidyl Peptidase-IV Inhibitor Vildagliptin in Metformin-Treated Patients with Type 2 Diabetes Over 1 Year; Diabetes Care (2005) vol. 28, No. 8 pp. 1936-1940.
Ahren, Bo; "DPP-4 inhibitors", Best practice and research in clinical endocrinology and metabolism—New therapies for diabetes 200712 GB LNKD-DOI:10.1016/J. Beem.2007.07.005, vol. 21, No. 4, Dec. 2007, pp. 517-533.
Al-Masri, I.M. et al., "Inhibition of dipeptidyl peptidase IV (DPP IV) is one of the mechanisms explaining the hypoglycemic effect of berberine." Journal of Enzyme Inhibition and Medicinal Chemistry, 2009, vol. 24, No. 5, pp. 1061-1066.
Alter, M. et al., "DPP-4 Inhibition on Top of Angiotensin Receptor Bockade Offers a New Therapeutic Approach for Diabetic Nephropathy." Kidney and Blood Pressue Research, 2012, vol. 36, No. 1, pp. 119-130.
American Association of Clinical Endocrinologists, "Medical Guidelines for Clinical Practice for the Management of Diabetes Mellitus." Endocrine Practice, 2007, Col. 13, Suppl. 1, pp. 1-68.
American Diabetes Association, "Standards of Medical Care in Diabetes—2008." Diabetes Care, Jan. 2008, vol. 31, Supplement 1, pp. S12-S54.
Anstee, Quentin M. et al. "Mouse models in non-alcholic fatty liver disease and steatohepatitis research" (2006) International Journal of Expermental Pathology, vol. 87, pp. 1-16.
Augeri, D.J. "Discovery and Preclinical Profile of Saxagliptin (GMB-477118): A Highly Potent, Long-Acting, Orally Active Dipeptidyl Peptidase IV Inhibitor for the Treatment of Type 2 Diabetes". Journal Med. Chem, 2005, vol. 48, No. 15, p. 5025-5037.
Augusti, D.V. et al., "Quantitative determination of the enantiomeric composition of thalidomide solutions by electrospray ionizatio tandem mass spectrometry". Chem Comm, 2002, p. 2242-2243.
Augustyns, K. et al., The Unique Properties of Dipeptidyl-peptidase IV (DPP IV/CD 26) and the Therapeutic Potential of DPP-IV Inhibitors, Current Medicinal Chemistry, vol. 6, No. 4, 1999, pp. 311-327.
Aulinger, B.A. et al., "Ex-4 and the DPP-IV Inhibitor Vildagliptin have Additive Effects to Suppress Food Intake in Rodents". Abstract No. 1545-P, 2008.
Aulton, Michael E., Pharmaceutics: The Science of Dosage Form Design, Second Edition, 2002, pp. 441-448.
Baetta, R. et al., "Pharmacology of Dipeptidyl Peptidase-4 Inhibitors." Drugs, 2011, vol. 71, No. 11, pp. 1441-1467.
Balaban, Y.H. et al., "Dipeptidyl peptidase IV (DDP IV) in NASH patients" Annals of Hepatology, vol. 6, No. 4, Oct. 1, 2007, pp. 242-250, abstract.
Balbach, S. et al., "Pharmaceutical evaluation of early development candidates " the 100 mg-approach. International Journal of Pharmaceutics, 2004, vol. 275, pp. 1-12.
Balkan, B. et al, "Inhibition of dipeptidyl peptidase IV with NVP-DPP728 increases plasma GLP-1 (7-36 amide) concentrations and improves oral glucose tolerance in obses Zucker rates". Diabetologia, 1999, 42, p. 1324-1331.
Banker, Gilbert S., "Prodrugs." Modern Pharmaceutics Third Edition, Marcel Dekker, Inc., 1996, p. 596.
Bastin, R.J. et al., "Salt Selection and Optimization Procedures for Pharmaceutical New Chemical Entities". Organic Process Research and Development, 2000, vol. 4, pp. 427-435.
Beauglehole, Anthony R., "N3-Substituted Xanthines as Irreversible Adenosine Receptor Antagonists." Ph.D. Thesis, Deakin University, Australia, 2000, pp. 1-168.
Beljean-Leymarie et al., Hydrazines et hydrazones hétérocycliques. IV. Synthèses de dérivés de l'hydrazine dans la série des imidazo[4,5-d]pyridazinones-4, Can. J. Chem., vol. 61, No. 11, 1983, pp. 2563-2566.

(56) References Cited

OTHER PUBLICATIONS

Berge, S. et al., "Pharmaceutical Salts." Journal of Pharmaceutical Sciences, 1977, vol. 66, No. 1, pp. 1-19.
Bernstein, Joel "Polymorphism in Molecular Crystals." Oxford University Press, 2002, p. 9.
Blech, S. et al., "The Metabolism and Disposition of the Oral Dipeptidyl Peptidase-4 Inhibitor, Linagliptin, in Humans", Drug Metabolism and Disposition, 2010, vol. 38, No. 4, p. 667-678.
Bollag, R.J. et al; "Osteoblast-Derived Cells Express Functional Glucose-Dependent Insulinotropic Peptide Receptors," Endocrinology, vol. 141, No. 3, 2000, pp. 1228-1235.
Borloo, M. et al. "Dipeptidyl Peptidase IV: Development, Design, Synthesis and Biological Evaluation of Inhibitors." 1994, Universitaire Instelling Antwerpen, vol. 56, pp. 57-88.
Bosi, E. et al., "Effects of Vildagliptin on Glucose Control Over 24 Weeks in Patients With Type 2 Diabetes Inadequately Controlled With Metformin." Diabetes Care, 2007, vol. 30, No. 4, pp. 890-895.
Boulton, D.W. et al., "Safety, Tolerability, Pharmacokinetics and Pharmacodynamics of Once-Daily Oral Doses of Saxagliptin for 2 Weeks in Type 2 Diabetic and Healthy Subjects." Diabetes, 2007, Supplement 1, vol. 56, pp. A161.
Brazg, R. et al: "Effect of adding sitagliptin, a dipeptidyll peptidase-4 inhibitor, to metformin on 24-h glycaemic control and beta-cell function in patients with type 2 diabetes." Diabetes, Obesity and Metabolism, Mar. 2007, vol. 9, No. 2, Mar. 2007 pp. 186-193.
Brazg, Ronald, et al; Effect of Adding MK-0431 to On-Going Metforming Therapy in Type 2 Diabetic Patients Who Have Inadequate Glycemic Control on Metformin; Diabetes ADA (2005) vol. 54, Suppl. 1 p. A3.
Brittain, H.G., "Methods for the Characterization of Polymorphs: X-Ray Powder Diffraction," Polymorphism in Pharmaceutical Solids, 1999, p. 235-238.
Matsumiya, Teruhiko, et al., "Therapeutic Drugs for Clinicians" Diagnosis and Treatment (2008) vol. 96, No. 2 pp. 389-390.
Mayo Clinic Staff: "Nonalchoholic fatty liver disease: Prevention" [retrieved on Nov. 30, 2012]. retrieved from the Internet: ,URL: http://www.mayoclinic.com/health/nonalcoholic-fatty-liver-disease/DS00577DSECTION=prevention>.
McNay, David E.G. et al., "High fat diet causes rebound weight gain." Molecular Metabolism, 2013, vol. 2, pp. 103-108.
Medline Plus, "Obesity" 2013, Retrieved from internet on Aug. 22, 2013, http://www.nlm.nih.gov/medlineplus/obesity.html.
Meece, J. "When Oral Agents Fail: Optimizing Insulin Therapy in the Older Adult". Consultant Pharmacist, The Society, Arlington, VA US. vol. 24, No. Suppl B, Jun. 1, 2009, p. 11-17.
Mendes, F.D, et al. "Recent advances in the treatment of nonalcoholic fatty liver disease". Expert Opinion on Investigational Drugs, vol. 14, No. 1, Jan. 1, 2005, p. 29-35.
Merck Manual of Diagnosis and Therapy: "Obesity." 1999, 17th Edition, Chapter 5, pp. 58-62.
Merck: "Initial Therapy with Janumet (sitagliptin/metformin) provided significantly greater blood sugar lowering compared to metformin alone in patients with type 2 diabetes". Webwire.com, Jun. 8, 2009, p. 1-4. http://www.webwire.com/ViewPressRel.asp?aId=96695.
Mikhail, Nasser, "Incretin mimetics and dipeptidyl peptidase 4 inhibitors in clinical trials for the treatment of type 2 diabetes." Expert Opinion on Investigational Drugs, 2008, vol. 17, No. 6, pp. 845-853.
MIMS Jan. 2009, "Sitagliptin." pp. 152-153.
Moritoh, Y. et al., "Combination treatment with alogliptin and voglibose increases active GLP-1 circulation, prevents the development of diabetes and preserves pancreatic beta-cells in prediabetic db/db mice." Diabetes, Obesity and Metabolism, 2010, vol. 12, pp. 224-233.
Nabors, Lyn O'Brien "Alternative Sweeteners." Marcel Dekker, Inc., 2001, pp. 235, 339-340.

Naik, R. et al., "Latent Autoimmune Diabetes in Adults." The Journal of Clinical Endocrinology and Metabolism, 2009, vol. 94, No. 12, pp. 4635-4644.
Nar, Herbert "Analysis of Binding Kinetics and Thermodynamics of DPP-4 Inhibitors and their Relationship to Structure." 2nd NovAliX Conference: Biophysics in drug discovery, Strasbourg, France, Jun. 9-12, 2015.
Nathan, D. et al., "Management of Hyperglycemia in Type 2 Diabetes: A Consensus Algorithm for the Initiation and Adjustment of Therapy." Diabetes Care, Aug. 2006, vol. 29, No. 8, pp. 1963-1972.
National Program for Care Guidelines, "Type 2 Diabetes mellitus." 2002, First Edition, pp. 1-50.
Nauck, M. A. et al., "Efficacy and Safety of Adding the Dipeptidyl Peptidase-4 Inhibitor Alogliptin to Metformin Therapy in Patients with Type 2 Diabetes Inadequately Controlled with Metformin Monotherapy: A Multicentre, Randomised, Double-Blind, Placebo-Cotrolled Study." Clinical Practice, 2008, vol. 63, No. 1, pp. 46-55.
Nauck, M. A. et al., "Efficacy and Safety of the Dipeptidyl Peptidase-4 Inhibitor, Sitagliptin, Compared with the Sulfonylurea, Glipizide, in Patients with Type 2 Diabetes Inaduately Controlled on Metformin alone: A Randomized, Double-Blind, Non-Inferiority Trial." Diabetes Obesity and Metabolism, 2007, vol. 9, No. 2, pp. 194-205.
Nielsen, L., "Incretin Mimetics and DPP-IV Inhibitors for the Treatment of Type 2 Diabetes." Drug Discovery Today, 2005, vol. 10, No. 10, pp. 703-710.
Nihon Ijinpo, Japan Medicinal Journal, 2001, No. 4032, p. 137.
Novartis AG, Investor Relations Release, "Galvus, a new oral treatment for type 2 diabetes, receives positive opinion recommending European Union approval." Securities and Exchange Commission, Form 6-K, 2007, pp. 1-4.
O'Farrell, et al., "Pharmacokinetic and Pharmacodynamic Assessments of the Dipeptidyl Peptidase-4 Inhibitor PHX1149: Double-Blind, Placebo-controlled, Single-and Multiple-Dose Studies in Healthy Subjects". Clinical Therapeutics, Excerpta Medica, Princeton, NJ, vol. 29, No. 8, 2007, p. 1692-1705.
Office Action for U.S. Appl. No. 10/695,597 dated May 2, 2008.
Oz, Helieh S., "Methionine Deficiency and Hepatic Injury in a Dietary Steatohepatitis Model." Digestive Diseases and Sciences, 2008, vol. 53, No. 3, pp. 767-776.
Patani George A. et al.: "Bioisoterism : A Rational Approach in Drug Design", Chemical Reviews, 1996, vol. 96, No. 8, pp. 3147-3176.
Pearson, E. R. et al., "Variation in TCF7L2 Influences Therapeutic Response to Sulfonylureas." Diabetes, 2007, vol. 56, pp. 2178-2182.
Pei, Z.: "From the bench to the bedside: Dipeptidyl peptidase IV inhibitors, a new class of oral antihyperglycemic agents" Current Opinion in Drug Discovery and Development, Current Drugs, London, GB vol. 11, No. 4, Jul. 1, 2008 pp. 512-532.
Pietruck, F. et al., "Rosiglitazone is a safe and effective treatment option of new-onset diabetes mellitus after renal transplantation." Transplant International, 2005, vol. 18, pp. 483-486.
Pilgaard, K. et al., "The T allele of rs7903146 TCF7L2 is associated with impaired insulinotropic action of incretin hormones, reduced 24 h profiles of plasma insulin and glucagon, and increased hepatic glucose production in young healthy men." Diabetologia, 2009, vol. 52, pp. 1298-1307.
Plummer, C.J.G. et al., "The Effect of Melting Point Distributions on DSC Melting Peaks." Polymer Bulletin, 1996, vol. 36, pp. 355-360.
Pospisilik, et al; Dipeptidyl Peptidase IV Inhibitor Treatment Stimulates ? -Cell Survival and Islet Neogenesis in Streptozotocin-Induced Diabetic Rats; Diabetes, vol. 52, Mar. 2003 pp. 741-750.
Poudel, Resham R., "Latent autoimmune diabetes of adults: From oral hypoglycemic agents to early insulin." Indian Journal of Endocrinology and Metabolism, 2012, vol. 16, Supplement 1, pp. S41-S46.
Pratley, R. et al., "Inhibition of DPP-4: a new therapeutic approach for the treatment of type 2 diabetes." Current Medical Research and Opinion, 2007, vol. 23, No. 4, pp. 919-931.

(56) References Cited

OTHER PUBLICATIONS

Prescribing Information, Package insert for Leprinton tablets 100mg, Manufacturer: Tatsumi Kagaku Co., Ltd., Mar. 2003, pp. 1-3.
Priimenko, B. A., et al; Synthesis and Pharmacological Activity of Derivates of 6,8-Dimethyl Imidazo(1,2-f) Xanthine-(Russ.); Khimiko-Farmatsevticheskii zhurnal (1984) vol. 18, No. 12 pp. 1456-1461.
Radermecker, Regis et al., "Lipodystrophy Reactions to Insulin." American Journal of Clinical Dermatology, 2007, vol. 8, pp. 21-28.
Rask-Madsen, C. et al., "Podocytes lose their footing." Nature, 2010, vol. 468, pp. 42-44.
Rhee et al.: "Nitrogen-15-Labeled Deoxynucleosides. 3. Synthesis of [3-15N]-2'-Deoxyadenosine" J. Am. Chem. Soc. 1990, 112, 8174-8175.
Rosenbloom, et al., "Type 2 Diabetes mellitus in the child and adolescent", Pediatric Diabetes, 2008, p. 512-526.
Rosenstock, et al., "Efficacy and tolerability of initial combination therapy with vildagliptin and pioglitazone compared with component montherapy in patients with type 2 diabetes". Diabetes, Obesity and Metabolism, Mar. 2007, vol. 9, No. 2, p. 175-185.
Rosenstock, et al., Sitagliptin Study 019 Groups, Efficacy and safety of the dipeptidyl peptidase-4 inhibitor sitagliptin, Clinical Therapeutics, 2006, vol. 28, Issue 10, p. 1556-1568.
Rosenstock, J. et al., "Alogliptin added to insulin therapy in patients with type 2 diabetes reduces HbA1c without causing weight gain or increased hypoglycaemia". Diabetes, Obesity and Metabolishm, Dec. 2009, vol. 11. No. 12, p. 1145-1152.
Rosenstock, J. et al., "Triple Therapy in Type 2 Diabetes." Diabetes Care, 2006, vol. 29, No. 3, pp. 554-559.
Rowe, R. et al., Handbook of Pharmaceutical Excipients, Fifth Edition, Pharmaceutical Press, 2006, pp. 389-395, 449-453, and 731-733.
Rowe, R. et al., Handbook of Pharmaceutical Excipients, Fourth Edition, Pharmaceutical Press and American Pharmaceutical Association, 2003, pp. 323-332.
Russell-Jones, D. et al., "Liraglutide vs insulin glargine and placebo in combination with metformin and sulfonylurea therapy in type 2 diabetes mellitus (LEAD-5 met+SU): a randomised controlled trial." Diabetologia, 2009, vol. 52, pp. 2046-2055.
Salomon, J. et al; Ultraviolet and g-Ray-Induced Reactions of Nucleic Acid Constituents. Reactions of Purines with Amines; Photochemistry and Photobiology (1974) vol. 19 pp. 21-27.
Sarafidis, P. et al., "Cardiometabolic Syndrome and Chronic Kidney Disease: What is the link?"JCMS 2006, 1: p. 58-65.
Sathananthan, A., et al., "Personalized pharmacotherapy for type 2 diabetes mellitus". Personalized Medicine 2009 Future Medicine Ltd, vol. 6, No. 4, Jul. 2009, p. 417-422.
Sauer, R, et al. "Water-soluble phosphate prodrugs of 1-Propargyl-7-styrylxanthine derivatives, A2A-selective adenosine receptor antagonists". Journal Med. Chem., vol. 43, Issue 3, Jan. 2000, p. 440-448.
International Search Report for PCT/EP2013/070979 dated Nov. 26, 2013.
International Search Report for PCT/EP2014/060160 dated Nov. 8, 2014.
Inukai, T., "Treatment of Diabetes in Patients for Whom Metformin Treatment is Not Appropriate." Modern Physician, 2008, vol. 28, No. 2, pp. 163-165.
Inzucchi, Silvio E., "Oral Antihyperglycemic Therapy for Type 2 Diabetes." The Journal of the American Medical Association, 2002, vol. 287, No. 3, pp. 360-372.
Isomaa, B. et al., "Cardiovascular Morbidity and Mortality Associated With the Metabolic Syndrome." Diabetes Care, 2001, vol. 24, No. 4, pp. 683-689.
Iwamoto, Yasuhiko, "Insulin Glargine." Nippon Rinsho, 2002, vol. 60, Suppl. 9, pp. 503-515.
Janumet Prescribing Information, revised Jan. 2008.
Januvia Medication Guide, 2010.
Januvia Prescribing Information and Product Label, 2006.
Januvia, 25mg, 50mg, 100 mg, Summary of Product Characteristics, 2015, www.medicines.org.uk/EMC <http://www.medicines.org.uk/EMC>.
Johansen, O. E. et al., "Cardiovascular safety with linagliptin in patients with type 2 diabetes mellitus: a pre-specified, prospective, and adjudicated meta-analysis of a phase 3 programme." Cardiovascular Diabetology, Biomed Central, 2012, vol. 11, No. 3, pp. 1-10.
Johansen, O.E. et al., "b-cell Function in Latnet Autoimmune Diabetes in Adults (LADA) Treated with Linagliptin Versus Glimepiride: Exploratory Results from a Two Year Double-Blind, Randomized, Controlled Study." www.abstractsonline.com, Jun. 10, 2012, XP-002708003.
John Hopkins Children's Center, "Liver Disorders and Diseases." Retrieved online May 26, 2014 <http://www.hopkinschildrens.org/non-alcoholic-fatty-liver-disease.aspx>.
Jones, R.M. et al., "GPR119 agonists for the treatment of type 2 diabetes". Expert Opinion on Therapeutic Patents 2009 Informa Healthcare for GBR LNKSD—DOI: 10.1517/13543770903153878, vol. 19, No. 10, Oct. 2009, p. 1339-1359.
Kanada, S. et al., "Safety, tolerability, pharmacokenetics and pharmacodynamics of multiple doses of BI 1356 (proposed tradename ONDERO), a dipeptidyl peptidase 4 inhibitor, in Japanese patients with type 2 diabetes" Diabetes, vol. 57, No. Suppl. 1, Jun. 2008, p. A158-A159 and 68th Annual Meeting of the American Diabetes Association: San Francisco, CA , Jun. 6-10, 2008.
Kelly. T., "Fibroblast activation protein-cx and dipeptidyl peptidase IV (CD26)P: Cell-surface proteases that activate cell signaling and are potential targets for cancern therapy". Drug Resistence Update 8, 2005, vol. 8. No. 1-2, pp. 51-58.
Kendall, D. M. et al., "Incretin Mimetics and Dipeptidyl Peptidase-IV Inhibitors: A Review of Emerging Therapies for Type 2 Diabetes." Diabetes Technology & Therapeutics, 2006, vol. 8, No. 3, pp. 385-398.
Kharkevich, D. A., "Educational Literature" Pharmacology (1987) Third Edition, Meditsina Press, Moscow pp. 47-48.
Kibbe, A., Editor. Handbook of Pharmaceutical Excipients, Third Edition, Copovidon—pp. 196-197, Date of Revision: Dec. 16, 2008. Mannitol—pp. 424-425, Date of Revision: Feb. 19, 2009, Published in 2009.
Kidney Disease (Nephropathy), Retrieved online May 13, 2013. www.diabetes.org/living-with-diabetes/complications/kidney-disease-nephropathy.html <http://www.diabetes.org/living-with-diabetes/complications/kidney-disease-nephropathy.html>.
Kim, D. et al., "(2R)-4-Oxo-4-(3-(Trifluoromethyl)-5,6-dihydro[1,2,4]triazolo[4,3-a]pyrazin-7(8H)-yl]-1-(2,4,5-trifluorophenyl)butan-2-amine: A Potent, Orally Active Dipeptidyl Peptidase IV inhibitor for the Treatment of Type 2 Diabetes." Journal Med. Chem., 2005, 48, p. 141-151.
Kim, Kwang-Rok et al., "KR-62436, 6-{2-{2-(5-cyano4,5-dihydropyrazol-1-yl)-2-oxoethylamino}ethylamino} nicotinonitrile, is a novel dipeptidyl peptidase-IV (DDP-IV inhibitor with anti-hyperglycemic activity" European Journal of Pharmacology 518, 2005, p. 63-70.
Kiraly, K. et al., "The dipeptidyl peptidase IV (CD26, EC 3.4.14.5) inhibitor vildagliptin is a potent antihyperalgesic in rats by promoting endomorphin-2 generation in the spinal cord." European Journal of Pharmacology, 2011, vol. 650, pp. 195-199.
Kirpichnikov, D. et al., "Metformin: An Update." Annals of Internal Medicine, 2002, vol. 137, No. 1, pp. 25-33.
Kishore, Preeti MD., "Complications of Diabetes Mellitus." Merck Manual Consumer Version, 2016, pp. 1-7.
Klein, T. et al., "Linagliptin alleviates hepatic steatosis and inflammation in a mouse model of non-alcoholic steatohepatitis." Medical Molecular Morphology, 2014, vol. 47, pp. 137-149.
Knorr, M. et al., "Comparison of Direct and Indirect Antioxidant Effects of Linagliptin (BI 1356, Ondero) with other Gliptins—Evidence for Anti-Inflammatory Properties of Linagliptin". Free Radical Biology and medicine, Elsevier Science, U.S. vol. 49, Oct. 23, 2010, p. S197.
Knowler, W.C. et al., "Reduction in the Incidence of Type 2 Diabetes with Lifestyle Intervention or Metformin." The New England Journal of Medicine, 2002, vol. 346, No. 6, pp. 393-403.

(56) References Cited

OTHER PUBLICATIONS

Komori, Kiyoshi., "Treatment of Diabetes in Patients for Whom Metforming Treatment is Not Appropriate" Modern Physician (2008) vol. 28, No. 2 pp. 163-165.
Konstantinou, D. M. et al., "Pathophysiology-based novel pharmacotherapy for heart failure with preserved ejection fraction." Pharmacology & Therapeutics, 2013, vol. 140, No. 2, pp. 156-166.
Korom, S. et al; Inhibition of CD26/dipeptidyl peptidase IV activity in vivo prolongs cardiac allograft survival in rat recipients1,2, Transplantation, May 27, 1997, vol. 63, No. 10, pp. 1495-1500.
Kroller-Schön, S. et al., "Glucose-independent Improvement of Vascular Dysfunction in Experimental Sepsis by Dipeptidyl Peptidase-4 Inhibition." Cardiovascular Research, 2012, vol. 96, No. 1, pp. 140-149.
Kumar, V. et al., "Maillard Reaction and Drug Stability." Maillard Reactions in Chemistry, Food, and Health, 1994, No. 151, pp. 20-27.
Kuno, Y. et al., "Effect of the type of lubricant on the characteristics of orally disintegrating tablets manufactured using the phase transition of sugar alcohol." European Journal of Pharmaceutics and Biopharmaceutics, 2008, vol. 69, pp. 986-992.
Lachman, L. et al., "The Theory and Practice of Industrial Pharmacy." Varghese Publishing House, Third Edition, 1987, pp. 190-194.
Lakatos, P. L. et al., "Elevated Serum Dipeptidyl IV (CD26, EC 3.4.14.5) Activity in Experimental Liver Cirrhosis." European Journal of Clinical Investigation, 2000, vol. 30, No. 9, pp. 793-797.
Lakatos P. L. et al. "Elevated serum dipeptidyl peptidase IV (CD26, EC 3.4.14.5) activity in patients with primary biliary cirrhosis." Journal of Hepatol, 1999, vol. 30, p. 740.
Lambier, A.M. et al., Dipeptidyl-Peptidase IV from Bench to Bedside: An Update on Structural Properties, Functions, and Clinical Aspects of the Enzyme DPP IV. Critical Reviews in Clinical Laboratory Sciences, 2003, 40(3), p. 209-294.
Lee Jones, K. et al., "Effect of Metformin in Pediatric Patients With Type 2 Diabetes." Diabetes Care, 2002, vol. 25, No. 1, pp. 89-94.
Leibovitz, E. et al., "Sitagliptin pretreatment in diabetes patients presenting with acute coronary syndrome: results from the Acute Coronary Syndrome Israeli Survey (ACSIS)." Cardiovascular Diabetology, 2013, vol. 12, No. 1, pp. 1-7.
Levien, T.L. et al, "New drugs in development for the treatment of diabetes", Diabetes Spectrum, American Diabetes Association, US, vol. 22, No. 2, Jan. 1, 2009, pp. 92-106.
Lieberman, H. et al., "Pharmaceutical Dosage Forms." Marcel Dekker, Inc., 1980, vol. 1, p. 38.
Lim, S. et al., "Effect of a Dipeptidyl Peptidase-IV Inhibitor, Des-Fluoro-Sitagliptin, on Neointimal Formation after Balloon Injury in Rats." Plos One, 2012, vol. 7, No. 4, pp. 1-11.
Linagliptin Monograph, Published by VACO PBM-SHG US Veteran's Administration, 2011, pp. 1-17.
Lindsay, J.R. et al., "Inhibition of dipeptidyl peptidase IV activity by oral metformin in Type 2 diabetes." Diabetic Medicine, 2005, vol. 22, pp. 654-657.
Lovshin, J.A. et al., "Incretin-based therapies for type 2 diabetes mellitus." Nature Reviews Endocrinology, 2009, vol. 5, pp. 262-269.
Lu, "High prevlaence of albuminuria in population based patients diagnosed with type 2 diabetes in the Shanghai downtown", Diabestes Research and Clinical Practice (2007) 184-192.
Lyssenko, V. et al., "Mechanisms by which common variants in the TCF7L2 gene increase risk of type 2 diabetes." The Journal of Clinical Investigation, 2007, vol. 117, No. 8, pp. 2155-2163.
March, J. "Advanced Organic Chemistry: Reactions, Mechanisms, and Structure". Fourth Edition, 1992, pp. 652-653.
Mathieu C. et al., "Antihyperglycaemic therapy in elderly patients with type 2 diabetes: potential tole of incretin mimetics and DPP-4 inhibitors." International Journal of Clinical Practice, 2007, vol. 61, Suppl. 154, pp. 29-37.

Hansen, European Journal of Pharmacology, "The DPP-IV inhibitor linagliptin and GLP-1 induce synergistic effects on body weight loss and appetite suppression in the diet-induced obese rat", 2014, p. 254-263.
Ferreira, Triple Combination therapy with sitagliptin, metformin and rosiglitazone improves glycaemic control in patiens with type 2 diabetes, Diabetologixa, 2008, Suppl 1.
Byrn, Pharmaceutical Solids, A Strategic Approach to Regulatory Considerations, Pharmaceutical Research, 1995, vol. 12.
Morhenn (2), Keratinocyte proliferation in wound healing and skin diseases, Immunology Today, vol. 9, 1994.
Diabetes, Type 1 Diabetes-Associated Autoantibodies, 2009, vol. 52, Issue 8, p. 675-677.
Merck manual, 18th Edition, published Apr. 25, 2007, p. 594-598, Japanese Edition.
Scientific Discussion on Sifrol, EMEA, 2005, p. 1-9.
Scientific Discussion for Sifrol, European Public Assessment Reports, 2005, p. 1.
The Textbook of Pharmaceutics, Pharmcaeutical Subcommitee Hanrimwon, 2005, p. 1-6.
Mettler Toledo "interpreting DSC curves Part 1: Dynamic Measurements" Jan. 2000. Available from www.masointechnology.ie.x/Usercom_11.pdf.
Glucophage (metformin hydrocholoride tablets) revised label, 2003.
Stahl, Selected Procedures for the Preparation of Pharmaceutically Acceptable salts, Handbook of Pharmaceutical Salts Properties, Chapter 11, 2015.
Caira, Crystalline Polymorphism of Organic Compounds, Topics in Current Chemistry, vol. 198, 2015.
Brittain, Polymorphism on Pharmaceutical Solids, Chapter 5 Generation of Polymorphs, vol. 95, 1999, p. 183-226.
Luo, Theory and Practice of Modern Physical Pharmacy, Shangai Scientific and Technical Literature Publishing House, 2005, p. 294.
Thomas, (R)-8-Amino-piperidin-1-yl)-7-but-2-ynyl-3-methyl-1-(4-methyl-quinazolin-2-ylmethyl)-3,7-dihydro-purine-2,6-dione(BI1236, a Novel Xanthine based Dipeptidyl Peptidase 4 inhibitor, has a Superior Potency and longer duration of action compared with other dipeptyl Peptidase-4 inhibitors, The Journal of Pharmacology and Experimental Therapeutica, vol. 325, 2008, p. 175-182.
Kim, Comparison of DPP-4 Inhibitors, The Journal of Korean Diabetes, http:dx.doi.org/10.4093/jkd.2013.14.3.111.
Medicine Department of Pharmacy, Pharmaceutical Subcommitte, Book Publishing Harwinton, 1996, p. 283.
Huang, et al. Elimination of metformin-croscarmellose sodium interaction by competition, International Journal of Pharmaceutics, 2006, p. 33-39.
Freeman, Initial Combination therapy for patients with type 2 diabetes mellitus, Drugs in Context, 2013, p. 212256.
Scheen, Efficacy and Safety of Jentadueto, Expert Opinion on Drug and Safety, vol. 12, No. 2, 2013, p. 275-289.
Haak, Initial Combination of linagliptin and metformin improves glycemic control in type 2 diabetes, Diabetes, Obesity and Metabolism, vol. 14, 2012, p. 565-574.
International Search Report and Written Opinion for PCT/EP2017/064007, dated Jun. 8, 2017.
Wikipedia, the free encyclopedia, The carbonyl group, 2017.
Controlling Temperature (Guidelines for the Storage of Essential Medicines and Other Health Commodities, 2003, http://apps.who.int.medicinedocs/en/d/Js4885e/6.5html).
Pharmaceutical Manufacturing and Storage (Concepts and Design, Inc.) 2009.
Methocel Cellulose Ethers in Aqueous Systems for tablet coating: retrieved from Internet: http://msdssearch.dow.com/PublishedLiteratureDOWCOM/dh_004a/0901b8038004ab56.pdf-?filepath=198-00755.pd?fromPage=GetDoc, published2002. Retrieved Dec. 8, 2017.
Wu, Reactive Impurities in Excipients-Profiling, American Association of Pharmaceutical Scientists, 2011, vol. 12, No. 4, p. 1248-1263.
Waterman, Accelerating aging-Prediction of Chemical Stability of Pharmaceuticals, International Journal of Pharmaceutics, 2005, vol. 293, p. 101-125.

(56) References Cited

OTHER PUBLICATIONS

Herman, The DP-IV inhibitor MK-0431 enhances active GLP-1 and reduces Glucose following an OGTT in Type 2 Diabetics, American Diabetes Asociation, 2004.
Kaur, Development of new incretin drugs: Promising Therapies, Indian Journal Pharmacology, 2006, vol. 38, Issue 2, p. 100-106.
Hu, Diabetes Mellitus and Cardiovascular Disease, People's Military Medical Press, 2005, p. 211.
Susman,Ada: Linagliptin Works in Diabetic Kidney Disease, Med Page Today, 2011.
Announcement of the approval of Novel oral Diabetes Drug JANUVIA, Press Release, 2006.
Okano, Renal Clearance, New General Pharmaceutics, Revised 3rd Edition, 1987 p. 213-215.
Clinical trials, A Randomized, Double Blind, Active Controlled parallel Group Efficacy and Safety Study of BI 1356 Compared to Glimepiride over 2 years in Type 2 Diabetic Patients with insufficient glycemic control despite metformin therapy, https://clinicaltrials.gov/archive/NCT00622284/20120606, 2008.
Eckhardt, "-(3-(R)-Aminopiperidin-1-yl)7-but-2-ynyl-3-methyl-1-(4-methyl-quinazolin-2-ylmethyl-3,7-dihydropurine-2,6-dione (BI 1356), a highly potent, selective, long-acting, and orally bioavailable DPP-4 inhibitor for the treatment of type 2 diabetes", J. med. Chem, vol. 50, 2007.
Shigai, "How to use medicines in case of kidney injury caused by medicine" Journal of the Japanese Association of Rural Medicine, vol. 51, 2002, p. 63-67.
Zeng, "Efficacy and Safety of linagliptin added to metformin and sulphonylurea in Chinese patients with type 2 diabetes: a sub-analysis of data from a randomised clinicial trial", Current Medical Research and Opinion, 2013.

* cited by examiner

DPP-IV INHIBITOR COMBINED WITH A FURTHER ANTIDIABETIC AGENT, TABLETS COMPRISING SUCH FORMULATIONS, THEIR USE AND PROCESS FOR THEIR PREPARATION

The present invention relates to pharmaceutical compositions comprising fixed dose combinations of a DPP-4 inhibitor drug and a partner drug, processes for the preparation thereof, and their use to treat certain diseases.

In a more detailed aspect, the present invention relates to oral solid dosage forms for fixed dose combination (FDC) of a selected dipeptidyl peptidase-4 (DPP-4) inhibitor drug and a certain partner drug. The FDC formulations are chemically stable and either a) display similarity of in-vitro dissolution profiles and/or are bioequivalent to the free combination, or b) allow to adjust the in-vitro and in-vivo performance to desired levels. In a preferred embodiment the invention relates to chemically stable FDC formulations maintaining the original dissolution profiles of corresponding mono tablets of each individual entity, with a reasonable tablet size.

The enzyme DPP-4 also known as CD26 is a serine protease known to lead to the cleavage of a dipeptide from the N-terminal end of a number of proteins having at their N-terminal end a prolin or alanin residue. Due to this property DPP-4 inhibitors interfere with the plasma level of bioactive peptides including the peptide GLP-1 and are considered to be promising drugs for the treatment of diabetes mellitus.

For example, DPP-4 inhibitors and their uses are disclosed in WO 2002/068420, WO 2004/018467, WO 2004/018468, WO 2004/018469, WO 2004/041820, WO 2004/046148, WO 2005/051950, WO 2005/082906, WO 2005/063750, WO 2005/085246, WO 2006/027204, WO 2006/029769 or WO2007/014886; or in WO 2004/050658, WO 2004/111051, WO 2005/058901, WO 2005/097798; WO 2006/068163, WO 2007/071738, WO 2008/017670; WO 2007/128721 or WO 2007/128761.

As further DPP-4 inhibitors the following compounds can be mentioned:

Sitagliptin (MK-0431) having the structural formula A below is (3R)-3-amino-1-[3-(trifluoromethyl)-5,6,7,8-tetrahydro-5H-[1,2,4]triazolo[4,3-a]pyrazin-7-yl]-4-(2,4,5-trifluorophenyl)butan-1-one, also named (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine,

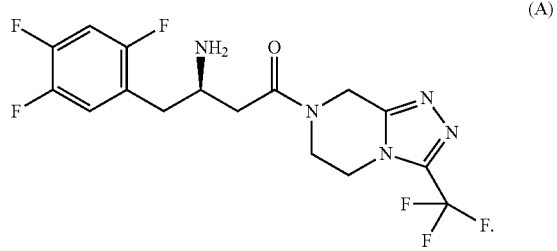 [SMILES: N[C@@H](CC(=O)N1CCn2c(nnc2C(F)(F)F)C1)Cc1cc(F)c(F)cc1F]

(A)

In one embodiment, sitagliptin is in the form of its dihydrogenphosphate salt, i.e. sitagliptin phosphate. In a further embodiment, sitagliptin phosphate is in the form of a crystalline anhydrate or monohydrate. A class of this embodiment refers to sitagliptin phosphate monohydrate.

Sitagliptin free base and pharmaceutically acceptable salts thereof are disclosed in U.S. Pat. No. 6,699,871 and in Example 7 of WO 03/004498. Crystalline sitagliptin phosphate monohydrate is disclosed in WO 2005/003135 and in WO 2007/050485.

For details, e.g. on a process to manufacture this compound or a salt thereof, reference is thus made to these documents.

Vildagliptin (LAF-237) having the structural formula B below is (2S)-{[(3-hydroxyadamantan-1-yl)amino]acetyl}pyrrolidine-2-carbonitrile, also named (S)-1-[(3-hydroxy-1-adamantyl)amino]acetyl-2-cyano-pyrrolidine,

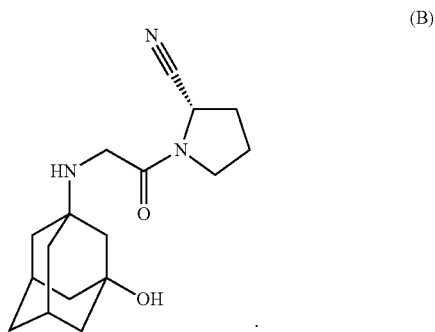 [SMILES: N#C[C@@H]1CCCN1C(=O)CNC12CC3CC(CC(O)(C3)C1)C2]

(B)

Vildagliptin is specifically disclosed in U.S. Pat. No. 6,166,063 and in Example 1 of WO 00/34241. Specific salts of vildagliptin are disclosed in WO 2007/019255. A crystalline form of vildagliptin is disclosed in WO 2006/078593. A crystalline form of vildagliptin is disclosed in WO 2006/078593.

For details, e.g. on a process to manufacture this compound or a salt thereof, reference is thus made to these documents.

Saxagliptin (BMS-477118) having the structural formula C below is (1S,3S,5S)-2-{(2S)-2-amino-2-(3-hydroxyadamantan-1-yl)acetyl}-2-azabicyclo[3.1.0]hexane-3-carbonitrile, also named (S)-3-hydroxyadamantylglycine-L-cis-4,5-methanoprolinenitrile,

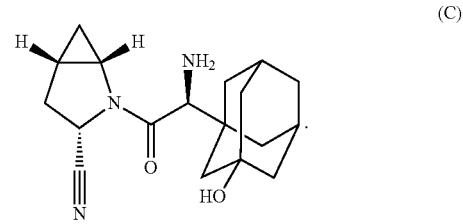 [SMILES: N#C[C@@H]1C[C@@H]2C[C@@H]2N1C(=O)[C@@H](N)C12CC3CC(CC(O)(C3)C1)C2]

(C)

Saxagliptin is specifically disclosed in U.S. Pat. No. 6,395,767 and in Example 60 of WO 01/68603. In one embodiment, saxagliptin is in the form of its HCl salt or its mono-benzoate salt as disclosed in WO 2004/052850. In a further embodiment, saxagliptin is in the form of the free base. In a yet further embodiment, saxagliptin is in the form of the monohydrate of the free base as disclosed in WO 2004/052850. Crystalline forms of the HCl salt and the free base of saxagliptin are disclosed in WO 2008/131149. A process for preparing saxagliptin is also disclosed in WO 2005/106011 and WO 2005/115982.

For details, e.g. on a process to manufacture this compound or a salt thereof, reference is thus made to these documents.

Denagliptin (GSK-823093) having the structural formula D below is (2S,4S)-1-[(2S)-2-amino-3,3-bis(4-fluorophenyl)propionyl]-4-fluoropyrrolidine-2-carbonitrile, also named (2S,4S)-4-fluoro-1-[4-fluoro-beta-(4-fluorophenyl)-L-phenylalanyl]-2-pyrrolidinecarbonitrile (D)

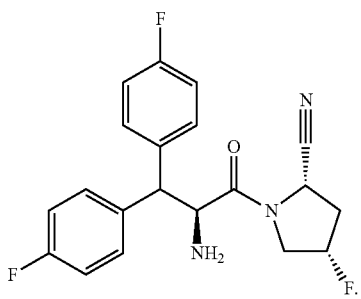

Denagliptin is specifically disclosed in U.S. Pat. No. 7,132,443 and in WO 03/002531. In one embodiment, denagliptin is in the form of its hydrochloride salt as disclosed in Example 2 of WO 03/002531 or its tosylate salt as disclosed in WO 2005/009956. A class of this embodiment refers to denagliptin tosylate. Crystalline anhydrous denagliptin tosylate is disclosed in WO 2005/009956.

For details, e.g. on a process to manufacture this compound or a salt thereof, reference is thus made to these documents.

Alogliptin (SYR-322) having the structural formula E below is 2-({6-[(3R)-3-aminopiperidin-1-yl]-3-methyl-2,4-dioxo-3,4-dihydro-2H-pyrimidin-1-yl}methyl)benzonitrile (E)

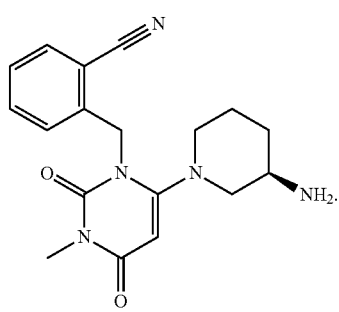

Alogliptin is specifically disclosed in US 2005/261271, EP 1586571 and in WO 2005/095381. In one embodiment, alogliptin is in the form of its benzoate salt, its hydrochloride salt or its tosylate salt each as disclosed in WO 2007/035629. A class of this embodiment refers to alogliptin benzoate. Polymorphs of alogliptin benzoate are disclosed in WO 2007/035372. A process for preparing alogliptin is disclosed in WO 2007/112368 and, specifically, in WO 2007/035629.

For details, e.g. on a process to manufacture this compound or a salt thereof, reference is thus made to these documents.

(S)-1-((2S,3S,11bS)-2-Amino-9,10-dimethoxy-1,3,4,7,11b-hexahydro-2H-pyrido[2,1-a]isoquinolin-3-yl)-4-fluoromethyl-pyrrolidin-2-one or a pharmaceutically acceptable salt thereof:

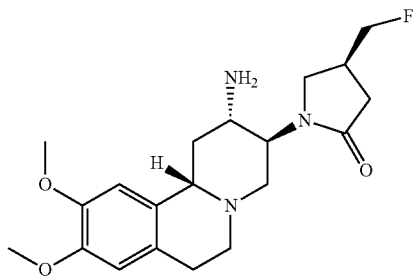 [SMILES: COc1cc2c(cc1OC)[C@@H]1C[C@H](N)[C@@H](N3C[C@@H](CF)CC3=O)CN1CC2]

This compound and methods for its preparation are disclosed in WO 2005/000848. A process for preparing this compound (specifically its dihydrochloride salt) is also disclosed in WO 2008/031749, WO 2008/031750 and WO2008/055814.

For details, e.g. on a process to manufacture this compound or a salt thereof, reference is thus made to these documents.

(R)-2-[6-(3-Amino-piperidin-1-yl)-3-methyl-2,4-dioxo-3,4-dihydro-2H-pyrimidin-1-ylmethyl]-4-fluoro-benzonitrile or a pharmaceutically acceptable salt thereof:

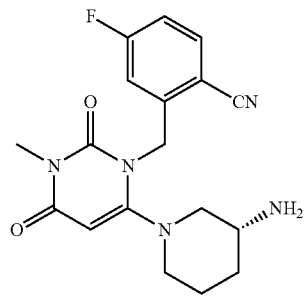 [SMILES: Cn1c(=O)cc(N2CCC[C@@H](N)C2)n(Cc2cc(F)ccc2C#N)c1=O]

This compound and methods for its preparation and use are disclosed in WO 2005/095381, US 2007060530, WO 2007/033350, WO 2007/035629, WO 2007/074884, WO 2007/112368 and WO 2008/033851. Specifically claimed salts include the succinate (WO 2008/067465), benzoate, benzenesulfonate, p-toluenesulfonate, (R)-mandelate and hydrochloride. For details, e.g. on a process to manufacture this compound or a salt thereof, reference is thus made to these documents.

Partner drugs to be combined with the DPP-4 inhibitors within the pharmaceutical compositions according to this invention are biguanides (e.g. metformin such as metformin hydrochloride), thiazolidinones (e.g. pioglitazone such as pioglitazone hydrochloride), statines (e.g. atorvastatin) or ARBs (e.g. telmisartan).

The biguanide antihyperglycemic agent metformin is disclosed in U.S. Pat. No. 3,174,901. The preparation of metformin (dimethyldiguanide) and its hydrochloride salt is state of the art and was disclosed first by Emil A. Werner and James Bell, J. Chem. Soc. 121, 1922, 1790-1794. Other pharmaceutically acceptable salts of metformin can be found in U.S. application Ser. No. 09/262,526 filed Mar. 4, 1999 or U.S. Pat. No. 3,174,901. It is preferred that the metformin employed herein be the metformin hydrochloride salt.

Unless specifically noted, in the present context the terms "DPP-4 inhibitor(s)", "biguanide(s)", "thiazolidinone(s)", "statine(s)", "ARB(s)", or any species thereof like "metformin", "pioglitazone", are also intended to comprise any pharmaceutically acceptable salt thereof, crystal form, hydrate, solvate, diastereomer or enantiomer thereof.

For avoidance of any doubt, the disclosure of each of the foregoing documents cited above is specifically incorporated herein by reference in its entirety.

In attempts to prepare pharmaceutical compositions of selected DPP-4 inhibitors it has been observed, that the DPP-4 inhibitors with a primary or secondary amino group show incompatibilities, degradation problems, or extraction problems with a number of customary excipients such as microcrystalline cellulose, sodium starch glycolate, croscarmellose sodium, tartaric acid, citric acid, glucose, fructose, saccharose, lactose, maltodextrines. Though the compounds themselves are very stable, they react with incompatible partner drug, or its impurity product, and/or with many excipients used in solid dosage forms and with impurities of excipients, especially in tight contact provided in tablets and at high excipient/drug ratios. The amino group appears to react with reducing sugars and with other reactive carbonyl groups and with carboxylic acid functional groups formed for example at the surface of microcrystalline cellulose by oxidation. These unforeseen difficulties are primarily observed in low dosage ranges of the DPP-4 inhibitor used, which are required due to their surprising potency, and/or high dosage ranges of the partner drug used. Thus, pharmaceutical compositions are required to solve these technical problems, which may be associated with the unexpected potency of selected DPP-4 inhibitor compounds.

Other aims of the present invention will become apparent to the skilled man from the foregoing and following remarks.

It has now been found that the pharmaceutical compositions, which are described in greater details herein, have surprising and particularly advantageous properties.

In particular, it has been found that by the use of a nucleophilic and/or basic agent, which may be suitable for stabilizing, such as e.g. a suitable buffering agent as stabilizer, within these pharmaceutical compositions one can overcome these problems, e.g. of incompatibility and poor stability, especially decomposition and/or "assay decrease" which may be caused e.g. by reaction (e.g. by acylation, urea formation or Maillard reaction, or the like) of free base type DPP-4 inhibitors when combined with an incompatible partner drug, or its impurity product and/or a pharmaceutical excipient having such functional group (such as a reducing end of a sugar or an acyl group, such as e.g. an acetyl or carbamoyl group) to form derivatives with the free base type DPP-4 inhibitors, such as e.g. N-acetyl or N-carbamoyl derivatives. Therefore, by the use of a suitable nucleophilic and/or basic agent (e.g. a buffering and/or pH modifying agent) within these pharmaceutical compositions protection against decomposition and degradation can be achieved.

Thus, the present invention is directed to a chemically stable FDC formulation comprising a DPP-4 inhibitor, a partner drug, and a nucleophilic and/or basic agent.

Thus, the present invention is also directed to a chemically stable FDC formulation comprising a DPP-4 inhibitor, a partner drug, and a suitable buffering agent.

Thus, the present invention is also directed to a chemically stable FDC formulation comprising a DPP-4 inhibitor, a partner drug, and a pH modifying agent.

A DPP-4 inhibitor within the meaning of the present invention includes, without being limited to, any of those DPP-4 inhibitors mentioned hereinabove and hereinbelow, preferably orally active DPP-4 inhibitors.

In a closer embodiment, a DPP-4 inhibitor within the meaning of the present invention includes a DPP-4 inhibitor with an amino group, especially a free or primary amino group.

In a yet closer embodiment, a DPP-4 inhibitor in the context of the present invention is a DPP-4 inhibitor with a primary amino group, particularly with a free primary amino group.

The partner drug used is selected from the group consisting of a biguanide (e.g. metformin such as metformin hydrochloride), a thiazolidinone (e.g. pioglitazone such as pioglitazone hydrochloride), a statine (e.g. atorvastatin) and an ARB (e.g. telmisartan). A preferred partner drug within the meaning of this invention is metformin, particularly metformin hydrochloride (1,1-dimethylbiguanide hydrochloride or metformin HCl).

The buffering agent used may be a basic amino acid, which has an intramolecular amino group and alkaline characteristics (isoelectric point, pI: 7.59-10.76), such as e.g. L-arginine, L-lysine or L-histigine. A preferred buffering agent within the meaning of this invention is L-arginine. L-Arginine has a particular suitable stabilizing effect on the compositions of this invention, e.g. by suppressing degradation of the DPP-4 inhibitor in the presence of the partner drug.

The present invention is directed to a pharmaceutical comprising a DPP-4 inhibitor, a partner drug, a nucleophilic and/or basic agent, and one or more pharmaceutical excipients.

The present invention is also directed to a pharmaceutical composition comprising a DPP-4 inhibitor, a partner drug, a suitable buffering agent, and one or more pharmaceutical excipients.

The present invention is also directed to a pharmaceutical comprising a DPP-4 inhibitor, a partner drug, a pH modifying agent, and one or more pharmaceutical excipients.

In an embodiment, the present invention is directed to a pharmaceutical composition (e.g. an oral solid dosage form, particularly a tablet) comprising a DPP-4 inhibitor; a partner drug (particularly metformin); and L-arginine for stabilizing the composition and/or the DPP-4 inhibitor, particularly against chemical degradation; as well as one or more pharmaceutical excipients.

In another embodiment, the present invention is directed to a pharmaceutical composition (e.g. an oral solid dosage form, particularly a tablet) obtainable from a DPP-4 inhibitor; a partner drug (particularly metformin); and L-arginine for stabilizing the composition and/or the DPP-4 inhibitor, particularly against chemical degradation; as well as one or more pharmaceutical excipients.

In general, pharmaceutical excipients which may be used may be selected from the group consisting of one or more fillers, one or more binders or diluents, one or more lubricants, one or more disintegrants, and one or more glidants, one or more film-coating agents, one or more plasticizers, one or more pigments, and the like.

The pharmaceutical compositions (tablets) of this invention comprise usually a binder.

In more detail, the pharmaceutical compositions (tablets) of this invention comprise usually one or more fillers (e.g. D-mannitol, corn starch and/or pregelatinized starch), a binder (e.g. copovidone), a lubricant (e.g. magnesium stearate), and a glidant (e.g. colloidal anhydrous silica).

Suitably the pharmaceutical excipients used within this invention are conventional materials such as D-mannitol, corn starch, pregelatinized starch as a filler, copovidone as a binder, magnesium stearate as a lubricant, colloidal anhydrous silica as a glidant, hypromellose as a film-coating agent, propylene glycol as a plasticizer, titanium dioxide, iron oxide red/yellow as a pigment, and talc, etc.

A typical composition according to the present invention comprises the binder copovidone (also known as copolyvidone or Kollidon VA64).

Further, a typical composition according to the present invention comprises the filler corn starch, the binder copovidone, the lubricant magnesium stearate, and the glidant colloidal anhydrous silica.

A pharmaceutical composition according to an embodiment of the present invention is intended for the treatment of diabetes and/or to achieve glycemic control in a type 1 or type 2 diabetes mellitus patient and comprises a fixed dose combination formulation as described herein together with suitable pharmaceutical excipients. Additionally the compositions can be used to treat rheumatoid arthritis, obesity and osteoporosis as well as to support allograft transplantation.

Thus, in particular, the present invention is directed to a pharmaceutical composition (especially an oral solid dosage form, particularly a tablet) comprising a DPP-4 inhibitor, metformin hydrochloride, L-arginine and one or more pharmaceutical excipients, particularly one or more fillers, one or more binders, one or more glidants, and/or one or more lubricants.

In more particular, the present invention is directed to a pharmaceutical composition (especially an oral solid dosage form, particularly a tablet) comprising a DPP-4 inhibitor, metformin hydrochloride, L-arginine, copovidone as binder and one or more further pharmaceutical excipients.

Typical pharmaceutical compositions of this invention may comprise in the DPP-4 inhibitor portion 0.1-10% L-arginine (such as e.g. about 0.1%, 0.25%, 0.556%, 2.12%, 2.22% or 10%) by weight of total DPP-4 inhibitor portion, particularly about 2% (e.g. more specifically, 2.12% by weight of total tablet core of uncoated monolayer tablet).

Typical pharmaceutical compositions of this invention may comprise in the DPP-4 inhibitor portion (% by weight of total DPP-4 inhibitor portion):

0.2-10% DPP-4 inhibitor, and
0.1-10% L-arginine.

Typical pharmaceutical compositions of this invention may comprise the DPP-4 inhibitor and L-arginine in a weight ratio of from about 1:20 to about 10:1 or from about 1:15 to about 10:1 or from about 1:10 to about 10:1, especially from 1:10 to 5:2, such as e.g. in a weight ratio of 1:10, 1:8.5, 1:5, 1:1, or 1:0.4, more detailed in a weight ratio of 2.5 mg:25 mg, 2.5 mg:21.2 mg, 2.5 mg:12.5 mg, 2.5 mg:2.5 mg, or 2.5 mg:1 mg.

Typical pharmaceutical compositions of this invention may comprise metformin hydrochloride and L-arginine in a weight ratio of from about 40:1 to about 1000:1, such as e.g. in a weight ratio of 40:1, 200:1, 340:1, 400:1, 500:1, 850:1, or 1000:1, more detailed in a weight ratio of 500 mg:12.5 mg, 850 mg:21.2 mg, 1000 mg:25 mg, 500 mg:2.5 mg, 850 mg:2.5 mg, 1000 mg:2.5 mg, 500 mg:1 mg, 850 mg:1 mg, or 1000 mg:1 mg.

Typical pharmaceutical compositions of this invention may comprise the DPP4-inhibitor, metformin hydrochloride and L-arginine in a weight ratio of from about 1:200:0.4 to about 1:200:5 (e.g. 1:200:0.4, 1:200:1, 1:200:5), or from about 1:340:0.4 to about 1:340:8.5 (e.g. 1:340:0.4, 1:340:1, 1:340:8.5), or from about 1:400:0.4 to about 1:400:10 (e.g. 1:400:0.4, 1:400:1, 1:400:10).

Typical pharmaceutical compositions of this invention may comprise one or more of the following amounts (% by weight of total coated tablet mass):

0.1-0.5% DPP-4 inhibitor,
47-85% metformin HCl,
0.07-2.2% L-arginine,
3.9-8.1% binder (e.g. copovidone),
2.3-5.9% filler 1 (e.g. corn starch),
0-4.4% filler 2 (e.g. pregelatinized starch),
0-33% filler 3 (e.g. D-mannitol),
0.7-1.5% lubricant (e.g. magnesium stearate), and
0.1-0.5% glidant (e.g. colloidal anhydrous silica).

Further details about the FDC formulations of this invention, e.g. the ingredients, ratio of ingredients (such as e.g. ratio of DPP-4 inhibitor, metformin hydrochloride, L-arginine and/or excipients), particularly with respect to special dosage forms (tablets) used within this invention as well as their preparation, become apparent to the skilled person from the disclosure hereinbefore and hereinafter (including by way of example the following examples as well as the claims).

In a first embodiment (embodiment A), a DPP-4 inhibitor in the context of the present invention is any DPP-4 inhibitor of formula (I)

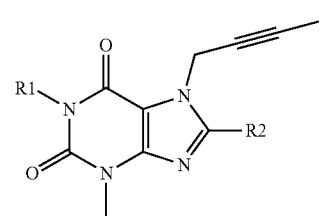

or formula (II)

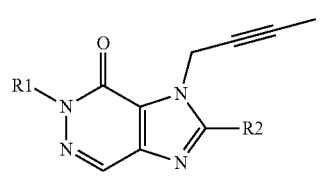

or formula (III)

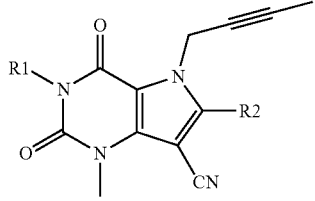

wherein R1 denotes ([1,5]naphthyridin-2-yl)methyl, (quinazolin-2-yl)methyl, (quinoxalin-6-yl)methyl, (4-methyl-quinazolin-2-yl)methyl, 2-cyano-benzyl, (3-cyano-quinolin-2-yl)methyl, (3-cyano-pyridin-2-yl)methyl, (4-methyl-pyrimidin-2-yl)methyl, or (4,6-dimethyl-pyrimidin-2-yl)methyl and R2 denotes 3-(R)-amino-piperidin-1-yl, (2-amino-2-methyl-propyl)-methylamino or (2-(S)-amino-propyl)-methylamino, or its pharmaceutically acceptable salt;

In a second embodiment (embodiment B), a DPP-4 inhibitor in the context of the present invention is a DPP-4 inhibitor selected from the group consisting of sitagliptin, vildagliptin, saxagliptin and alogliptin, or its pharmaceutically acceptable salt.

Regarding the first embodiment (embodiment A), preferred DPP-4 inhibitors are any or all of the following compounds and their pharmaceutically acceptable salts:

1-[(4-methyl-quinazolin-2-yl)methyl]-3-methyl-7-(2-butyn-1-yl)-8-(3-(R)-amino-piperidin-1-yl)-xanthine (compare WO 2004/018468, example 2(142):

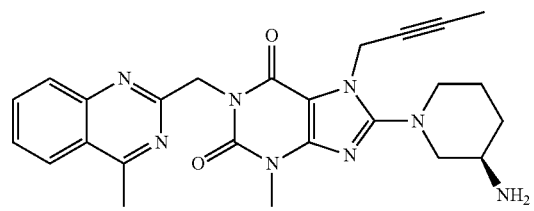 [SMILES: CC#CCn1c(N2CCC[C@@H](N)C2)nc2c1c(=O)n(Cc1nc(C)c3ccccc3n1)c(=O)n2C]

1-[([1,5]naphthyridin-2-yl)methyl]-3-methyl-7-(2-butyn-1-yl)-8-((R)-3-amino-piperidin-1-yl)-xanthine (compare WO 2004/018468, example 2(252)):

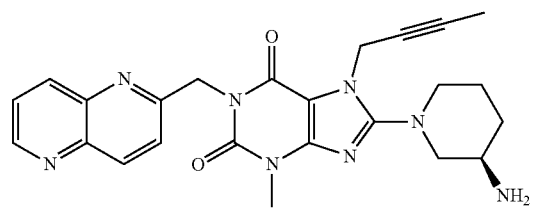 [SMILES: CC#CCn1c(N2CCC[C@@H](N)C2)nc2c1c(=O)n(Cc1ccc3ncccc3n1)c(=O)n2C]

1-[(Quinazolin-2-yl)methyl]-3-methyl-7-(2-butyn-1-yl)-8-((R)-3-amino-piperidin-1-yl)-xanthine (compare WO 2004/018468, example 2(80)):

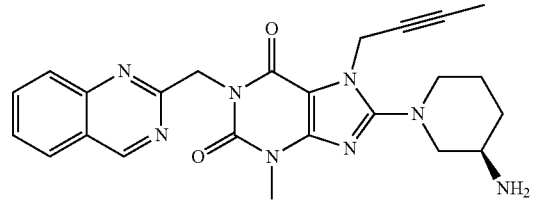 [SMILES: CC#CCn1c(N2CCC[C@@H](N)C2)nc2c1c(=O)n(Cc1ncc3ccccc3n1)c(=O)n2C]

2-((R)-3-Amino-piperidin-1-yl)-3-(but-2-yinyl)-5-(4-methyl-quinazolin-2-ylmethyl)-3,5-dihydro-imidazo[4,5-d]pyridazin-4-one (compare WO 2004/050658, example 136):

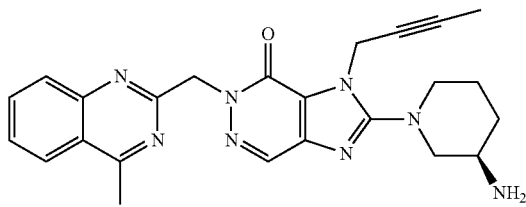 [SMILES: CC#CCn1c(N2CCC[C@@H](N)C2)nc2cnn(Cc3nc(C)c4ccccc4n3)c(=O)c21]

1-[(4-Methyl-quinazolin-2-yl)methyl]-3-methyl-7-(2-butyn-1-yl)-8-[(2-amino-2-methyl-propyl)-methylamino]-xanthine (compare WO 2006/029769, example 2(1)):

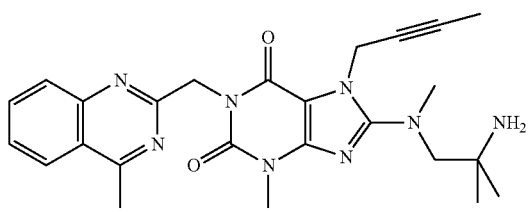 [SMILES: CC#CCn1c(N(C)CC(C)(C)N)nc2c1c(=O)n(Cc1nc(C)c3ccccc3n1)c(=O)n2C]

1-[(3-Cyano-quinolin-2-yl)methyl]-3-methyl-7-(2-butyn-1-yl)-8-((R)-3-amino-piperidin-1-yl)-xanthine (compare WO 2005/085246, example 1(30)):

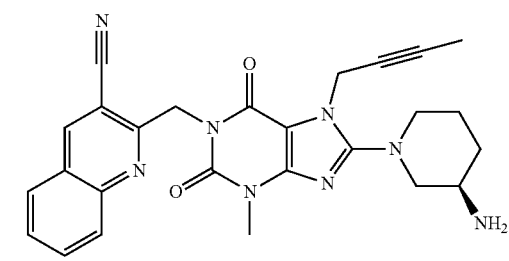 [SMILES: CC#CCn1c(N2CCC[C@@H](N)C2)nc2c1c(=O)n(Cc1nc3ccccc3cc1C#N)c(=O)n2C]

1-(2-Cyano-benzyl)-3-methyl-7-(2-butyn-1-yl)-8-((R)-3-amino-piperidin-1-yl)-xanthine (compare WO 2005/085246, example 1(39)):

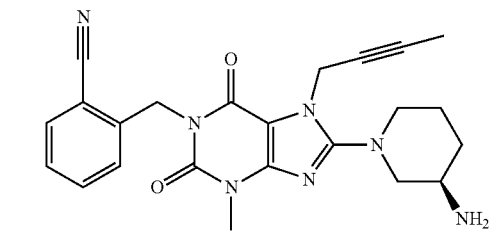 [SMILES: CC#CCn1c(N2CCC[C@@H](N)C2)nc2c1c(=O)n(Cc1ccccc1C#N)c(=O)n2C]

1-[(4-Methyl-quinazolin-2-yl)methyl]-3-methyl-7-(2-butyn-1-yl)-8-[(S)-(2-amino-propyl)-methylamino]-xanthine (compare WO 2006/029769, example 2(4)):

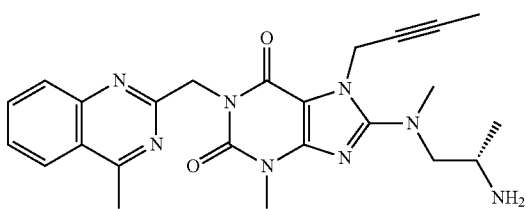 [SMILES: CC#CCn1c(N(C)C[C@H](C)N)nc2c1c(=O)n(Cc1nc(C)c3ccccc3n1)c(=O)n2C]

1-[(3-Cyano-pyridin-2-yl)methyl]-3-methyl-7-(2-butyn-1-yl)-8-((R)-3-amino-piperidin-1-yl)-xanthine (compare WO 2005/085246, example 1(52)):

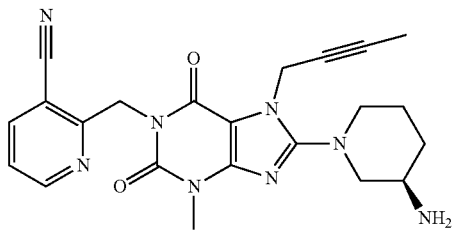 [SMILES: CC#CCn1c(N2CCC[C@@H](N)C2)nc2c1c(=O)n(Cc1ncccc1C#N)c(=O)n2C]

1-[(4-Methyl-pyrimidin-2-yl)methyl]-3-methyl-7-(2-butyn-1-yl)-8-((R)-3-amino-piperidin-1-yl)-xanthine (compare WO 2005/085246, example 1(81)):

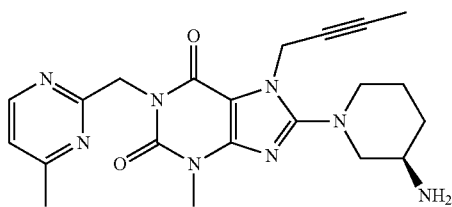 [SMILES: CC#CCn1c(N2CCC[C@@H](N)C2)nc2c1c(=O)n(Cc1nccc(C)n1)c(=O)n2C]

1-[(4,6-Dimethyl-pyrimidin-2-yl)methyl]-3-methyl-7-(2-butyn-1-yl)-8-((R)-3-amino-piperidin-1-yl)-xanthine (compare WO 2005/085246, example 1(82)):

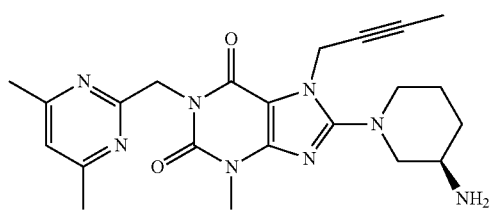 [SMILES: CC#CCn1c(N2CCC[C@@H](N)C2)nc2c1c(=O)n(Cc1nc(C)cc(C)n1)c(=O)n2C]

1-[(Quinoxalin-6-yl)methyl]-3-methyl-7-(2-butyn-1-yl)-8-((R)-3-amino-piperidin-1-yl)-xanthine (compare WO 2005/085246, example 1(83)):

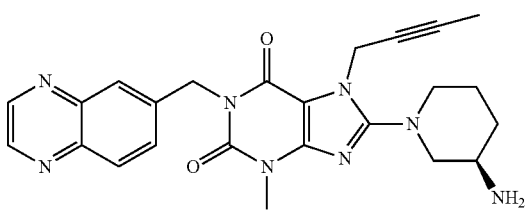 [SMILES: CC#CCn1c(N2CCC[C@@H](N)C2)nc2c1c(=O)n(Cc1ccc3nccnc3c1)c(=O)n2C]

These DPP-4 inhibitors are distinguished from structurally comparable DPP-4 inhibitors, as they combine exceptional potency and a long-lasting effect with favourable pharmacological properties, receptor selectivity and a favourable side-effect profile or bring about unexpected therapeutic advantages or improvements when combined with other pharmaceutical active substances. Their preparation is disclosed in the publications mentioned.

A more preferred DPP-4 inhibitor among the abovementioned DPP-4 inhibitors of embodiment A of this invention is 1-[(4-methyl-quinazolin-2-yl)methyl]-3-methyl-7-(2-butyn-1-yl)-8-(3-(R)-amino-piperidin-1-yl)-xanthine, particularly the free base thereof (which is also known as BI 1356).

Regarding the second embodiment (embodiment B), preferred DPP-4 inhibitors are selected from the group consisting of vildagliptin, saxagliptin and alogliptin, and their pharmaceutically acceptable salts.

Unless otherwise noted, according to this invention it is to be understood that the definitions of the above listed DPP-4 inhibitors also comprise their pharmaceutically acceptable salts as well as hydrates, solvates and polymorphic forms thereof. With respect to salts, hydrates and polymorphic forms thereof, particular reference is made to those which are referred to hereinabove and hereinbelow.

With respect to embodiment A, the methods of synthesis for the DPP-4 inhibitors according to embodiment A of this invention are known to the skilled person. Advantageously, the DPP-4 inhibitors according to embodiment A of this invention can be prepared using synthetic methods as described in the literature. Thus, for example, purine derivatives of formula (I) can be obtained as described in WO 2002/068420, WO 2004/018468, WO 2005/085246, WO 2006/029769 or WO 2006/048427, the disclosures of which are incorporated herein. Purine derivatives of formula (II) can be obtained as described, for example, in WO 2004/050658 or WO 2005/110999, the disclosures of which are incorporated herein. Purine derivatives of formula (III) can be obtained as described, for example, in WO 2006/068163, WO 2007/071738 or WO 2008/017670, the disclosures of which are incorporated herein. The preparation of those DPP-4 inhibitors, which are specifically mentioned hereinabove, is disclosed in the publications mentioned in connection therewith. Polymorphous crystal modifications and formulations of particular DPP-4 inhibitors are disclosed in WO 2007/128721 and WO 2007/128724, respectively, the disclosures of which are incorporated herein in their entireties.

With respect to embodiment B, the methods of synthesis for the DPP-4 inhibitors of embodiment B are described in the scientific literature and/or in published patent documents, particularly in those cited herein.

With respect to the first embodiment (embodiment A), the dosage typically required of the DPP-4 inhibitors mentioned herein in embodiment A when administered orally is 0.5 mg to 100 mg, preferably 2.5 mg to 50 mg or 0.5 mg to 10 mg, more preferably 2.5 mg to 10 mg or 1 mg to 5 mg, in each case 1 to 4 times a day. Thus, the dosage required of 1-[(4-methyl-quinazolin-2-yl)methyl]-3-methyl-7-(2-butyn-1-yl)-8-(3-(R)-amino-piperidin-1-yl)-xanthine when administered orally is 0.5 mg to 10 mg per patient per day, preferably 2.5 mg to 10 mg or 1 mg to 5 mg per patient per day.

A dosage form prepared with a pharmaceutical composition comprising a DPP-4 inhibitor mentioned herein in embodiment A contain the active ingredient in a dosage range of 0.1-100 mg, in particular 0.5 to 10 mg. Thus, particular dosage strengths of 1-[(4-methyl-quinazolin-2-yl)

methyl]-3-methyl-7-(2-butyn-1-yl)-8-(3-(R)-amino-piperidin-1-yl)-xanthine are 0.5 mg, 1 mg, 2.5 mg, 5 mg and 10 mg. A more particular unit dosage strength of 1-[(4-methyl-quinazolin-2-yl)methyl]-3-methyl-7-(2-butyn-1-yl)-8-(3-(R)-amino-piperidin-1-yl)-xanthine for inclusion into fixed dose combination pharmaceutical compositions of the present invention is 2.5 mg.

With respect to the second embodiment (embodiment B), the doses of DPP-4 inhibitors mentioned herein in embodiment B to be administered to mammals, for example human beings, of, for example, approximately 70 kg body weight, may be generally from about 0.5 mg to about 350 mg, for example from about 10 mg to about 250 mg, preferably 20-200 mg, more preferably 20-100 mg, of the active moiety per person per day, or from about 0.5 mg to about 20 mg, preferably 2.5-10 mg, per person per day, divided preferably into 1 to 4 single doses which may, for example, be of the same size. Single dosage strengths comprise, for example, 2.5, 5, 10, 25, 40, 50, 75, 100, 150 and 200 mg of the DPP-4 inhibitor active moiety.

A dosage strength of the DPP-4 inhibitor sitagliptin is usually between 25 and 200 mg of the active moiety. A recommended dose of sitagliptin is 100 mg calculated for the active moiety (free base anhydrate) once daily. Unit dosage strengths of sitagliptin free base anhydrate (active moiety) are 25, 50, 75, 100, 150 and 200 mg. Particular unit dosage strengths of sitagliptin (e.g. per tablet) are 25, 50 and 100 mg. An equivalent amount of sitagliptin phosphate monohydrate to the sitagliptin free base anhydrate is used in the pharmaceutical compositions, namely, 32.13, 64.25, 96.38, 128.5, 192.75, and 257 mg, respectively. Adjusted dosages of 25 and 50 mg sitagliptin are used for patients with renal failure.

A dosage range of the DPP-4 inhibitor vildagliptin is usually between 10 and 150 mg daily, in particular between 25 and 150 mg, 25 and 100 mg or 25 and 50 mg or 50 and 100 mg daily. Particular examples of daily oral dosage are 25, 30, 35, 45, 50, 55, 60, 80, 100 or 150 mg. In a more particular aspect, the daily administration of vildagliptin is between 25 and 150 mg or between 50 and 100 mg. In another more particular aspect, the daily administration of vildagliptin is 50 or 100 mg. The application of the active ingredient may occur up to three times a day, preferably one or two times a day. Particular dosage strengths are 50 mg or 100 mg vildagliptin.

Metformin is usually given in doses varying from about 250 mg to 3000 mg, particularly from 500 mg to 2000 mg up to 2500 mg per day using various dosage regimens. A dosage range of the partner drug metformin is usually from 100 mg to 500 mg or 200 mg to 850 mg (1-3 times a day), or from 300 mg to 1000 mg once or twice a day.

The unit dosage strengths of the metformin hydrochloride for use in the present invention may be from 100 mg to 2000 mg or from 250 mg to 2000 mg, preferably from 250 mg to 1000 mg. Particular dosage strengths may be 250, 500, 625, 750, 850 and 1000 mg of metformin hydrochloride. These unit dosage strengths of metformin hydrochloride represent the dosage strengths approved in the US for marketing to treat type 2 diabetes. More particular unit dosage strengths of metformin hydrochloride for incorporation into the fixed dose combination pharmaceutical compositions of the present invention are 500, 850 and 1000 mg of metformin hydrochloride.

A dosage of the partner drug pioglitazone is usually 1-10 mg, 15 mg, 30 mg, or 45 mg once a day.

A dosage of the partner drug telmisartan is usually from 20 mg to 320 mg or 40 mg to 160 mg per day.

A dosage of the partner drug atorvastatin is usually from 1 mg to 40 mg or 10 mg to 80 mg once a day The amount of the DPP-4 inhibitor and of the partner drug in the pharmaceutical composition according to this invention correspond to the respective dosage ranges as provided hereinbefore. For example, a pharmaceutical composition comprises 1-[(4-methyl-quinazolin-2-yl)methyl]-3-methyl-7-(2-butyn-1-yl)-8-(3-(R)-amino-piperidin-1-yl)-xanthine in an amount of 0.5 mg to 10 mg (namely 0.5 mg, 1 mg, 2.5 mg, 5 mg or 10 mg) and of metformin hydrochloride in an amount of 250 mg to 1000 mg (namely 250, 500, 625, 750, 850 or 1000 mg).

Specific embodiments of dosage strengths for 1-[(4-methyl-quinazolin-2-yl)methyl]-3-methyl-7-(2-butyn-1-yl)-8-(3-(R)-amino-piperidin-1-yl)-xanthine and metformin hydrochloride in the fixed dose combinations of the present invention are the following:

(1) 2.5 mg of 1-[(4-methyl-quinazolin-2-yl)methyl]-3-methyl-7-(2-butyn-1-yl)-8-(3-(R)-amino-piperidin-1-yl)-xanthine free base, and 500 mg metformin hydrochloride;

(2) 2.5 mg of 1-[(4-methyl-quinazolin-2-yl)methyl]-3-methyl-7-(2-butyn-1-yl)-8-(3-(R)-amino-piperidin-1-yl)-xanthine free base, and 850 mg metformin hydrochloride;

(3) 2.5 mg of 1-[(4-methyl-quinazolin-2-yl)methyl]-3-methyl-7-(2-butyn-1-yl)-8-(3-(R)-amino-piperidin-1-yl)-xanthine free base, and 1000 mg metformin hydrochloride.

The particular fixed dose combinations of BI 1356 and metformin of the present invention may be administered once or twice daily to the patient, in particular twice daily.

In a preferred aspect of the present invention, the present invention is directed to a pharmaceutical composition (especially an oral solid dosage form, particularly a tablet) comprising or obtainable from a DPP-4 inhibitor selected from the group consisting of 1-[(4-methyl-quinazolin-2-yl)methyl]-3-methyl-7-(2-butyn-1-yl)-8-(3-(R)-amino-piperidin-1-yl)-xanthine free base, vildagliptin, saxagliptin and alogliptin, metformin hydrochloride, L-arginine, and one or more pharmaceutical excipients, such as e.g. those described herein.

A particularly preferred DPP-4 inhibitor to be emphasized within the meaning of this invention is 1-[(4-methyl-quinazolin-2-yl)methyl]-3-methyl-7-(2-butyn-1-yl)-8-(3-(R)-amino-piperidin-1-yl)-xanthine free base (also known as BI 1356).

In particular, it has been found that L-arginine is effective as stabilizing agent for FDC combinations of 1-[(4-methyl-quinazolin-2-yl)methyl]-3-methyl-7-(2-butyn-1-yl)-8-(3-(R)-amino-piperidin-1-yl)-xanthine free base with metformin HCl. Even after 6 months storage at accelerated conditions L-arginine is able to suppress degradation of 1-[(4-methyl-quinazolin-2-yl)methyl]-3-methyl-7-(2-butyn-1-yl)-8-(3-(R)-amino-piperidin-1-yl)-xanthine free base effectively. The effect seems to be concentration dependent. Thus, L-arginine may act as stabilizing and buffering agent in the formulation.

In a more preferred aspect of the present invention, the present invention is directed to a pharmaceutical composition (especially an oral solid dosage form, particularly a tablet) comprising or made from 1-[(4-methyl-quinazolin-2-yl)methyl]-3-methyl-7-(2-butyn-1-yl)-8-(3-(R)-amino-piperidin-1-yl)-xanthine free base (BI 1356), metformin hydrochloride, L-arginine, and one or more pharmaceutical excipients, such as e.g. those described herein.

Typical pharmaceutical compositions according to this invention comprise or are made by comprising combining any one of the following amounts (1), (2) or (3) of active ingredients and L-arginine:

(1) 2.5 mg of 1-[(4-methyl-quinazolin-2-yl)methyl]-3-methyl-7-(2-butyn-1-yl)-8-(3-(R)-amino-piperidin-1-yl)-xanthine free base, 500 mg metformin hydrochloride, and from 1.0 mg to 12.5 mg L-arginine (specifically 1.0 mg, 2.5 mg or 12.5 mg L-arginine);

(2) 2.5 mg of 1-[(4-methyl-quinazolin-2-yl)methyl]-3-methyl-7-(2-butyn-1-yl)-8-(3-(R)-amino-piperidin-1-yl)-xanthine free base, 850 mg metformin hydrochloride, and from 1.0 mg to 21.2 mg L-arginine (specifically 1.0 mg, 2.5 mg or 21.2 mg L-arginine);

(3) 2.5 mg of 1-[(4-methyl-quinazolin-2-yl)methyl]-3-methyl-7-(2-butyn-1-yl)-8-(3-(R)-amino-piperidin-1-yl)-xanthine free base, 1000 mg metformin hydrochloride, and from 1.0 mg to 25.0 mg L-arginine (specifically 1.0 mg, 2.5 mg or 25 mg L-arginine).

In a further aspect of the present invention, the present invention provides methods of manufacturing of the compositions, formulations, blends or dosage forms of this invention, such as e.g. by using methods known to one skilled in the art and/or in a manner as described herein, for example they may be obtained by processes comprising using (e.g. mixing, combining, blending and/or composing) the components and/or ingredients, or pre-mixtures thereof, mentioned hereinbefore and hereinafter, as well as the present invention further provides compositions, formulations, blends or dosage forms obtainable by these methods or processes and/or obtainable from the components, ingredients, pre-mixtures and/or mixtures mentioned hereinbefore and hereinafter.

In a further aspect of the present invention, the present invention provides a pharmaceutical composition, formulation, blend or dosage form of this invention which is substantially free of or only marginally comprises impurities and/or degradation products; that means, for example, that the composition, formulation, blend or dosage from includes about <5%, or about <4%, or about <3%, or less than about 2%, preferably less than about 1%, more preferably less than about 0.5%, even more preferably less than about 0.2% of any individual or total impurity or degradation product(s) by total weight, such as e.g. N-acetyl and/or N-carbamoyl derivative of the free base type DPP-4 inhibitor. The content and/or degradation can be determined by well-known analytical methods, for example using HPLC methods.

In this context, in a further aspect of the present invention, the present invention provides derivatives of a DPP-4 inhibitor having an amino group, particularly a free primary amino group, as mentioned herein, said derivatives being obtainable by acetylation of the amino group (e.g. to yield the group —NHC(O)CH$_3$) or by carbamoylation of the amino group (e.g. to yield the group —NHC(O)NH$_2$).

Dosage Forms for the FDC Formulations of this Invention:

Another purpose of this invention is to develop the FDC formulations of this invention with a reasonable tablet size, with good tablet properties (e.g. stability, hardness, friability, disintegration, content uniformity and the like) and, in a preferred embodiment, without disturbing the original dissolution profiles of each mono tablet in case of desired proof of bioequivalence with minimized risk of failure.

Designing of the dosage form is an important matter not only to optimize the tablet size and dissolution profiles but also to minimize the amount of stabilizing agent, because the pH change by dissolving of buffering agent may affect the dissolution profiles of the DPP-4 inhibitor or a partner drug. The selection of the dosage form is depending on the dose strengths of the active ingredients used and their physicochemical and solid state characteristics.

A conventional approach (i.e. physical separation) may not be useful for stabilization of certain DPP-4 inhibitors of this invention. A buffering agent like L-arginine need to be added into the formulation for suppressing degradation, however it may be necessary to minimize the amount of L-arginine because its alkaline characteristics give a negative impact on the dissolution profiles or the stability of the DPP-4 inhibitor or a partner drug.

Thus, it has been found that suitable dosage forms for the FDC formulations of this invention are film-coated tablets (film-coating for drug loading, such as particularly DPP-4 inhibitor drug loading by film coating on tablet cores containing the partner drug), mono-layer tablets, bi-layer tablets, tri-layer tablets and press-coated tablets (e.g. tablet-in-tablet or bull's eye tablet with DPP-4 inhibitor core), which dosage forms are good measures to achieve the goal under consideration of desired pharmaceutical profiles and characteristics of a DPP-4 inhibitor and a partner drug used.

Said dosage forms have been found to be applicable to the FDC formulations either keeping the original dissolution profiles of each mono tablet or adjusting the profiles to desired levels, e.g. including extended release characteristics, and a reasonable tablet size.

A typical mono-layer tablet of this invention comprises a DPP-4 inhibitor, metformin hydrochloride, L-arginine, one or more fillers (such as e.g. corn starch), one or more binders (such as e.g. copovidone), one or more glidants (such as e.g. colloidal anhydrous silica) and one or more lubricants (such as e.g. magnesium stearate).

In a preferred embodiment of the present invention, the present invention is directed to an oral solid pharmaceutical composition, preferably a tablet, particularly a mono-layer tablet comprising or made from 1-[(4-methyl-quinazolin-2-yl)methyl]-3-methyl-7-(2-butyn-1-yl)-8-(3-(R)-amino-piperidin-1-yl)-xanthine (also known as BI 1356, e.g. in an amount of 2.5 mg), metformin (particularly metformin hydrochloride, e.g. in an amount of 500 mg, 850 mg or 1000 mg), L-arginine, and one or more pharmaceutical excipients, particularly one or more fillers (e.g. corn starch), one or more binders (e.g. copovidone), one or more glidants (e.g. colloidal anhydrous silica) and/or one or more lubricants (e.g. magnesium stearate), as well as, optionally, a film coat e.g. comprising one or more film-coating agents (e.g. hypromellose), one or more plasticizers (e.g. propylene glycol), one or more pigments (e.g. titanium dioxide, iron oxide red and/or iron oxide yellow) and/or one or more glidants (e.g. talc).

A method of manufacturing a tablet of this invention comprises tabletting (e.g. compression) of one or more final blends in form of granules. Granules of the (final) blend(s) according to this invention may be prepared by methods well-known to one skilled in the art (e.g. high shear wet granulation or fluid bed granulation). Granules according to this invention as well as details of granulation processes (including their separate steps) for the preparation of granules of this invention are described by way of example in the following examples.

An illustrative granulation process for the preparation of granules comprising the mono-layer composition comprises i.) combining (e.g. dissolving or dispersing) L-arginine, a binder (e.g. copovidone) and, optionally, the DPP-4 inhibitor (e.g. BI 1356) in a solvent or mixture of solvents such as purified water at ambient temperature to produce a granulation liquid;

ii.) blending metformin HCl, a filler (e.g. corn starch) and, optionally, the DPP-4 inhibitor (e.g. BI 1356) in a suitable mixer (e.g. fluid-bed granulator) to produce a pre-mix; wherein the DPP-4 inhibitor (e.g. BI 1356) may be included either in the granulation liquid obtained in i.) or in the pre-mix obtained in ii.), preferably BI 1356 is dispersed in the granulation liquid and is absent in the pre-mix;

iii.) spraying the granulation-liquid into the pre-mix and granulating the mixture for example in a fluid-bed granulator, preferably under dry condition;

iv.) drying the granulate, e.g. at about 70° C. inlet air temperature until the desired loss on drying value in the range of 1-2% is obtained;

v.) delumping the dried granulate for example by sieving through a sieve with a mesh size of 0.5 to 1.0 mm;

vi.) blending the sieved granulate and preferably sieved glidant (e.g. colloidal anhydrous silica) in a suitable blender;

vii.) adding preferably sieved lubricant (e.g. magnesium stearate) to the granulate for final blending for example in the free-fall blender.

Preferentially, a mono-layer tablet according to this invention comprises or is obtainable from a mixture comprising any one of the following amounts (1), (2) or (3) of active ingredients and L-arginine:

(1) 2.5 mg of 1-[(4-methyl-quinazolin-2-yl)methyl]-3-methyl-7-(2-butyn-1-yl)-8-(3-(R)-amino-piperidin-1-yl)-xanthine free base, 500 mg metformin hydrochloride, and 12.5 mg L-arginine;

(2) 2.5 mg of 1-[(4-methyl-quinazolin-2-yl)methyl]-3-methyl-7-(2-butyn-1-yl)-8-(3-(R)-amino-piperidin-1-yl)-xanthine free base, 850 mg metformin hydrochloride, and 21.2 mg L-arginine;

(3) 2.5 mg of 1-[(4-methyl-quinazolin-2-yl)methyl]-3-methyl-7-(2-butyn-1-yl)-8-(3-(R)-amino-piperidin-1-yl)-xanthine free base, 1000 mg metformin hydrochloride, and 25 mg L-arginine.

A typical bi-layer tablet of this invention comprises a DPP-4 inhibitor portion comprising a DPP-4 inhibitor, L-arginine, one or more fillers (such as e.g. D-mannitol, pregelatinized starch and corn starch), one or more binders (such as e.g. copovidone) and one or more lubricants (such as e.g. magnesium stearate), and a metformin HCl portion comprising metformin hydrochloride, one or more fillers (such as e.g. corn starch), one or more binders (such as e.g. copovidone), one or more glidants (such as e.g. colloidal anhydrous silica) and one or more lubricants (such as e.g. magnesium stearate).

Preferentially, a bi-layer tablet according to this invention comprises or is obtainable from a mixture comprising any one of the following amounts (1), (2) or (3) of active ingredients and L-arginine:

(1) 2.5 mg of 1-[(4-methyl-quinazolin-2-yl)methyl]-3-methyl-7-(2-butyn-1-yl)-8-(3-(R)-amino-piperidin-1-yl)-xanthine free base, 500 mg metformin hydrochloride, and 2.5 mg L-arginine;

(2) 2.5 mg of 1-[(4-methyl-quinazolin-2-yl)methyl]-3-methyl-7-(2-butyn-1-yl)-8-(3-(R)-amino-piperidin-1-yl)-xanthine free base, 850 mg metformin hydrochloride, and 2.5 mg L-arginine;

(3) 2.5 mg of 1-[(4-methyl-quinazolin-2-yl)methyl]-3-methyl-7-(2-butyn-1-yl)-8-(3-(R)-amino-piperidin-1-yl)-xanthine free base, 1000 mg metformin hydrochloride, and 2.5 mg L-arginine.

A typical press-coated tablet (tablet-in-tablet or bull's eye tablet) of this invention comprises a DPP-4 inhibitor core portion comprising a DPP-4 inhibitor, L-arginine, one or more fillers (such as e.g. D-mannitol, pregelatinized starch and corn starch), one or more binders (such as e.g. copovidone) and one or more lubricants (such as e.g. magnesium stearate), and a metformin HCl portion comprising metformin hydrochloride, one or more fillers (such as e.g. corn starch), one or more binders (such as e.g. copovidone), one or more glidants (such as e.g. colloidal anhydrous silica) and one or more lubricants (such as e.g. magnesium stearate).

Preferentially, a press-coated tablet (tablet-in-tablet or bull's eye tablet) according to this invention comprises or is obtainable from a mixture comprising any one of the following amounts (1), (2) or (3) of active ingredients and L-arginine:

(1) 2.5 mg of 1-[(4-methyl-quinazolin-2-yl)methyl]-3-methyl-7-(2-butyn-1-yl)-8-(3-(R)-amino-piperidin-1-yl)-xanthine free base, 500 mg metformin hydrochloride, and 1.0 mg L-arginine;

(2) 2.5 mg of 1-[(4-methyl-quinazolin-2-yl)methyl]-3-methyl-7-(2-butyn-1-yl)-8-(3-(R)-amino-piperidin-1-yl)-xanthine free base, 850 mg metformin hydrochloride, and 1.0 mg L-arginine;

(3) 2.5 mg of 1-[(4-methyl-quinazolin-2-yl)methyl]-3-methyl-7-(2-butyn-1-yl)-8-(3-(R)-amino-piperidin-1-yl)-xanthine free base, 1000 mg metformin hydrochloride, and 1.0 mg L-arginine.

A typical film-coated tablet (DPP-4 inhibitor coating on metformin HCl tablet, i.e. drug layering by film-coating for drug loading) of this invention comprises a metformin HCl core portion comprising metformin hydrochloride, one or more fillers (such as e.g. corn starch), one or more binders (such as e.g. copovidone), one or more glidants (such as e.g. colloidal anhydrous silica) and one or more lubricants (such as e.g. magnesium stearate), wherein said core portion is seal-coated with a film coat comprising one or more film-coating agents (such as e.g. hypromellose), one or more plasticizers (such as e.g. propylene glycol), one or more pigments (such as e.g. titanium dioxide, iron oxide red and/or iron oxide yellow) and one or more glidants (such as e.g. talc);

and a DPP-4 inhibitor layer comprising a DPP-4 inhibitor, L-arginine, one or more film-coating agents (such as e.g. hypromellose) and one or more plasticizers (such as e.g. propylene glycol).

Preferentially, a film-coated tablet (DPP4-inhibitor drug loading) according to this invention comprises or is obtainable from a mixture comprising any one of the following amounts (1), (2) or (3) of active ingredients and L-arginine:

(1) 2.5 mg of 1-[(4-methyl-quinazolin-2-yl)methyl]-3-methyl-7-(2-butyn-1-yl)-8-(3-(R)-amino-piperidin-1-yl)-xanthine free base, 500 mg metformin hydrochloride, and 2.5 mg L-arginine;

(2) 2.5 mg of 1-[(4-methyl-quinazolin-2-yl)methyl]-3-methyl-7-(2-butyn-1-yl)-8-(3-(R)-amino-piperidin-1-yl)-xanthine free base, 850 mg metformin hydrochloride, and 2.5 mg L-arginine;

(3) 2.5 mg of 1-[(4-methyl-quinazolin-2-yl)methyl]-3-methyl-7-(2-butyn-1-yl)-8-(3-(R)-amino-piperidin-1-yl)-xanthine free base, 1000 mg metformin hydrochloride, and 2.5 mg L-arginine.

Preferably, these abovementioned tablets (mono-, bi-layer, press-coated and drug-coated tablets) are further over-coated with a final film coat, which comprises a film-coating agent (such as e.g. hypromellose), a plasticizer (such as e.g. propylene glycol), pigments (such as e.g. titanium dioxide, iron oxide red and/or iron oxide yellow) and a glidant (such as e.g. talc). Typically this additional film over-coat may represent 1-4%, preferentially 1-2%, of the total mass of the composition.

The following dosage forms of the invention can be applied to the FDC formulation of 1-[(4-methyl-quinazolin-2-yl)methyl]-3-methyl-7-(2-butyn-1-yl)-8-(3-(R)-amino-piperidin-1-yl)-xanthine free base (BI 1356) and metformin hydrochloride based on the characteristics of drug substances and requirements of the desired pharmaceutical profiles:

a) Mono-Layer Tablets

Mono-layer tablets with L-arginine show satisfactory stability results, good dissolution properties and good content uniformity (CU). Mono-layer tablets can be manufactured using conventional technologies (including fluid-bed granulation for the DPP-4 inhibitor and metformin hydrochloride, e.g. comprising adding the DPP-4 inhibitor as powder or as an aqueous suspension in the granulation liquid to the fluid bed granulator).

b) Bi-Layer Tablets

Bi-layer tablets with L-arginine show promising stability results, good dissolution properties and good CU. Bi-layer tablets can be manufactured using conventional bi-layer tableting technologies (e.g. rotary bi-layer tableting machine).

c) Press-Coated Tablets

Press-coated tablets (tablet-in-tablets and advanced press-coated bull's eye tablets) show promising stability, good CU and dissolution. Press-coated tablets can be manufactured using conventional press-coating technology, such as e.g. on a Kilian tablet press to obtain tablet-in-tablet or on other conventional press-coater to obtain bull's eye tablet. As an advantage of this approach, it is easy to minimize the amount of L-arginine in the formulation and control the assay and CU of the DPP-4 inhibitor portion (very small amount of drug loading; 2.5 mg/tablet where the dose strengths of metformin HCl are 500, 850 and 1000 mg/tablet). Another advantage is that DPP-4 inhibitor- and metformin HCl-portion can be designed flexibly to minimize the tablet size. A modified press-coated tablet named "bull's eye tablet" may be a universal dosage potentially for bi-layer tablets as well as other FDC. Bull's eye tablet can be manufactured in a one-step press-coating without separate core formation (like in bi-layer tableting) being necessary.

It is to be noted that within the meaning of this invention the skilled person is aware about what is meant with the phrase "bull's eye tablet" used herein. As it known to the skilled person, this tablet (also referred to as an inlay tablet or a dot) is composed of an outer coat and an inner core, and in which, instead of the inner core zone being completely surrounded by the outer coat, one surface of the zone corresponding to the inner core zone is exposed.

d) Film-Ccoated Tablets (Drug Layering by Film-Coating for Drug Loading)

Coating of DPP-4 inhibitor drug substance on the metformin HCl tablets shows acceptable dissolution results and promising stability data. L-arginine needs to be added into film-coating for stabilization. As an advantage for this approach, it is possible to integrate DPP-4 inhibitor portion into a partner drug portion as it is, even if the dosage form is a modified/controlled release formulation. Within the film-coating process coating endpoint determination is necessary via analytics.

The method of layering of the DPP-4 inhibitor by film-coating as described herein (including the steps of seal-coating, drug-loading and, optional, over-coating) may be applied to any kind of cores or tablets which may comprise an active ingredient (e.g. a partner drug as mentioned herein), for example metformin cores or tablets, such as e.g. immediate release metformin tablets, sustained release metformin tablets, extended release metformin tablets, modified release metformin tablets, controlled release metformin tablets or delayed release metformin tablets. Thus, the present invention further relates to a tablet which comprises a film-coat layer comprising the DPP-4 inhibitor, a film-forming agent (e.g. hypromellose), a plasticizer (e.g. propylene glycol) and L-arginine, or which is obtainable by comprising using such a method of layering of the DPP-4 inhibitor by film-coating as described herein. The present invention also relates to a FDC tablet comprising an immediate or extended release metformin tablet core, a seal coat, a film-coat layer comprising the DPP-4 inhibitor, and, optionally, an over-coat; e.g. each as described herein, as well as to such a FDC tablet made by a process comprising the following steps of seal-coating on a metformin tablet core, layering of a DPP-4 inhibitor by film-coating and, optional, over-coating, e.g. each step such as described herein.

Pharmaceutical immediate release dosage forms of this invention preferably have dissolution properties such that after 45 minutes for each of the active ingredients at least 75%, even more preferably at least 90% by weight of the respective active ingredient is dissolved. In a particular embodiment, after 30 minutes for each of the active ingredients especially of the mono-layer tablet according to this invention (including tablet core and film-coated tablet) at least 70-75% (preferably at least 80%) by weight of the respective active ingredient is dissolved. In a further embodiment, after 15 minutes for each of the active ingredients especially of the mono-layer tablet according to this invention (including tablet core and film-coated tablet) at least 55-60% by weight of the respective active ingredient is dissolved. The dissolution properties can be determined in standard dissolution tests, e.g. according to standard pharmacopeias (e.g. using paddle method with agitation speed of 50 rpm, 0.1 M hydrochloric acid as dissolution medium at a temperature of 37° C., and HPLC (BI 1356) and UV (metformin) analysis of the samples).

In the pharmaceutical compositions and pharmaceutical dosage forms according to the invention BI 1356, for example a crystalline form thereof, preferably has a particle size distribution (preferably by volume) such that at least 90% of the respective active pharmaceutical ingredient has a particle size smaller than 200 µm, i.e. X90<200 µm, more preferably X90≤150 µm. More preferably the particle size distribution is such that X90≤100 µm, even more preferably X90≤75 µm. In addition the particle size distribution is preferably such that X90>0.1 µm, more preferably X90≥1 µm, most preferably X90≤5 µm. Therefore preferred particle size distributions are such that 0.1 µm<X90<200 µm, particularly 0.1 µm<X90≤150 µm, more preferably 1 µm≤X90≤150 µm, even more preferably 5 µm≤X90≤100 µm. A preferred example of a particle size distribution of BI 1356 is such that X90≤50 µm or 10 µm≤X90≤50 µm. It can be found that a pharmaceutical composition comprising BI 1356 with a particle size distribution as indicated hereinbefore shows desired properties (e.g. with regard to dissolution, content uniformity, production, or the like). The indicated particle size properties are determined by laser-diffraction method, in particular low angle laser light scattering, i.e. Fraunhofer diffraction. Alternatively, the particle size properties can be also determined by microscopy (e.g. electron microscopy or scanning electron microscopy). The results of the particle size distribution determined by different techniques can be correlated with one another.

Optimized Formulation of Metformin HCl Portion:

Another purpose of this invention is to provide improved formulations of the metformin HCl portion of the pharmaceutical compositions according to this invention.

For the metformin HCl part a high drug load is advantageous to be achieved as a pre-requisite for a reasonable small tablet size.

Thus, it has been found that drug load of metformin HCl and compactability (compression force-crushing strength profile) of the tablets of this invention can be improved by surface treatment of metformin HCl with a water-soluble polymer, particularly copolyvidone.

Several water-soluble polymers including polyvinyl alcohol (PVA), hypromellose (HPMC), hydroxypropyl cellulose (HPC), methyl cellulose (MC), Povidone (PVP) and copolyvidone may be tested to improve compactability (compression force-crushing strength profile). As the results, PVA shows the best effect in terms of compactability but the manufacturability can be poor due to sticking problem during fluid-bed granulation. Further on, PVA may be not finally selected because of its negative impact on the stability of certain DPP-4 inhibitors of this invention.

Therefore, finally, copolyvidone is selected and the amount can be optimized, advantageously resulting in stable formulations and the viscosity of the granulating solution is enough low to prepare the aqueous solution and operate spraying by a fluid-bed granulator.

In optional addition, it has been found that heating/drying of metformin HCl drug substance is effective to improve the stability of certain DPP-4 inhibitors of this invention in combination with metformin HCl. The pre-treatment for metformin HCl needs to be conducted before starting of granulation with the DPP-4 inhibitor. The heating/drying at 80° C. with a fluid-bed granulator may be helpful to reduce an excessive amount of volatile impurities (which might be urea) in the metformin HCl.

The present invention is not to be limited in scope by the specific embodiments described herein. Various modifications of the invention in addition to those described herein may become apparent to those skilled in the art from the present disclosure. Such modifications are intended to fall within the scope of the appended claims.

All patent applications cited herein are hereby incorporated by reference in their entireties.

Further embodiments, features and advantages of the present invention may become apparent from the following examples. The following examples serve to illustrate, by way of example, the principles of the invention without restricting it.

EXAMPLES

1. Mono-Layer Tablet

The composition of mono-layer tablets for a DPP-4 inhibitor of this invention (BI 1356)+metformin HCl FDC (Film-coated Tablets) is shown in Table 1.

TABLE 1

Composition of BI 1356 + Metformin HCl FDC Mono-layer Tablets

| | Dose Strength (BI 1356/metformin HCl), mg | | | | | |
|---|---|---|---|---|---|---|
| | 2.5/500 | | 2.5/850 | | 2.5/1000 | |
| Ingredient | [mg] | [%] | [mg] | [%] | [mg] | [%] |
| BI 1356 | 2.50 | 0.42 | 2.50 | 0.25 | 2.50 | 0.21 |
| Metformin Hydrochloride | 500.0 | 84.75 | 850.00 | 85.00 | 1000.00 | 84.75 |
| L-Arginine | 12.50 | 2.12 | 21.20 | 2.12 | 25.00 | 2.12 |
| Corn starch | 20.00 | 3.39 | 33.10 | 3.31 | 42.50 | 3.60 |
| Copovidone | 47.50 | 8.05 | 80.50 | 8.05 | 95.00 | 8.05 |
| Colloidal Anhydrous Silica | 2.50 | 0.42 | 4.20 | 0.42 | 5.00 | 0.42 |
| Magnesium stearate | 5.00 | 0.85 | 8.50 | 0.85 | 10.00 | 0.85 |
| Purified water* | 186** | | 315** | | 372** | |
| Total Mass (tablet core) | 590.00 | 100.00 | 1000.00 | 100.00 | 1180.00 | 100.00 |
| Hypromellose (5 mPa*s) | 6.00 | 50.00 | 8.00 | 50.00 | 9.00 | 50.00 |
| Propylene glycol | 0.60 | 5.00 | 0.80 | 5.00 | 0.90 | 5.00 |
| Talc | 2.88 | 18.50 | 2.96 | 18.50 | 4.455 | 18.50 |
| Titanium dioxide | 2.40 | 25.00 | 4.00 | 25.00 | 3.60 | 25.00 |
| Iron oxide, yellow | 0.12 | 1.25 | 0.20 | 1.25 | | |
| Iron oxide, red | | | 0.04 | 0.25 | 0.045 | 1.25 |
| Purified water** | 88** | | 117** | | 132** | |
| Total Mass (film-coat) | 12.00 | 100.00 | 16.00 | 100.00 | 18.00 | 100.00 |
| Total Mass (coated tablet) | 602.00 | | 1016.00 | | 1198.00 | |

**Removed during processing, does not appear in final product

Formulation optimization studies have identified a composition with over 84% drug load of metformin HCl and improved crushing strength by surface-treatment of metformin HCl with the water-soluble polymer copolyvidone.

Manufacturing Procedure (Mono-Layer Tablets):

DPP-4 inhibitor of this invention (e.g. BI 1356)+metformin HCl FDC mono-layer tablets are produced by a fluid-bed granulation process and a conventional tableting process with a rotary press. Optionally, metformin HCl and corn starch may be pre-treated by heating in a chamber of fluid-bed granulator to remove excessive HCl and/or impurity products before mixing with the active DPP-4 inhibitor ingredient. After the optional pre-treatment of metformin HCl and corn starch, the DPP-4 inhibitor is either added as powder and premixed before fluid-bed granulation is conducted by spraying of "Granulation Liquid" composed of copolyvidon (Kollidon VA64), L-arginine and purified water, or directly dispersed in the "granulation liquid". After finishing of fluid-bed granulation, the granulate is sieved with a suitable screen. The sieved granulate is blended with colloidal anhydrous silica (Aerosil 200) and magnesium stearate as a lubricant. The final mixture is compressed into tablets using a conventional rotary tablet press.

The tablet cores may be film-coated by an aqueous film-coating suspension, containing hypromellose as film-forming agent, propylene glycol as plasticizer, talc as glidant and the pigments yellow iron oxide and/or red iron oxide and titanium dioxide.

Narrative more specific description of the preferred manufacturing process for the mono-layer tablets:

a) Metformin HCl and corn starch are sieved using a screen with a mesh size of 0.5 to1 mm before dispensing.

b) L-arginine, BI 1356 and finally copolyvidon are dissolved resp. dispersed in purified water at ambient temperature with a propeller mixer to produce the "Granulation Liquid".

c) Metformin HCl and corn starch are sucked into a chamber of a suitable fluid-bed granulator and preheated up to a product temperature target of approx. 36° C.

d) Immediately after the product temperature target is reached, the "Granulation Liquid" is sprayed into the mixture for fluid-bed granulating under dry condition to avoid blocking during granulation.

e) At the end of spraying, the resultant granulate is dried at approx. 70 C inlet air temperature until the desired LOD value (i.e. 1-2%) is reached.

f) The granulate is sieved using a screen with a mesh size of 0.5 to 1.0 mm.

g) The sieved granulate and colloidal anhydrous silica (Aerosil 200) are blended with a suitable blender. Aerosil 200 should be pre-sieved with a small portion of the sieved granulate through a 0.8 mm-screen before use.

h) Magnesium stearate is passed through a 0.8 mm sieve and added into the granulate. Subsequently the "Final Blend" is produced by final blending in the free-fall blender.

i) The "Final Blend" is compressed into tablets with a rotary press.

j) Titanium dioxide, propylene glycol and iron oxide (yellow, red or yellow and red) are dispersed in purified water with a high shear homo-mixer. Then, hypromellose and talc are added and dispersed with a homo-mixer and propeller mixer at ambient temperature to produce the "Coating Suspension".

k) The tablet cores are coated with the "Coating Suspension" to the target weight gain to produce the "Film-coated Tablets". The "Coating Suspension" should be stirred again before use and kept stirring slowly during the coating (spraying) process.

Narrative more specific description of an alternative manufacturing process for the mono-layer tablets:

a) Metformin HCl is sieved using a screen with a mesh size of 0.5 to1 mm before weighing.

b) L-arginine and copolyvidon are dissolved in purified water at ambient temperature with a propeller mixer to produce the "Granulation Liquid"

c) Metformin HCl and corn starch are heated in a chamber of fluid-bed granulator at 70-80° C. for more than 15 min until the product temperature reaches 60° C. d) BI 1356 is added into the container, then blended with metformin HCl and corn starch in the fluid-bed granulator.

e) The "Granulation Liquid" is sprayed into the mixture for fluid-bed granulating under dry condition to avoid blocking during granulation.

f) At the end of spraying, the resultant granulate is dried at 70-80° C. until the desired LOD value (i.e. 1-2%), in case the LOD is more than 2%.

g) The granulate is sieved using a screen with a mesh size of 0.5 to 1.0 mm.

h) The sieved granulate and colloidal anhydrous silica (Aerosil 200) are blended with a suitable blender. Aerosil 200 should be sieved with a 0.5 mm-screen before use.

i) Magnesium stearate passed through a 0.5 mm sieve and added into the granulate. Subsequently the "Final Blend" is produced by final blending in the blender.

j) The "Final Blend" is compressed into tablets with a rotary press.

k) Hypromellose and propylene glycol are dissolved in purified water with a propeller mixer. Talc, titanium dioxide, and iron oxide (yellow, or yellow and red) are dispersed in purified water with a homo-mixer. The suspension is added into the hypromellose solution, then mixed with a propeller mixer at ambient temperature to produce the "Coating Suspension".

l) The tablet cores are coated with the "Coating Suspension" to the target weight gain to produce the "Film-coated Tablets". The "Coating Suspension" should be stirred again before use and kept stirring slowly during the coating (spraying) process.

2. Bi-Layer Tablet

The composition of bi-layer tablets for a DPP-4 inhibitor of this invention (BI 1356)+metformin HCl FDC (Film-coated Tablets) is shown in Table 2.

TABLE 2

Composition of BI 1356 + Metformin HCl FDC Bi-layer Tablets

| | Dose Strength (BI 1356/metformin HCl), mg | | | | | |
|---|---|---|---|---|---|---|
| | 2.5/500 | | 2.5/850 | | 2.5/1000 | |
| Ingredient | [mg] | [%] | [mg] | [%] | [mg] | [%] |
| BI 1356-portion: | (450) | (100) | (450) | (100) | (450) | (100) |
| BI 1356 | 2.50 | 0.556 | 2.50 | 0.556 | 2.50 | 0.556 |
| L-Arginine | 2.50 | 0.556 | 2.50 | 0.556 | 2.50 | 0.556 |
| D-mannitol | 334.75 | 74.39 | 334.75 | 74.39 | 334.75 | 74.39 |

TABLE 2-continued

Composition of BI 1356 + Metformin HCl FDC Bi-layer Tablets

| | Dose Strength (BI 1356/metformin HCl), mg | | | | | |
|---|---|---|---|---|---|---|
| | 2.5/500 | | 2.5/850 | | 2.5/1000 | |
| Ingredient | [mg] | [%] | [mg] | [%] | [mg] | [%] |
| Pregelatinized starch | 45.00 | 10.00 | 45.00 | 10.00 | 45.00 | 10.00 |
| Corn starch | 45.00 | 10.00 | 45.00 | 10.00 | 45.00 | 10.00 |
| Copovidone | 13.50 | 3.00 | 13.50 | 3.00 | 13.50 | 3.00 |
| Magnesium stearate | 6.75 | 1.50 | 6.75 | 1.50 | 6.75 | 1.50 |
| Metformin HCl-portion: | (570) | (100) | (969) | (100) | (1140) | (100) |
| Metformin Hydrochloride | 500.0 | 87.72 | 850.00 | 87.72 | 1000.00 | 87.72 |
| Corn starch | 15.00 | 2.63 | 25.50 | 2.63 | 30.00 | 2.63 |
| Copovidone | 47.50 | 8.33 | 80.57 | 8.33 | 95.00 | 8.33 |
| Colloidal Anhydrous Silica | 2.50 | 0.44 | 4.25 | 0.44 | 5.00 | 0.44 |
| Magnesium stearate | 5.00 | 0.88 | 8.50 | 0.88 | 10.00 | 0.88 |
| Total Mass (tablet core) | 1020 | 100.00 | 1419 | 100.00 | 1590 | 100.00 |
| Hypromellose (5 mPa*s) | 8.00 | 50.00 | 9.50 | 50.00 | 11.00 | 50.00 |
| Propylene glycol | 0.80 | 5.00 | 0.95 | 5.00 | 1.10 | 5.00 |
| Talc | 2.96 | 18.50 | 3.515 | 18.50 | 4.07 | 18.50 |
| Titanium dioxide | 4.00 | 25.00 | 4.75 | 25.00 | 5.50 | 25.00 |
| Iron oxide, yellow | 0.20 | 1.25 | 0.2375 | 1.25 | 0.275 | 1.25 |
| Iron oxide, red | 0.04 | 0.25 | 0.0475 | 0.25 | 0.055 | 0.25 |
| Total Mass (film-coat) | 16.00 | 100.00 | 19.00 | 100.00 | 22.00 | 100.00 |
| Total Mass (coated tablet) | 1036 | 100.00 | 1438 | 100.00 | 1612 | 100.00 |

Manufacturing procedure (Bi-Layer Tablets):

DPP-4 inhibitor of this invention (e.g. BI 1356)+metformin HCl FDC bi-layer tablets are produced by a high-shear wet granulation process (for DPP-4 inhibitor-granulate), a fluid-bed granulation process (for metformin HCl-granulate), and bi-layer tableting process with a multi-layer rotary press.

DPP-4 Inhibitor-Granulate:

By using a high-shear granulator the active DPP-4 inhibitor ingredient is pre-mixed with the diluents D-mannitol and pregelatinized starch. The mixture is moistened with granulating liquid, containing purified water and copovidone as a binder. After further mixing, drying and sieving, the dried granulate is blended with magnesium stearate as a lubricant.

Narrative more specific description of the manufacturing process for the BI 1356-granulate:
a. Copovidone and L-arginine are dissolved in purified water at ambient temperature to produce the Granulation Liquid.
b. BI 1356, mannitol and pregelatinized starch are blended in a suitable mixer, to produce the Pre-Mix.
c. The Pre-mix is moistened with the Granulation Liquid and subsequently granulated.
d. The moist granulate is sieved through a suitable sieve.
e. The granulate is dried at about 50° C. (maximum 60° C.) in a suitable dryer until the desired loss on drying value is obtained.
f. The dried granulate is sieved through a sieve with a mesh size of 1.0 mm.
g. Magnesium stearate is passed through a 1.0 mm sieve and added to the granulate. Subsequently the "Final Blend A" is produced by final blending in a suitable blender.

Metformin HCl-Granulate:

Metformin HCl and corn starch are pre-treated by heating in a chamber of fluid-bed granulator to remove excessive HCl and/or impurity products. After the pre-treatment of metformin HCl and corn starch, fluid-bed granulation is conducted by spraying of "Granulation Liquid" composed of copolyvidon (Kollidon VA64) and purified water. After finishing of fluid-bed granulation, the granulate is sieved with a suitable screen. The sieved granulate is blended with colloidal anhydrous silica (Aerosil 200) and magnesium stearate as a lubricant.

Narrative more specific description of the manufacturing process for the Metformin HCl-granulate:
a) Metformin HCl is sieved using a screen with a mesh size of 0.5 to1 mm before weighing.
b) Copolyvidon is dissolved in purified water at ambient temperature with a propeller mixer to produce the "Granulation Liquid"
c) Metformin HCl and corn starch are heated in a chamber of fluid-bed granulator at 70-80° C. for more than 15 min until the product temperature reaches 60° C.
d) The "Granulation Liquid" is sprayed into the mixture for fluid-bed granulating under dry condition to avoid blocking during granulation.
e) At the end of spraying, the resultant granulate is dried at 70-80° C. until the desired LOD value (i.e. 1-2%), in case the LOD is more than 2%.
f) The granulate is sieved using a screen with a mesh size of 0.5 to 1.0 mm.
g) The sieved granulate and colloidal anhydrous silica (Aerosil 200) are blended with a suitable blender. Aerosil 200 should be sieved with a 0.5 mm-screen before use.
h) Magnesium stearate passed through a 0.5 mm sieve and added into the granulate. Subsequently the "Final Blend B" is produced by final blending in the blender.

The "Final Blend A" and "Final Blend B" are compressed into bi-layer tablets using a multi-layer rotary press. The tablet cores may be film-coated by an aqueous film-coating suspension, containing hypromellose as film-forming agent, propylene glycol as plasticizer, talc as glidant and the pigments yellow iron oxide and/or red iron oxide and titanium dioxide.

Narrative more specific description of the manufacturing process for the film-coating:

a) Hypromellose and propylene glycol are dissolved in purified water with a propeller mixer. Talc, titanium dioxide, and iron oxide (yellow, red or yellow and red) are dispersed in purified water with a homo-mixer. The suspension is added into the hypromellose solution, then mixed with a propeller mixer at ambient temperature to produce the "Coating Suspension".
b) The tablet cores are coated with the "Coating Suspension" to the target weight gain to produce the "Film-coated Tablets". The "Coating Suspension" should be stirred again before use and kept stirring slowly during the coating (spraying) process.

3. Tablet-In-Tablet or Bull's Eye Tablet

The composition of Tablet-in-Tablet or Bull's eye tablets for a DPP-4 inhibitor of this invention (BI 1356)+metformin HCl FDC (Film-coated Tablets) is shown in Table 3.

TABLE 3

Composition of BI 1356 + Metformin HCl FDC Tablet-in-Tablet or Bull's Eye Tablets

| | Dose Strength (BI 1356/metformin HCl), mg | | | | | |
|---|---|---|---|---|---|---|
| | 2.5/500 | | 2.5/850 | | 2.5/1000 | |
| Ingredient | [mg] | [%] | [mg] | [%] | [mg] | [%] |
| BI 1356-portion: | (45) | (100) | (45) | (100) | (45) | (100) |
| BI 1356 | 2.50 | 5.56 | 2.50 | 5.56 | 2.50 | 5.56 |
| L-Arginine | 1.00 | 2.22 | 1.00 | 2.22 | 1.00 | 2.22 |
| D-mannitol | 30.475 | 67.72 | 30.475 | 67.72 | 30.475 | 67.72 |
| Pregelatinized starch | 4.50 | 10.00 | 4.50 | 10.00 | 4.50 | 10.00 |
| Corn starch | 4.50 | 10.00 | 4.50 | 10.00 | 4.50 | 10.00 |
| Copovidone | 1.350 | 3.00 | 1.350 | 3.00 | 1.35 | 3.00 |
| Magnesium stearate | 0.675 | 1.50 | 0.675 | 1.50 | 6.75 | 1.50 |
| Metformin HCl-portion: | (570) | (100) | (969) | (100) | (1140) | (100) |
| Metformin Hydrochloride | 500.0 | 87.72 | 850.00 | 87.72 | 1000.00 | 87.72 |
| Corn starch | 15.00 | 2.63 | 25.50 | 2.63 | 30.00 | 2.63 |
| Copovidone | 47.50 | 8.33 | 80.57 | 8.33 | 95.00 | 8.33 |
| Colloidal Anhydrous Silica | 2.50 | 0.44 | 4.25 | 0.44 | 5.00 | 0.44 |
| Magnesium stearate | 5.00 | 0.88 | 8.50 | 0.88 | 10.00 | 0.88 |
| Total Mass (tablet core) | 615 | 100.00 | 1014 | 100.00 | 1185 | 100.00 |
| Hypromellose (5 mPa*s) | 6.00 | 50.00 | 8.00 | 50.00 | 9.00 | 50.00 |
| Propylene glycol | 0.60 | 5.00 | 0.80 | 5.00 | 0.90 | 5.00 |
| Talc | 2.22 | 18.50 | 2.96 | 18.50 | 3.33 | 18.50 |
| Titanium dioxide | 3.00 | 25.00 | 4.00 | 25.00 | 4.50 | 25.00 |
| Iron oxide, yellow | 0.15 | 1.25 | 0.20 | 1.25 | 0.225 | 1.25 |
| Iron oxide, red | 0.03 | 0.25 | 0.04 | 0.25 | 0.045 | 0.25 |
| Total Mass (film-coat) | 12.00 | 100.00 | 16.00 | 100.00 | 18.00 | 100.00 |
| Total Mass (coated tablet) | 627 | 100.00 | 1030 | 100.00 | 1203 | 100.00 |

Manufacturing procedure (Tablet-in-Tablet or Bull's eye tablet):

DPP-4 inhibitor of this invention (e.g. BI 1356)+metformin HCl FDC Tablet-in-Tablet or Bull's eye tablets are produced by a high-shear wet granulation process (for DPP-4 inhibitor-granulate), a rotary press (for DPP-4 inhibitor core-tablet), a fluid-bed granulation process (for metformin HCl-granulate), and press-coating process with a press-coater.

DPP-4 Inhibitor Core-Tablet:

By using a high-shear granulator the active DPP-4 inhibitor ingredient is pre-mixed with the diluents D-mannitol and pregelatinized starch. The mixture is moistened with granulating liquid, containing purified water and copovidone as a binder. After further mixing, drying and sieving, the dried granulate is blended with magnesium stearate as a lubricant.

Narrative more specific description of the manufacturing process for the BI 1356 core-tablets:

a. Copovidone and L-arginine are dissolved in purified water at ambient temperature to produce the Granulation Liquid.
b. BI 1356, mannitol and pregelatinized starch are blended in a suitable mixer, to produce the Pre-Mix.
c. The Pre-mix is moistened with the Granulation Liquid and subsequently granulated.
d. The moist granulate is sieved through a suitable sieve.
e. The granulate is dried at about 50° C. (maximum 60° C.) in a suitable dryer until the desired loss on drying value is obtained.
f. The dried granulate is sieved through a sieve with a mesh size of 1.0 mm.
g. Magnesium stearate is passed through a 1.0 mm sieve and added to the granulate. Subsequently the "Final Blend" is produced by final blending in a suitable blender.
h. "Final Blend" is compressed into "BI 1356 core-tablets" with a rotary press.

Metformin HCl-Granulate:

Metformin HCl and corn starch are pre-treated by heating in a chamber of fluid-bed granulator to remove excessive HCl and/or impurity products. After the pre-treatment of metformin HCl and corn starch, fluid-bed granulation is conducted by spraying of "Granulation Liquid" composed of copolyvidon (Kollidon VA64) and purified water. After finishing of fluid-bed granulation, the granulate is sieved with a suitable screen. The sieved granulate is blended with colloidal anhydrous silica (Aerosil 200) and magnesium stearate as a lubricant.

Narrative more specific description of the manufacturing process for the Metformin HCl-granulate:

a) Metformin HCl is sieved using a screen with a mesh size of 0.5 to1 mm before weighing.
b) Copolyvidon is dissolved in purified water at ambient temperature with a propeller mixer to produce the "Granulation Liquid"

c) Metformin HCl and corn starch are heated in a chamber of fluid-bed granulator at 70-80° C. for more than 15 min until the product temperature reaches 60° C.
d) The "Granulation Liquid" is sprayed into the mixture for fluid-bed granulating under dry condition to avoid blocking during granulation.
e) At the end of spraying, the resultant granulate is dried at 70-80° C. until the desired LOD value (i.e. 1-2%), in case the LOD is more than 2%.
f) The granulate is sieved using a screen with a mesh size of 0.5 to 1.0 mm.
g) The sieved granulate and colloidal anhydrous silica (Aerosil 200) are blended with a suitable blender. Aerosil 200 should be sieved with a 0.5 mm-screen before use.
h) Magnesium stearate passed through a 0.5 mm sieve and added into the granulate. Subsequently "Metformin HCl-granulate" (Final Blend) is produced by final blending in the blender.

The "DPP-4 inhibitor core-tablets" and "Metformin HCl-granulate" are compressed into Tablet-in-Tablet or Bull's eye tablets using a press-coater. The difference between the Tablet-in-Tablet and Bull's eye tablet is the position of the core tablet.

Narrative more specific description of the manufacturing process for the Tablet-in-Tablet:
a) Fill a half of Metformin HCl-granulate in a die.
b) Place a BI 1356 core-tablet on the surface of Metformin HCl-granulate.
c) Cover the core-tablet with second half of Metformin HCl-granulate, then compressed into the tablet (Tablet-in-Tablet).

Narrative more specific description of the manufacturing process for the Bull's eye tablets:
a) Fill Metformin HCl-granulate in a die.
b) Place the BI 1356 core-tablet on the Metformin HCl-granulate in the die, then compressed into the tablet (Bull's eye tablet).

The tablets may be film-coated by an aqueous film-coating suspension, containing hypromellose as film-forming agent, propylene glycol as plasticizer, talc as glidant and the pigments yellow iron oxide and/or red iron oxide and titanium dioxide.

Narrative more specific description of the manufacturing process for the film-coating:
a) Hypromellose and propylene glycol are dissolved in purified water with a propeller mixer. Talc, titanium dioxide, and iron oxide (yellow, red or yellow and red) are dispersed in purified water with a homo-mixer. The suspension is added into the hypromellose solution, then mixed with a propeller mixer at ambient temperature to produce the "Coating Suspension".
b) The tablet cores are coated with the "Coating Suspension" to the target weight gain to produce the "Film-coated Tablets". The "Coating Suspension" should be stirred again before use and kept stirring slowly during the coating (spraying) process.

4. DPP-4 Inhibitor—Drug Layering on Metformin HCl Tablet (Film-Coating for Drug-Loading)

The composition of a DPP-4 inhibitor of this invention (BI 1356)+metformin HCl FDC (Film-coated Tablets) which are prepared by drug loading by film-coating on the Metformin HCl Tablet is shown in Table 4.

TABLE 4

Composition of BI 1356 + Metformin HCl FDC BI 1356-Coating on Metformin HCl Tablet

| | Dose Strength (BI 1356/metformin HCl), mg | | | | | |
|---|---|---|---|---|---|---|
| | 2.5/500 | | 2.5/850 | | 2.5/1000 | |
| Ingredient | [mg] | [%] | [mg] | [%] | [mg] | [%] |
| Metformin HCl-portion: | (570) | (100) | (969) | (100) | (1140) | (100) |
| Metformin Hydrochloride | 500.0 | 87.72 | 850.0 | 87.72 | 1000.0 | 87.72 |
| Corn starch | 15.0 | 2.63 | 25.5 | 2.63 | 30.0 | 2.63 |
| Copovidone | 47.5 | 8.33 | 80.57 | 8.33 | 95.0 | 8.33 |
| Colloidal Anhydrous Silica | 2.5 | 0.44 | 4.25 | 0.44 | 5.0 | 0.44 |
| Magnesium stearate | 5.0 | 0.88 | 8.5 | 0.88 | 10.0 | 0.88 |
| Total Mass (tablet core) | 570 | 100.00 | 969 | 100.00 | 1140 | 100.00 |
| Seal-coat (seal-coating): | (12) | (100) | (16) | (100) | (18) | (100) |
| Hypromellose (5 mPa*s) | 6.00 | 50.00 | 8.00 | 50.00 | 9.00 | 50.00 |
| Propylene glycol | 0.60 | 5.00 | 0.80 | 5.00 | 0.90 | 5.00 |
| Talc | 2.22 | 18.50 | 2.96 | 18.50 | 3.33 | 18.50 |
| Titanium dioxide | 3.00 | 25.00 | 4.00 | 25.00 | 4.50 | 25.00 |
| Iron oxide, yellow | 0.15 | 1.25 | 0.20 | 1.25 | 0.225 | 1.25 |
| Iron oxide, red | 0.03 | 0.25 | 0.04 | 0.25 | 0.045 | 0.25 |
| Drug-layer (drug-loading): | (25) | (100) | (25) | (100) | (25) | (100) |
| BI 1356 | 2.50 | 10.00 | 2.50 | 10.00 | 2.50 | 10.00 |
| L-Arginine | 2.50 | 10.00 | 2.50 | 10.00 | 2.50 | 10.00 |
| Hypromellose (5 mPa*s) | 18.00 | 72.00 | 18.00 | 72.00 | 18.00 | 72.00 |
| Propylene glycol | 2.00 | 8.00 | 2.00 | 8.00 | 2.00 | 8.00 |
| Over-coat (over-coating): | (12) | (100) | (16) | (100) | (18) | (100) |
| Hypromellose (5 mPa*s) | 6.00 | 50.00 | 8.00 | 50.00 | 9.00 | 50.00 |
| Propylene glycol | 0.60 | 5.00 | 0.80 | 5.00 | 0.90 | 5.00 |
| Talc | 2.22 | 18.50 | 2.96 | 18.50 | 3.33 | 18.50 |
| Titanium dioxide | 3.00 | 25.00 | 4.00 | 25.00 | 4.50 | 25.00 |

TABLE 4-continued

Composition of BI 1356 + Metformin HCl FDC BI 1356-Coating on Metformin HCl Tablet

| | Dose Strength (BI 1356/metformin HCl), mg | | | | | |
|---|---|---|---|---|---|---|
| | 2.5/500 | | 2.5/850 | | 2.5/1000 | |
| Ingredient | [mg] | [%] | [mg] | [%] | [mg] | [%] |
| Iron oxide, yellow | 0.15 | 1.25 | 0.20 | 1.25 | 0.225 | 1.25 |
| Iron oxide, red | 0.03 | 0.25 | 0.04 | 0.25 | 0.045 | 0.25 |
| Total Mass (film-coat) | 49 | 100.00 | 57 | 100.00 | 61 | 100.00 |
| Total Mass (coated tablet) | 619 | 100.00 | 1026 | 100.00 | 1201 | 100.00 |

Manufacturing Procedure (DPP-4 Inhibitor-Drug Layering by Film-Coating on Metformin HCl Tablet):

DPP-4 inhibitor (e.g. BI 1356)+metformin HCl FDC with drug coating is produced by a fluid-bed granulation process, a conventional tableting process, and film-coating process with three steps: seal-coating, drug-loading and over-coating. The over-coating may be able to be skipped by combining with the drug-loading, if the stability is acceptable.

Metformin HCl Tablets:

Metformin HCl and corn starch are pre-treated by heating in a chamber of fluid-bed granulator to remove excessive HCl and/or impurity products. After the pre-treatment of metformin HCl and corn starch, fluid-bed granulation is conducted by spraying of "Granulation Liquid" composed of copolyvidon (Kollidon VA64) and purified water. After finishing of fluid-bed granulation, the granulate is sieved with a suitable screen. The sieved granulate is blended with colloidal anhydrous silica (Aerosil 200) and magnesium stearate as a lubricant. The final blend is compressed into the tablets with a conventional rotary press.

Narrative more specific description of the manufacturing process for the Metformin HCl-granulate:
a) Metformin HCl is sieved using a screen with a mesh size of 0.5 to1 mm before weighing.
b) Copolyvidon is dissolved in purified water at ambient temperature with a propeller mixer to produce the "Granulation Liquid"
c) Metformin HCl and corn starch are heated in a chamber of fluid-bed granulator at 70-80° C. for more than 15 min until the product temperature reaches 60° C.
d) The "Granulation Liquid" is sprayed into the mixture for fluid-bed granulating under dry condition to avoid blocking during granulation.
e) At the end of spraying, the resultant granulate is dried at 70-80° C. until the desired LOD value (i.e. 1-2%), in case the LOD is more than 2%.
f) The granulate is sieved using a screen with a mesh size of 0.5 to 1.0 mm.
g) The sieved granulate and colloidal anhydrous silica (Aerosil 200) are blended with a suitable blender. Aerosil 200 should be sieved with a 0.5 mm-screen before use.
h) Magnesium stearate passed through a 0.5 mm sieve and added into the granulate. Subsequently "Final Blend" is produced by final blending in the blender.
i) The "Final Blend" is compressed into the tablets with a conventional rotary press.

Film-Coating:

The tablets are film-coated by (1) seal-coating: by an aqueous film-coating suspension, containing hypromellose as film-forming agent, propylene glycol as plasticizer, talc as glidant and the pigments yellow iron oxide and/or red iron oxide and titanium dioxide, (2) drug-loading: by an aqueous film-coating suspension, containing hypromellose as film-forming agent, propylene glycol as plasticizer, BI 1356 as drug substance, and L-arginine as stabilizer, and (3) over-coating: by an aqueous film-coating suspension, containing hypromellose as film-forming agent, propylene glycol as plasticizer, talc as glidant and the pigments yellow iron oxide and/or red iron oxide and titanium dioxide, Narrative more specific description of the manufacturing process for the film-coating with a coating machine:
a) Hypromellose and propylene glycol are dissolved in purified water with a propeller mixer. Talc, titanium dioxide, and iron oxide (yellow, red or yellow and red) are dispersed in purified water with a homo-mixer. The suspension is added into the hypromellose solution, then mixed with a propeller mixer at ambient temperature to produce the "Coating Suspension" for "seal-coating" and "over-coating".
b) Hypromellose, propylene glycol and L-arginine are dissolved in purified water with a propeller mixer. BI 1356 (active drug) is added into the hypromellose solution, then dispersed with a propeller mixer at ambient temperature to produce the "Drug Suspension" for "drug-loading".
c) The Metformin HCl tablets are coated with the "Coating Suspension" to the target weight gain to form the "seal-coat". The "Coating Suspension" should be stirred again before use and kept stirring slowly during the coating (spraying) process.
d) Following the seal-coating, the "Drug Suspension" is applied to the surface of the Metformin HCl tablets to form the "drug layer" (drug loading). The "Drug Suspension" should be stirred again before use and kept stirring slowly during the coating (spraying) process. The coating end point can be determined by available PAT (Process Analysis Technology).
e) After drug loading the "Coating Suspension" is applied to the BI 1356 drug-loaded tablets to form the "over-coat" and to produce the "Film-coated Tablets". The "Coating Suspension" should be stirred again before use and kept stirring slowly during the coating (spraying) process.

Product Description:

The product description of BI 1356+Metformin HCl FDC mono-layer tablets (tablet core and film-coated tablets) is shown in Table 8 and Table 9, respectively.

TABLE 8

Product Description of BI 1356 + Metformin HCl FDC Mono-layer Tablets (Tablet Core)

| Items | Dose Strength (BI 1356/metformin HCl), mg | | |
|---|---|---|---|
| | 2.5/500 | 2.5/850 | 2.5/1000 |
| Tablet shape | Oval, biconvex | Oval, biconvex | Oval, biconvex |
| Tablet size [mm] | 16.2 × 8.5 | 19.1 × 9.3 | 21.0 × 9.6 |
| Color | | white | |
| Weight | 590 | 1000 | 1180 |
| Thickness [mm], (Mean) | Approx. 5.8 | Approx. 7.3 | Approx. 7.6 |
| Crushing strength [N], (Mean) | ≥100, Approx. 140 | ≥150, Approx. 190 | ≥150, Approx. 200 |
| Disintegration time [min] | ≤15 | ≤15 | ≤15 |
| Friability [%] | ≤0.5 | ≤0.5 | ≤0.5 |

TABLE 9

Product Description of BI 1356 + Metformin HCl FDC Mono-layer Tablets (Coated)

| Items | Dose Strength (BI 1356/metformin HCl), mg | | |
|---|---|---|---|
| | 2.5/500 | 2.5/850 | 2.5/1000 |
| Color | light yellow | light orange | light red |
| Weight | 602 | 1016 | 1198 |
| Thickness [mm], (Mean) | Approx. 5.9 | Approx. 7.4 | Approx. 7.7 |
| Crushing strength [N] (Mean) | ≥100, Approx. 180 | ≥150, Approx. 240 | ≥150, Approx. 250 |
| Disintegration time [min] | ≤15 | ≤15 | ≤15 |

Stability Data:

Stability data of BI 1356+Metformin HCl FDC monolayer tablets (tablet core) with or without L-arginine is shown in the following tables (over 2 weeks, 1 month and 3 months):

2.5+500 mg tablets+12.5 mg arginine:

| Test parameter | 60° C. glass bottle | | | |
|---|---|---|---|---|
| | Initial | 2 W | 1 M | 3 M |
| Degradation BI 1356 (%) Total | <0.2 | <0.2 | <0.2 | <0.2 |

2.5+500 mg tablets+0 mg arginine:

| Test parameter | 60° C. glass bottle | | | |
|---|---|---|---|---|
| | Initial | 2 W | 1 M | 3 M |
| Degradation BI 1356 (%) Total | <0.2 | 1.1 | 2.9 | 8.5 |

2.5+1000 mg tablets+25 mg arginine:

| Test parameter | 60° C. glass bottle | | | |
|---|---|---|---|---|
| | Initial | 2 W | 1 M | 3 M |
| Degradation BI 1356 (%) Total | <0.2 | <0.2 | <0.2 | 0.2 |

2.5+1000 mg tablets+0 mg arginine:

| Test parameter | 60° C. glass bottle | | | |
|---|---|---|---|---|
| | Initial | 2 W | 1 M | 3 M |
| Degradation BI 1356 (%) Total | <0.2 | 1.9 | 4.7 | 13.6 |

The invention claimed is:

1. A method of treating type 2 diabetes mellitus comprising orally administering to a patient in need thereof a pharmaceutical composition comprising:
   (a) 1-[(4-methyl-quinazolin-2-yl)methyl]-3-methyl-7-(2-butyn-1-yl)-8-(3-(R)-amino-piperidin-1-yl)-xanthine in a dosage of 2.5 mg or 5 mg,
   (b) metformin hydrochloride,
   (c) one or more pharmaceutical excipients, and
   (d) a basic amino acid having an intramolecular amino group and alkaline characteristics, which basic amino acid is present in an amount sufficient to suppress degradation of said 1-[(4-methyl-quinazolin-2-yl)methyl]-3-methyl-7-(2-butyn-1-yl)-8-(3-(R)-amino-piperidin-1-yl)-xanthine,
   wherein the pharmaceutical composition is a tablet comprising a film-coat; and
   wherein the pharmaceutical composition comprises the following amounts: 0.1-0.5% of 1-[(4-methyl-quinazolin-2-yl)methyl]-3-methyl-7-(2-butyn-1-yl)-8-(3-(R)-amino-piperidin-1-yl)-xanthine, 47-85% of metformin hydrochloride, and 0.07-2.2% of the basic amino acid, wherein each of the foregoing percentage amounts are based on the weight of total coated tablet mass.

2. The method according to claim 1, wherein the basic amino acid having an intramolecular amino group and alkaline characteristics is selected from L-arginine, L-lysine and L-histidine.

3. The method according to claim 1, wherein 1-[(4-methyl-quinazolin-2-yl)methyl]-3-methyl-7-(2-butyn-1-yl)-8-(3-(R)-amino-piperidin-1-yl)-xanthine is present in a dosage strength of 5 mg.

4. The method according to claim 1, wherein 1-[(4-methyl-quinazolin-2-yl)methyl]-3-methyl-7-(2-butyn-1-yl)-8-(3-(R)-amino-piperidin-1-yl)-xanthine is present in a dosage strength of 2.5 mg.

5. The method according to claim 1, wherein metformin hydrochloride is present in a dosage range from about 100 mg to about 1500 mg.

6. The method according to claim 5, wherein metformin hydrochloride is present in a dosage strength of 250, 500, 625, 750, 850, or 1000 mg.

7. The method according to claim 5, wherein metformin hydrochloride is present in a dosage strength of 500 mg, 850 mg, or 1000 mg.

8. The method according to claim 1, wherein the basic amino acid having an intramolecular amino group and alkaline characteristics is L-arginine, and wherein the L-arginine is present from about 1 mg to about 25 mg.

9. The method according to claim 1 comprising the active ingredients in a dosage strength of 2.5 mg of 1-[(4-methyl-quinazolin-2-yl)methyl]-3-methyl-7-(2-butyn-1-yl)-8-(3-(R)-amino-piperidin-1-yl)-xanthine and 500 mg of metformin hydrochloride.

10. The method according to claim 1 comprising the active ingredients in a dosage strength of 2.5 mg of 1-[(4-methyl-quinazolin-2-yl)methyl]-3-methyl-7-(2-butyn-1-yl)-8-(3-(R)-amino-piperidin-1-yl)-xanthine and 850 mg of metformin hydrochloride.

11. The method according to claim 1 comprising the active ingredients in a dosage strength of 2.5 mg of 1-[(4-methyl-quinazolin-2-yl)methyl]-3-methyl-7-(2-butyn-1-yl)-8-(3-(R)-amino-piperidin-1-yl)-xanthine and 1000 mg of metformin hydrochloride.

12. A method of treating type 2 diabetes mellitus comprising orally administering to a patient in need thereof a solid pharmaceutical composition which is a mono-layer tablet comprising:
   1-[(4-methyl-quinazolin-2-yl)methyl]-3-methyl-7-(2-butyn-1-yl)-8-(3-(R)-amino-piperidin-1-yl)-xanthine in a dosage of 2.5 mg,
   metformin hydrochloride,
   L-arginine in an amount sufficient to suppress degradation of 1-[(4-methyl-quinazolin-2-yl)methyl]-3-methyl-7-(2-butyn-1-yl)-8-(3-(R)-amino-piperidin-1-yl)-xanthine, and one or more fillers and one or more binders,
   wherein the percentage of 1-[(4-methyl-quinazolin-2-yl)methyl]-3-methyl-7-(2-butyn-1-yl)-8-(3-(R)-amino-piperidin-1-yl)-xanthine is about 0.2%-0.4%, by weight of total tablet core and,
   wherein the DPP-4 inhibitor and L-arginine are comprised in a weight ratio of from about 1:10 to about 10:1.

13. The method according to claim 12, wherein metformin hydrochloride is present in a dosage range from about 100 mg to about 1500 mg.

14. The method according to claim 13, wherein metformin hydrochloride is present in a dosage strength of 250, 500, 625, 750, 850, or 1000 mg.

15. The method according to claim 13, wherein metformin hydrochloride is present in a dosage strength of 500 mg, 850 mg, or 1000 mg.

16. The method according to claim 12, wherein the L-arginine is present from about 1 mg to about 25 mg.

17. The method according to claim 12 comprising 500 mg of metformin hydrochloride.

18. The method according to claim 12 comprising 850 mg of metformin hydrochloride.

19. The method according to claim 12 comprising 1000 mg of metformin hydrochloride.

20. A method of achieving glycemic control in a type 2 diabetes patient comprising orally administering to the patient a pharmaceutical composition comprising:
   (a) 1-[(4-methyl-quinazolin-2-yl)methyl]-3-methyl-7-(2-butyn-1-yl)-8-(3-(R)-amino-piperidin-1-yl)-xanthine in a dosage of 2.5 mg or 5 mg,
   (b) metformin hydrochloride,
   (c) one or more pharmaceutical excipients, and
   (d) a basic amino acid having an intramolecular amino group and alkaline characteristics, which basic amino acid is present in an amount sufficient to suppress degradation of said 1-[(4-methyl-quinazolin-2-yl)methyl]-3-methyl-7-(2-butyn-1-yl)-8-(3-(R)-amino-piperidin-1-yl)-xanthine,
   wherein the pharmaceutical composition is a tablet comprising a film-coat; and
   wherein the pharmaceutical composition comprises the following amounts: 0.1-0.5% of 1-[(4-methyl-quinazolin-2-yl)methyl]-3-methyl-7-(2-butyn-1-yl)-8-(3-(R)-amino-piperidin-1-yl)-xanthine, 47-85% of metformin hydrochloride, and 0.07-2.2% of the basic amino acid, wherein each of the foregoing percentage amounts are based on the weight of total coated tablet mass.

* * * * *